United States Patent
Granier et al.

(10) Patent No.: US 9,012,391 B2
(45) Date of Patent: Apr. 21, 2015

(54) ORGANIC COMPOUNDS

(75) Inventors: Thierry Granier, Duebendorf (CH); Nicolas Anorga, Paris (FR); Markus Gautschi, Fällanden (CH); Bernadette Bourdin Trunz, Petit-Lancy (CH)

(73) Assignee: Givaudan SA, Vernier (CH)

( * ) Notice: Subject to any disclaimer, the term of this patent is extended or adjusted under 35 U.S.C. 154(b) by 364 days.

(21) Appl. No.: 12/663,797

(22) PCT Filed: Jun. 9, 2008

(86) PCT No.: PCT/CH2008/000260
§ 371 (c)(1),
(2), (4) Date: May 20, 2010

(87) PCT Pub. No.: WO2008/151455
PCT Pub. Date: Dec. 18, 2008

(65) Prior Publication Data
US 2010/0292128 A1 Nov. 18, 2010

(30) Foreign Application Priority Data

Jun. 11, 2007 (EP) .................................. 07290735

(51) Int. Cl.
*C11B 9/00* (2006.01)
*C07C 49/557* (2006.01)
*C07C 45/65* (2006.01)
*C07C 49/323* (2006.01)
*C07C 49/553* (2006.01)
*C07C 67/317* (2006.01)
*C07C 69/753* (2006.01)

(52) U.S. Cl.
CPC .............. *C07C 49/557* (2013.01); *C07C 45/65* (2013.01); *C07C 49/323* (2013.01); *C07C 49/553* (2013.01); *C07C 67/317* (2013.01); *C07C 69/753* (2013.01); *C07C 2102/50* (2013.01); *C11B 9/0057* (2013.01)

(58) Field of Classification Search
CPC .... C07C 45/65; C07C 49/323; C07C 49/553; C07C 49/557; C07C 67/317; C07C 69/753; C07C 45/61; C07C 49/543; C07C 67/30; C07C 2102/50; C11B 9/0057; C11B 9/00
USPC .............................. 512/9; 560/118, 8; 568/367
See application file for complete search history.

(56) References Cited

U.S. PATENT DOCUMENTS

| | | | |
|---|---|---|---|
| 3,962,147 A * | 6/1976 | Maurer et al. | 512/9 |
| 4,098,823 A * | 7/1978 | Arndt et al. | 568/367 |
| 4,281,204 A * | 7/1981 | Willis et al. | 568/361 |
| 5,804,169 A | 9/1998 | Ramin | |
| 8,268,846 B2 * | 9/2012 | Wakefield et al. | 514/267 |
| 8,278,313 B2 * | 10/2012 | Liu et al. | 514/266.2 |
| 8,299,296 B2 * | 10/2012 | Shimada et al. | 562/466 |
| 2009/0257974 A1 * | 10/2009 | Evans et al. | 424/76.6 |

FOREIGN PATENT DOCUMENTS

| | | |
|---|---|---|
| DE | 2925176 A1 | 1/1981 |
| WO | 2005020938 A1 | 3/2005 |

OTHER PUBLICATIONS

H. Christol et al., "Acid-Catalyzed Rearrangements", Bulletin de la Societe Chimique de France, 1957, 1027-1039 (French language).*
CAS reg. No. 1093269-12-5, Jan. 12, 2009.*
Cooke, "Formation of Polycyclic Carbocycles through Metal-Halogen Exchange-Initiated Intramolecular Conjugate Addition Reactions", J. Org. Chem. 1993, 58, 2910-2912.*
Tetrahedron Letters, 2002, vol. 43(1), pp. 151-154.
XP002497268 Stereoselective Synthesis of Functionalized Carbocycles and Heterocycles via an Ester Enolate Claisen/Ring-Closing Metathesis Manifold, Miller, John F. et al., Journal of Organic Chemistry, vol. 63, No. 10, 1998. pp. 3158-3159, table 1.
XP002497269 A Novel Bornane Synthesis by an Old Idea, Foehlisch, Baldur et al., Journal of Organic Chemistry, vol. 67, No. 11, 2002m pp. 3682-3686.
XP002497270 Formation of Polycyclic Carbocycles Through Metal-Halogen Exchange-Initiated Intramolecular Conjugate Addition Reactions, Cooke, Manning P., Jr., Journal of Organic Chemistry, vol. 58, No. 10, 1993, pp. 2910-2912.
XP002497271 The Tricyclo[6. 3. 0. 04, 8]Undecane System, Cargil, Robert L. et al., Journal of Organic Chemistry, vol. 35, No. 6, 1970, pp. 1971-1973.
XP002497847 An RCM Based Approach to (. + −.) -herbertene-1,14-diol and (.+−.)-tochuinyl Acetates, Srikrishna, A. et al., Journal of CHemistry, Section B: Organic Chemistry Including Medicinal Chemistry, vol. 46B, No. 8, 2007, pp. 1308-1317.
English Language Abstract Translation for DE2925176 taken from esp@cenet.com.
"A Sequential Claisen/Ring-Closing Metathesis approach to the Synthesis of Spirocyclic Cyclopentanes and Cyclohexanes", Patrick Beaulieu, et al., Tetrahedron Letters, Department of Chemistry, University of Ottawa, Ontario, Canada, Sep. 2003, pp. 8883-8885.
International Cosmetic Ingredient Dictionary and Handbook, vol. 1, 11th edition, pp. 822, 831 and 992, Washington, D.C., 2006.
International Cosmetic Ingredient Dictionary and Handbook, vol. 2, 11th edition, pp. 1714-1715, Washington, D.C., 2006.

* cited by examiner

*Primary Examiner* — Douglas McGinty
(74) *Attorney, Agent, or Firm* — Norris McLaughlin & Marcus, P.A.

(57) ABSTRACT

Described are spiroalkyl- and -alkenylketones and esters thereof, a method for their production and fragrance compositions comprising them.

18 Claims, No Drawings

ORGANIC COMPOUNDS

This application filed under 35 USC 371 of PCT/CH2008/000260.

The present invention refers to a novel class of spiroalkyl- and -alkenylketones and esters thereof possessing damascone-like odour notes and to their use as odorants. This invention relates furthermore to a method for their production and for fragrance compositions comprising them.

In the fragrance industry there is a constant demand for new compounds that enhance, modify or improve on odour notes. Damascones, also known as rose ketones, constitute an important class of perfume ingredients. They display particular floral (rosy)-fruity notes reminiscent of dried fruits. Thus, there is a constant desire to find new compounds possessing a damascone-like odour note.

The present invention refers in one of its aspects to the use as fragrance of a compound of formula (I)

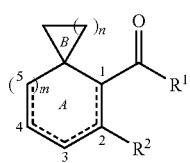

wherein
n is 1, 2, 3, or 4;
m is 0 or 1;
$R^1$ is selected from $C_1$-$C_4$ alkoxy (e.g. methoxy, ethoxy, propoxy, butoxy), $C_3$-$C_4$ cycloalkyloxy (e.g. cyclopropyloxy, methylcyclopropyloxy), $C_2$-$C_4$ alkenoxy (e.g. allyloxy), $C_2$-$C_5$ alkyl (e.g. butyl, pentyl), $C_2$-$C_5$ alkenyl (e.g. prop-1-enyl, prop-2-enyl, methylpropenyl), cyclopropyl, 2-methylcyclopropyl, 1-methylcyclopropyl, and cyclopropylmethyloxy;
$R^2$ is selected from hydrogen, methyl, ethyl, methylene, and ethylidene;
ring A is saturated, or unsaturated comprising 1 double bond (i.e. between C-1 and C-2, C-2 and C-3, C-3 and C-4, or C-4 and C-5) or 2 double bonds (between C-1 and C-2 and C-3 and C-4, between C-1 and C-2 and C-4 and C-5, or between C-2 and C-3 and C-4 and C-5); and
ring B is saturated, or unsaturated comprising 1 double bond or 2 double bonds.

The compounds of the present invention comprise several chiral centres and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

Non-limiting examples are those compounds of formula (I) wherein m is 1, n is 1 or 3, and $R^2$ is methyl.

Further non-limiting examples are compounds of formula (I) wherein m is 1, n is 1, $R^1$ is prop-1-enyl and $R^2$ is hydrogen or methyl, or compounds of formula (I) wherein m is 1, n is 1, $R^1$ is methoxy or ethoxy, and $R^2$ is methyl or methylene.

In particular embodiments are compounds of formula (I) selected from (E)-1-(7-methylspiro[4.5]dec-8-en-6-yl)but-2-en-1-one (Ex. 1),
methyl 7-methylspiro[4.5]dec-8-ene-6-carboxylate (Ex. 2),
ethyl 7-methylspiro[4.5]dec-8-ene-6-carboxylate (Ex. 3),
allyl 7-methylspiro[4.5]dec-8-ene-6-carboxylate (Ex. 4),
methyl 7-methylspiro[4.5]decane-6-carboxylate (Ex. 5),
ethyl 7-methylspiro[4.5]decane-6-carboxylate (Ex. 6),
1-(7-methylspiro[4.5]decan-6-yl)butan-1-one (Ex. 7),
1-(7-methylspiro[4.5]dec-8-en-6-yl)butan-1-one (Ex. 8),
(E)-1-(7-methylspiro[4.5]decan-6-yl)but-2-en-1-one (Ex. 9),
(E)-1-(spiro[4.5]dec-6-en-6-yl)but-2-en-1-one (Ex. 10),
(E)-1-(5-methylspiro[2.5]oct-6-en-4-yl)but-2-en-1-one (Ex. 11, 12),
(E)-1-(5-methylspiro[2.5]oct-5-en-4-yl)but-2-en-1-one (Ex. 13),
ethyl 7-methylspiro[4.5]dec-7-ene-6-carboxylate (Ex. 14 & 18),
(E)-1-(7-methylspiro[4.5]dec-7-en-6-yl)but-2-en-1-one (Ex. 15),
(E)-1-(7-methylspiro[4.5]dec-6-en-6-yl)but-2-en-1-one (Ex. 15),
ethyl 7-methylenespiro[4.5]dec-8-ene-6-carboxylate (Ex. 16),
ethyl 7-methylspiro[4.5]deca-6,8-diene-6-carboxylate (Ex. 16 & 22),
ethyl 7-methylspiro[4.5]deca-7,9-diene-6-carboxylate (Ex. 16),
(2-methylcyclopropyl)(7-methylspiro[4.5]dec-8-en-6-yl)methanone (Ex. 17),
methyl 7-methylspiro[4.5]dec-7-ene-6-carboxylate (Ex. 25),
methyl 7-methylspiro[4.5]dec-6-ene-6-carboxylate (Ex. 26),
ethyl 7-methylspiro[4.5]dec-6-ene-6-carboxylate (Ex. 27),
(E)-1-(7-methylspiro[4,5]dec-6-en-6-yl)but-2-en-1-one,
methyl 7-methylspiro[4.5]dec-9-ene-6-carboxylate,
ethyl 7-methylspiro[4.5]dec-9-ene-6-carboxylate (Ex. 19),
(E)-1-(7-methylspiro[4.5]dec-9-en-6-yl)but-2-en-1-one (Ex. 21),
(E)-1-(7-methylspiro[4.5]deca-6,8-dien-6-yl)but-2-en-1-one (Ex. 31),
(E)-1-(7-methylspiro[4.5]deca-7,9-dien-6-yl)but-2-en-1-one (Ex. 33),
(E)-1-(7-methylenespiro[4.5]dec-8-en-6-yl)but-2-en-1-one (Ex. 32),
methyl 2-methylspiro[4.4]non-1-ene-1-carboxylate,
ethyl 2-methylspiro[4.4]non-1-ene-1-carboxylate,
(E)-1-(2-methylspiro[4.4]non-1-en-1-yl)but-2-en-1-one,
methyl 2-methylspiro[4.4]non-2-ene-1-carboxylate,
ethyl 2-methylspiro[4.4]non-2-ene-1-carboxylate,
(E)-1-(2-methylspiro[4.4]non-2-en-1-yl)but-2-en-1-one,
cyclopropyl(7-methylspiro[4.5]dec-8-en-6-yl)methanone,
(2-methylcyclopropyl)(7-methylspiro[4.5]deca-6,8-dien-6-yl)methanone,
cyclopropyl(7-methylspiro[4.5]deca-6,8-dien-6-yl)methanone,
methyl 7-ethylidenespiro[4.5]decane-6-carboxylate,
ethyl 7-ethylidenespiro[4.5]decane-6-carboxylate,
(2E)-1-(7-ethylidenespiro[4.5]decan-6-yl)but-2-en-1-one,
methyl 7-methylspiro[4.5]dec-9-ene-6-carboxylate (Ex. 20),
methyl 7-methylspiro[4.5]deca-6,8-diene-6-carboxylate (Ex. 23),
methyl 7-methylenespiro[4.5]dec-8-ene-6-carboxylate (Ex. 24),
ethyl 7-methylenespiro[4.5]decane-6-carboxylate (Ex. 28),
methyl 7-methylenespiro[4,5]decane-6-carboxylate (Ex. 29),
(E)-1-(7-methylenespiro[4.5]decan-6-yl)but-2-en-1-one (Ex. 30), (E)-1-(spiro[4.5]deca-2,6-dien-6-yl)but-2-en-1-one (Ex. 34),
(E)-1-(7-methylspiro[4.5]deca-2,6-dien-6-yl)but-2-en-1-one,
(E)-1-(7-methylspiro[4.5]deca-2,7-dien-6-yl)but-2-en-1-one,
(E)-1-(7-methylspiro[4,5]deca-2,8-dien-6-yl)but-2-en-1-one,
(E)-1-(7-methylenespiro[4.5]dec-2-en-6-yl)but-2-en-1-one, and
(E)-1-(7-methylspiro[4.5]deca-2,6,8-trien-6-yl)but-2-en-1-one.

The compounds according to the present invention may be used alone or in combination with known odorant molecules selected from the extensive range of natural and synthetic molecules currently available, such as essential oils and extracts, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art, e.g., solvents such as dipropylen glycol, isopropylmyristate, and triethylcitrate.

The following list comprises examples of known odorant molecules, which may be combined with the compounds of the present invention:

essential oils and extracts, e.g. oak moss absolute, basil oil, tropical fruit oils, such as bergamot oil and mandarine oil, mastic absolute, myrtle oil, palmarosa oil, patchouli oil, petitgrain oil, wormwood oil, lavender oil, rose oil, jasmin oil, ylang-ylang oil and sandalwood oil.

alcohols, e.g. cis-3-hexenol, cinnamic alcohol, citronellol, Ebanol®, eugenol, farnesol, geraniol, menthol, nerol, rhodinol, Super Muguet™, linalool, phenylethyl alcohol, Sandelore®, terpineol and Timberol® (1-(2,2,6-Trimethylcyclohexyl)hexan-3-ol).

aldehydes and ketones, e.g. citral, hydroxycitronellal, Lilial®, methylnonylacetaldehyde, anisaldehyde, allylionone, verbenone, nootkatone, geranylacetone, α-amylcinnamic aldehyde, Georgywood™, hydroxycitronellal, Iso E Super®, Isoraldeine® (methylionone), Hedione®, maltol, methyl cedryl ketone, and vanillin.

ethers and acetals, e.g. Ambrox®, geranyl methyl ether, rose oxide or Spirambrene®.

esters and lactones, e.g. benzyl acetate, cedryl actetate, γ-decalactone, Helvetolide®, γ-undecalactone, vetivenyl acetate, cinnamyl propionate, citronellyl acetate, decyl acetate, dimethylbenzylcarbinyl acetate, ethyl acetoacetate, cis-3-hexenyl isobutyrate, linalyl acetate and geranyl acetate.

macrocycles, e.g. ambrettolide, ethylene brassylate or Exaltolide®.

heterocycles, e.g. isobutylquinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odorant ingredients. The proportion is typically from 0.0001 to 2 weight percent of the application. In one embodiment, compounds of the present invention may be employed in a fabric softener in an amount of from 0.0001 to 0.005 weight percent. In another embodiment, compounds of the present invention may be used in an alcoholic solution in amounts of from 0.01 to 3 weight percent, more preferably between 0.5 and 2 weight percent. However, these values are given only by way of example, since the experienced perfumer may also achieve effects or may create novel accords with lower or higher concentrations, e.g. up to about 20 weight percent based on the fragrance composition.

The compounds of the present invention may be employed into the fragrance application simply by directly mixing the fragrance composition with the fragrance application, and/or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, and/or they may be chemically bonded to substrates, which are adapted to release the fragrance molecule upon application of an external stimulus such as light, enzyme, or the like, and then mixed with the application.

Thus, the invention additionally provides a method of manufacturing a fragrance application and consumer products resulting therefrom. The method comprises the incorporation therein of a compound of formula (I) as a fragrance ingredient, either by directly admixing the compound to the application or by admixing a fragrance composition comprising a compound of formula (I) or a precursor thereof, which may then be mixed to a fragrance application, using conventional techniques and methods. Through the addition of an olfactory acceptable amount of a compound of the present invention, the odour notes of a fragrance application will be improved, enhanced or modified.

By "precursors" is meant, in particular, reaction products of a compound of formula (I) with a compound comprising at least one functional group selected from the group of primary amine, secondary amine, sulfhydril (thiol), hydroxyl and carboxyl, in which a covalent bond is formed between at least one carbon atom of the compound of formula (I) and at least one of the hetero atoms of said compounds comprising at least one functional group selected from the group of N, S and O.

In a further aspect, the invention provides a method for improving, enhancing or modifying a fragrance application through the addition thereto of an olfactory acceptable amount of a compound of formula (I), or a mixture thereof.

The invention also provides a fragrance application comprising:
a) as odorant a compound of formula (I) or a mixture thereof; and
b) a consumer product base.

As used herein, "fragrance application" means any consumer products, such as fine fragrances, e.g. eaux de perfume and eaux de toilette; household products, e.g. detergents for dishwasher, surface cleaner, air freshener; laundry products, e.g. softener, bleach, detergent; body care products, e.g. aftershave lotion, shampoo, shower gel, shower and bath salt, hygiene product; and cosmetics, e.g. deodorants, vanishing creams, comprising an odorant. This list of products is given by way of illustration and is not to be regarded as being in any way limiting.

As used herein, "consumer product base" means a composition for use as a consumer product to fulfill specific actions, such as cleaning, softening, and caring or the like. Examples of such products include fabric care and personal care products such as laundry care detergents, rinse conditioners, personal cleansing compositions. The composition may comprise a variety of active ingredients such as surfactants, polymers, fillers and auxiliary agents, such as dyes and solvents.

Most of the compounds of formula (I) are described hereinabove for the first time and thus are novel in its own right.

Accordingly, the present invention refers in a further aspect to compounds of formula (I)

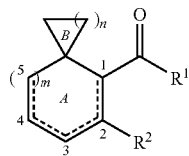

(I)

wherein n is 1, 2, 3, or 4;

m is 0 or 1;

$R^1$ is selected from $C_1$-$C_4$ alkoxy (e.g. methoxy, ethoxy, propoxy, butoxy), $C_3$-$C_4$ cycloalkyloxy (e.g. cyclopropyloxy, methylcyclopropyloxy), $C_2$-$C_4$ alkenoxy (e.g. allyloxy), $C_2$-$C_5$ alkyl (e.g. butyl, pentyl), $C_2$-$C_5$ alkenyl (e.g. prop-1-enyl, prop-2-enyl, methylpropenyl), cyclopropyl, 2-methylcyclopropyl, 1-methylcyclopropyl, and cyclopropylmethyloxy;

$R^2$ is selected from hydrogen, methyl, ethyl, methylene, and ethylidene;

ring A is saturated, or unsaturated comprising 1 double bond (i.e. between C-1 and C-2, C-2 and C-3, C-3 and C-4, or C-4 and C-5) or 2 double bonds (between C-1 and C-2 and C-3 and C-4, between C-1 and C-2 and C-4 and C-5, or between C-2 and C-3 and C-4 and C-5);

ring B is saturated, or unsaturated comprising 1 double bond or 2 double bonds;

provided that compounds of formula (I) wherein m=0, n=4, $R^1$=ethoxy, $R^2$=hydrogen, and ring A comprises 1 double bond between C-3 and C-4 (i.e. ethyl spiro[4.5]dec-3-ene-1-carboxylate);

m=0, n=1, $R^1$=ethoxy, $R^2$=hydrogen, and ring A comprises double bonds between C-1 and C-2 and C-3 and C-4 (i.e. ethyl spiro[2.4]hepta-4,6-diene-4-carboxylate);

m=0, n=1, $R^1$=methoxy, $R^2$=hydrogen, and ring a comprises double bonds between C-1 and C-2 and C-3 and C-4 (i.e. methyl spiro[2.4]hepta-4,6-diene-4-carboxylate);

m=0, n=3, $R^1$=methoxy, $R^2$=hydrogen, and ring A is saturated (i.e. methyl spiro[4.4]nonane-1-carboxylate);

m=1, n=3, $R^1$=tert-butoxy, $R^2$=hydrogen, and ring A is saturated (i.e. tert-butyl spiro[4.5]decane-6-carboxylate);

m=1, n=4, $R^1$=methoxy, $R^2$=hydrogen, and ring A comprises a double bond between C-4 and C-5 (i.e. methyl spiro[5.5]undec-4-ene-1-carboxylate) are excluded.

The compounds of formula (I) are accessible from spiroolefines by acylation (Kondakov reaction) or from the corresponding spiroalkanones either by Rupe rearrangement via the corresponding tertiary alkynols, or by cyanide addition followed by water elimination and further transformations as shown in Scheme 1.

Scheme 1:

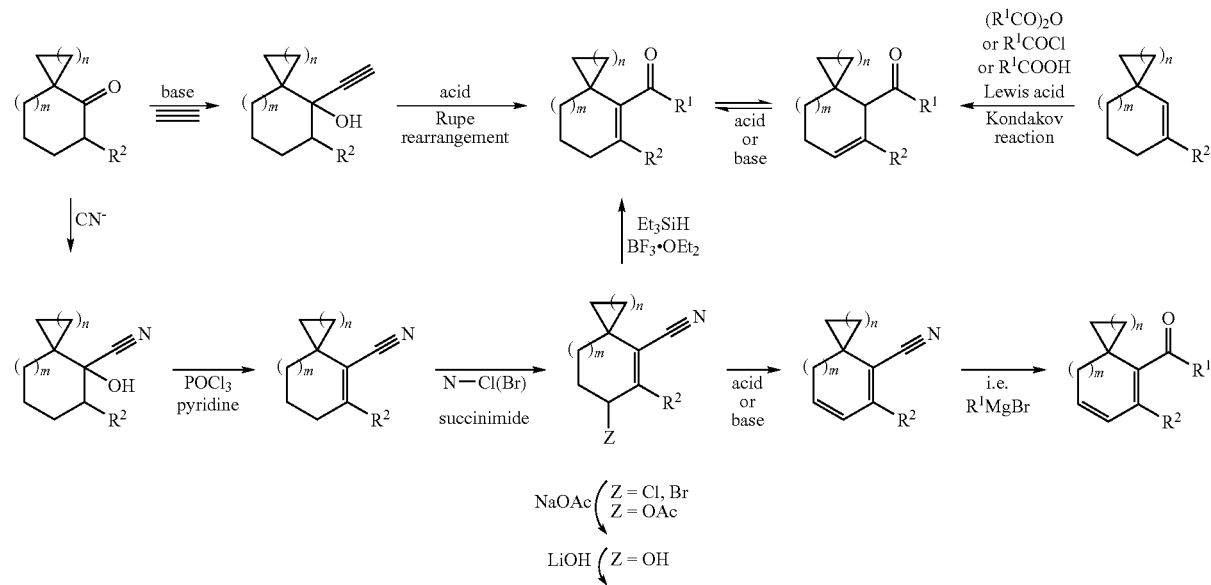

n, m, $R^1$, and $R^2$ have the same meaning as given for formula (I) hereinabove.

More specifically, compounds of formula (I) wherein m is 1 may be prepared by acid-catalyzed cyclization of cycloalkylidenylolefines, as shown in Scheme 2, a). Alternatively, cyclocondensation of alkylidenones with malonic acid derivatives allows the preparation of compounds according to formula (I), and of some of their double bond-isomers, and of more unsaturated analogues, as depicted in Scheme 2, b). Optionally the compounds of formula (I) wherein m is 1 may also be prepared, using the appropriated alkylidenone or 5-cycloalkylidene-2,2-dimethyl-1,3-dioxane-4,6-dione as dienophile in the presence of a diene, as shown in Scheme 2, c), followed by hydrolysis of the resulting compound.

Moreover, cyclic beta-ketoesters are also starting material for the synthesis of the compounds of formula (I) wherein m is 1 (see Scheme 3).

Spiroalkylketones and esters, i.e. compounds of formula (I) wherein ring A is saturated, are accessible by hydrogenation of the corresponding spiroalkenylketones and esters under conditions known to the person skilled in the art.

Scheme 2:
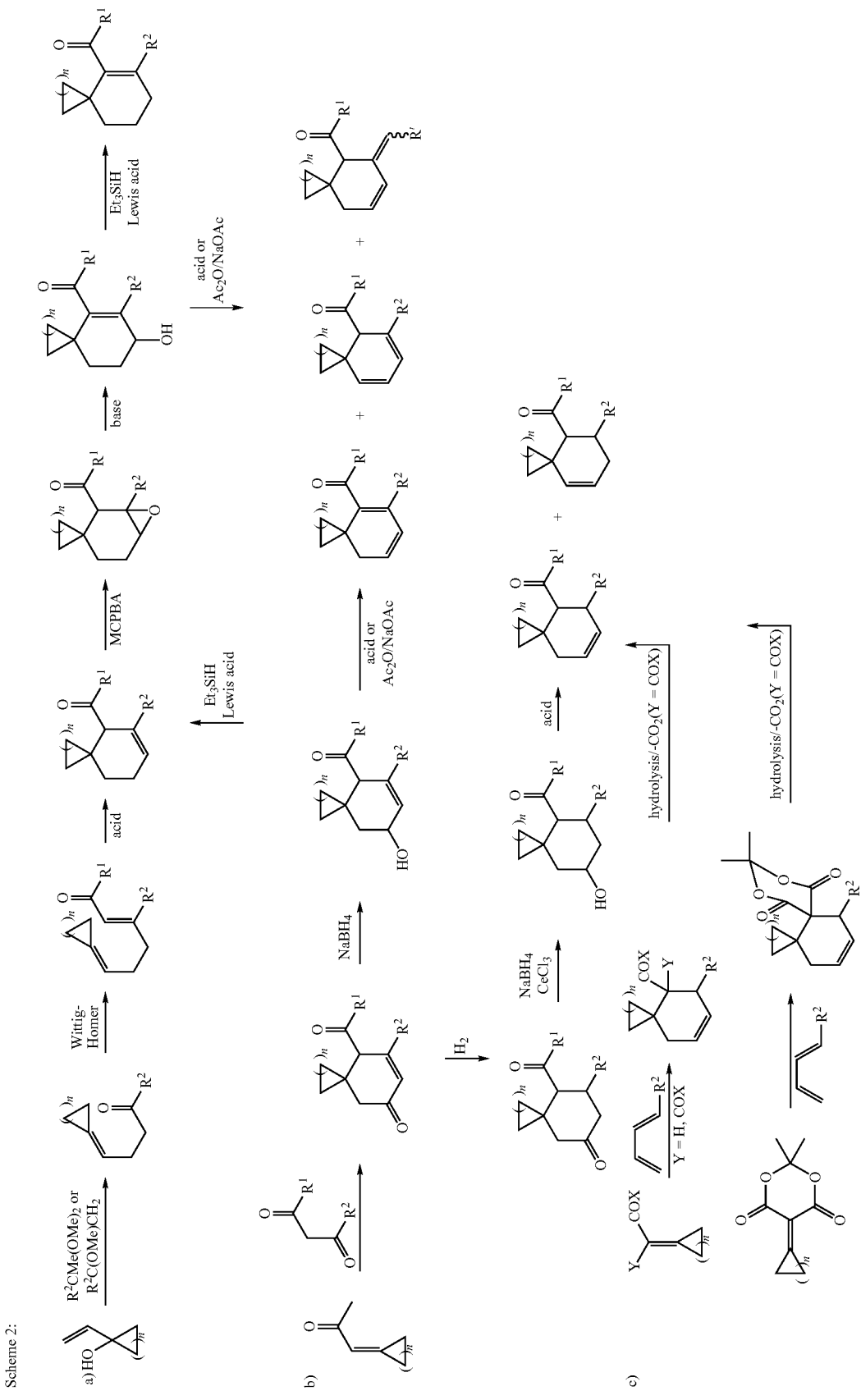

R' is hydrogen or methyl, Y is hydrogen and X is methyl, methoxy, ethoxy, hydroxyl or Cl, or Y is $CO_2CH_3$ or $CO_2C_2H_5$ and X is methyl, methoxy or ethoxy; n, $R^1$, and $R^2$ have the same meaning as given for formula (I) hereinabove.

Scheme 3:

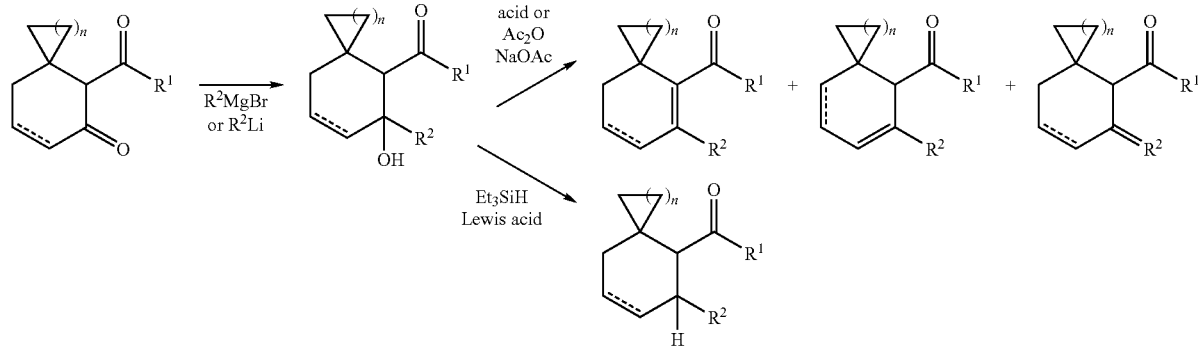

n, $R^1$, and $R^2$ have the same meaning as given for formula (I) hereinabove.

A further aspect of the present invention refers to the preparation of compounds of formula (I) comprising elimination of HX from a compound of formula (II) under acidic or basic conditions

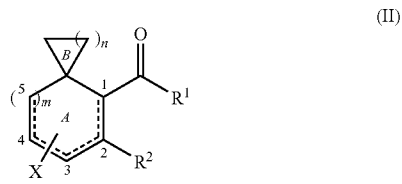

(II)

wherein n, m, $R^1$ and $R^2$ have the same meaning as given above for formula (I);

ring A is saturated, or unsaturated comprising 1 double bond (i.e. between C-1 and C-2, C-2 and C-3, C-3 and C-4, or C-4 and C-5);

ring B is saturated, or unsaturated comprising 1 double bond or 2 double bonds; and X is selected from —OR" wherein R" is selected from hydrogen, $C_1$-$C_{12}$ alkyl, or $C_2$-$C_{12}$ alkenyl, —O—C(O)R''' wherein R''' is $C_1$ to $C_{12}$ alkyl, or —O—$CO_2R^{IV}$ wherein $R^{IV}$ is $C_1$ to $C_{12}$ alkyl, and X is bound to C-2, C-3 or C-4.

Preferably compounds of formula (II) may be selected form the group wherein X is OH bound to C-2 or C-4, and ring A is saturated; or X is OH bound to C-2 and ring A comprises 1 double bond between C-3 and C-4, or X is OH bound to C-3 and ring A comprises 1 double bond between C-1 and C-2; or X is OH bound to C-4 and ring A comprises 1 double bond between C-2 and C-3.

The invention is now further described with reference to the following non-limiting examples. These examples are for the purpose of illustration only and it is understood that variations and modifications can be made by one skilled in the art.

Example 1

(E)-1-(rel-(6S,7R)-7-Methylspiro[4.5]dec-8-en-6-yl) but-2-en-1-one and (E)-1-(rel-(6R,7R)-7-methylspiro [4.5]dec-8-en-6-yl )but-2-en-1-one 3,3,15-Trimethyl-2,4-dioxadispiro[5.0.4.4]pentadec-13-ene-1,5-dione A mixture of 5-cyclopentylidene-2,2-dimethyl-1,3-dioxane-4,6-dione (194 g, 0.92 mol, prepared from cyclopentanone and Meldrum acid in pyridine in the presence of piperidine), 1,3-pentadiene (409 ml, 90%, 3.69 mol), and BHT (50 mg) was heated at 110° C. for 42 h. The reaction mixture was then concentrated (95° C., 0.1 mbar) and the residue (204 g) purified by thin film evaporation (at 180° C. and 0.09 mbar, head temperature: 85° C.) giving the desired diester (177 g, 89% pure, 61% yield). Boiling point: 190° C. (0.09 mbar).

$^1$H-NMR (400 MHz, CDCl$_3$): δ5.67 (ddt, J=2.9, 4.3, 10.1, 1 H), 5.54 (dq, J=2.0, 10.1, 1 H), 3.23-3.14 (m, H—C(7')), 2.19-2.08 (m, 1 H), 2.06-2.02 (m, 2 H), 1.72 (br. s, MeCO), 1.69 (br. s, MeCO), 1.67-1.61 (m, 5 H), 1.54-1.46 (m, 1 H), 1.43-1.36 (m, 1 H), 1.08 (d, J=7.3, MeC(7')).

$^{13}$C-NMR (100 MHz, CDCl$_3$): δ168.51 (s, CO), 165.77 (s, CO), 129.90 (d), 124.04 (d), 104.77 (s, CMe$_2$), 61.44 (s, C(6')), 50.32 (s, C(5')), 36.76 (t), 35.92 (t), 34.61 (d, C(7')), 32.75 (t), 31.42 (q, MeCO), 27.86 (q, MeCO), 24.11 (t), 23.52 (t), 16.73 (q).

MS (EI): 278 (1), 263 (1), 220 (5), 202 (14), 176 (20), 174 (12), 161 (37), 147 (29), 134 (12), 133 (16), 119 (65), 117 (21), 107 (29), 105 (54), 91 (100), 79 (32), 77 (29), 67 (18), 65 (17), 58 (22), 44 (25), 43 (55).

b) 1-(rel-(6S,7R)-7-Methylspiro[4.5]dec-8-en-6-yl) ethanone (trans) and 1-(rel-(6R,7R)-7-methylspiro [4.5]dec-8-en-6-yl)ethanone (cis)

At −20° C., a solution of 3,3,15-trimethyl-2,4-dioxadispiro [5.0.4.4]pentadec-13-ene-1,5-dione (85 g, 80% pure, 244 mmol) in tetrahydrofuran (850 ml) was treated within 15 min. with methyllithium (427 ml, 1.6M in diethyl ether, 683 mmol). The resulting solution was warmed to 10° C. by removing the cooling bath before being refluxed for 3 h, cooled at 0° C., poured into a mixture of 2N aqueous NaOH and ice, and extracted twice with methyl-tert-butyl ether (MTBE, 400 ml). The combined organic phases were washed with water, dried (MgSO$_4$), and concentrated giving unreacted starting material (20 g, 46% pure). The aqueous phase was acidified with 2N aqueous HCl to pH 1 and extracted three times with MTBE (450 ml), washed twice with a saturated aqueous solution of NaCl, dried (MgSO$_4$), and concentrated giving the crude intermediate ketoacid (52.2 g) which was refluxed in pyridine (520 ml) during 2 h. The resulting mixture was concentrated and the residue was poured into 2N aqueous HCl and ice, and extracted three times with MTBE (350 ml). The combined organic phases washed to pH 7, dried (MgSO$_4$), and concentrated. Short-path distillation (bath temperature 110° C., head temperature: 70-85° C., 0.09 mbar) of the crude product (39.3 g) gave a diastereomeric mixture of the desired methyl ketones (30.7 g, 66%, rel-(6S, 7R)/rel-(6R,7R) 30:70). Sodium (2.2 g, 96 mmol) was added to ethanol (300 ml) and the resulting solution was treated with a solution of 30:70 mixture of 1-(rel-(6S,7R)-7-methylspiro

[4.5]dec-8-en-6-yl)ethanone and 1-(rel-(6R,7R)-7-methylspiro[4.5]dec-8-en-6-yl)ethanone (30.7 g, 160 mmol) in ethanol (30 ml). The resulting solution was refluxed for 48 h, cooled to 0° C., poured into 2N aqueous HCl and ice, and extracted three times with MTBE (350 ml). The combined organic phases washed three times with a saturated aqueous solution of NaCl, dried (MgSO$_4$), and concentrated. Short-path distillation (bath temperature 110° C., head temperature 85° C., 0.09 mbar) of the crude product (32.9 g) gave a diastereomeric mixture of the desired methyl ketones (26.8 g, 87%, rel-(6S,7R)/rel-(6R,7R) 85:15). Boiling point: 80° C. (0.09 mbar).

Data of 1-(rel-(6R,7R)-7-methylspiro[4.5]dec-8-en-6-yl)ethanone (cis):

$^1$H-NMR (400 MHz, CDCl$_3$): δ5.69 (dquint, J=2.6, 10.0, 1 H), 5.45 (dm, J=10.0, 1 H), 2.64 (d, J=6.3, H—C(6')), 2.57-2.48 (m, H—C(7')), 2.16 (s, MeCO), 2.10 (dm, J=17.9, 1 H), 1.82 (dm, J=17.9, 1 H), 1.72-1.28 (m, 8 H), 0.99 (d, J=7.6, MeC(7')).

$^{13}$C-NMR (100 MHz, CDCl$_3$): δ211.97 (s, CO), 129.57 (d, C(8')), 125.89 (d, C(9')), 60.48 (d, C(6')), 43.69 (s, C(5')), 38.86 (t), 38.61 (t), 34.06 (q, MeCO), 33.44 (t), 32.49 (d, C(7')), 23.97 (t), 23.39 (t), 17.59 (q).

MS (EI): 192 (14), 177 (6), 174 (4), 159 (3), 150 (13), 149 (100), 134 (21), 119 (16), 109 (17), 108 (27), 107 (29), 105 (24), 98 (25), 95 (22), 93 (41), 91 (43), 81 (51), 79 (35), 77 (22), 67 (26), 55 (14), 43 (50), 41 (19), 39 (11).

Data of 1-(rel-(6S,7R)-7-methylspiro[4.5]dec-8-en-6-yl)ethanone (trans):

$^1$H-NMR (400 MHz, CDCl$_3$): δ5.55 (dm, J=10.2, 1 H), 5.49 (br. d, J=10.5, 1 H), 2.56-2.48 (m, H—C(7'), H—C(6')), 2.22 (s, MeCO), 1.96 (br. dd, J=4.8, 17.6, 1 H), 1.91-1.81 (m, 2 H), 1.67-1.36 (m, 7 H), 0.91 (d, J=6.6, MeC(T)).

$^{13}$C-NMR (100 MHz, CDCl$_3$): δ213.73 (s, CO), 132.74 (d, C(8')), 124.42 (d, C(9')), 61.35 (d, C(6')), 44.79 (s, C(5')), 39.08 (t), 38.35 (t), 35.02 (q, MeCO), 32.79 (d, C(7')), 29.78 (t), 24.25 (t), 23.44 (t), 19.96 (q).

$^1$H-NMR (400 MHz, C$_6$D$_6$): δ5.49-5.40 (m, H—C(8'), H—C(9')), 2.69-2.57 (m, H—C(7')), 2.25 (d, J=10.1, H—C(6')), 2.23-2.13 (m, 1 H), 1.86 (s, MeCO), 1.75 (dm, J=17.4, 1 H), 1.64 (dsext., J=2.0, 17.4, 1 H), 1.59-1.29 (m, 6 H), 1.18-1.10 (m, 1 H), 0.79 (d, J=7.1, MeC(7')).

$^{13}$C-NMR (100 MHz, C$_6$D$_6$): δ211.18 (s, CO), 132.95 (d, C(8')), 124.36 (d, C(9')), 60.81 (d, C(6')), 44.75 (s, C(5')), 39.22 (t), 38.40 (t), 34.60 (q, MeCO), 32.92 (d, C(7')), 29.83 (t), 24.49 (t), 23.69 (t), 19.77 (q).

MS (EI): 192 (15), 177 (2), 174 (2), 159 (1), 150 (12), 149 (100), 134 (14), 119 (13), 107 (21), 105 (17), 93 (26), 91 (26), 81 (48), 79 (23), 77 (14), 67 (21), 55 (10), 43 (35), 41 (13), 39 (7).

c) (E)-1-(rel-(6S,7R)-7-Methylspiro[4.5]dec-8-en-6-yl)but-2-en-1-one and (E)-1-(rel-(6R,7R)-7-methylspiro[4.5]dec-8-en-6-yl)but-2-en-1-one At −70° C., a solution of diisopropylamine (49.7 ml, 352 mmol) in tetrahydrofuran (200 ml) was treated with n-butyl lithium (224 ml, 1.6M in hexane, 358 mmol). The resulting solution was warmed to −30° C., cooled to −78° C., and treated with a solution of a 83:17 mixture of 1-(rel-(6S,7R)-7-methylspiro[4.5]dec-8-en-6-yl)ethanone and 1-(rel-(6R,7R)-7-methylspiro[4.5]dec-8-en-6-yl)ethanone (56.4 g, 290 mmol) in tetrahydrofuran (150 ml). The resulting solution was stirred 20 min. at −70° C. and treated within 50 min. with a solution of acetaldehyde (82.8 ml, 1.47 mol) in tetrahydrofuran (100 ml). After 45 min. stirring, the reaction mixture was poured into an ice-cold saturated aqueous solution of NH$_4$Cl (400 ml) and extracted twice with MTBE (300 ml). The combined organic phases were washed with water (150 ml) and with a saturated aqueous solution of NaCl (250 ml), dried (MgSO$_4$), and concentrated giving the desired intermediate β-hydroxyketones as diasteromeric mixture (75.7 g) which was dissolved in acetic anhydride (58.2 ml, 616 mmol) and treated with sodium acetate (36.1 g, 440 mmol). The resulting mixture was heated at 80° C. for 19 h, cooled to 20° C., poured into water and ice (400 ml), and extracted three times with MTBE (300 ml). The combined organic phases were washed three times with 2N aqueous NaOH solution, twice with a saturated aqueous solution of NaCl, dried (MgSO$_4$), and concentrated. Short-path distillation (bath temperature 60 to 180° C., head temperature 70-115° C., 0.09 mbar) of the crude product (87 g) over K$_2$CO$_3$ (1 g) gave a diastereomeric mixture of the desired butenones (50.5 g, 79%, rel-(6S,7R)/rel-(6R,7R) 80:20).

Data of (E)-1-(rel-(6S,7R)-7-methylspiro[4.5]dec-8-en-6-yl)but-2-en-1-one (Boiling point: 114° C. (0.13 mbar))

$^1$H-NMR (400 MHz, CDCl$_3$): δ6.83 (dq, J=6.8, 15.7, H—C(3)), 6.23 (dq, J=1.7, 15.5, H—C(2)), 5.58-5.50 (m, H—C(8'), H—C(9')), 2.72 (d, J=10.4, H—C(6')), 2.66-2.56 (m, H—C(7')), 2.00-1.85 (m, 3 H), 1.90 (dd, J=1.6, 6.9, MeC(3)), 1.62-1.45 (m, 4 H), 1.45-1.36 (m, 2 H), 1.34-1.25 (m, 1 H), 0.86 (d, J=7.1, MeC(7')).

$^{13}$C-NMR (100 MHz, CDCl$_3$): δ204.31 (s, CO), 141.70 (d, C(3)), 135.01 (d, C(2)), 133.16 (d, C(8')), 124.32 (d, C(9')), 57.88 (d, C(6')), 45.11 (s, C(5')), 39.50 (t), 38.37 (t), 32.62 (d, C(7')), 30.02 (t), 24.39 (t), 23.62 (t), 19.96 (q), 18.22 (q).

MS (EI): 218 (9), 203 (2), 149 (43), 135 (12), 134 (26), 121 (9), 119 (17), 107 (15), 106 (11), 105 (18), 93 (18), 91 (26), 81 (33), 79 (20), 77 (15), 69 (100), 55 (14), 41 (41), 39 (15).

Odour description: Damascone-like, fruity, floral.

Data of (E)-1-(rel-(6R,7R)-7-methylspiro[4.5]dec-8-en-6-yl)but-2-en-1-one (Boiling point: 110° C. (0.08 mbar))

$^1$H-NMR (400 MHz, CDCl$_3$): δ6.79 (dq, J=6.8, 15.6, H—C(3)), 6.22 (dq, J=1.7, 15.5, H—C(2)), 5.70 (dquint, J=2.5, 10.1, H—C(8'/9')), 5.48 (dm, J=10.1, H—C(9'/8')), 2.71 (d, J=6.1, H—C(6')), 2.60-2.50 (m, H—C(7')), 2.13 (dm, J=17.7, 1H), 1.87 (dd, J=1.8, 6.8, MeC(3)), 1.81 (dm, J=17.8, 1H), 1.71-1.55 (m, 5 H), 1.47-1.32 (m, 2 H), 1.31-1.23 (m, 1 H), 0.94 (d, J=7.6, MeC(7')).

$^{13}$C-NMR (100 MHz, CDCl$_3$): δ202.58 (s, CO), 141.28 (d, C(3)), 134.19 (d, C(2)), 130.15 (d, C(8')), 125.92 (d, C(9')), 57.38 (d, C(6')), 44.12 (s, C(5')), 39.01 (t), 38.55 (t), 33.81 (t), 31.17 (d, C(7')), 24.06 (t), 23.24 (t), 18.14 (q), 17.76 (q).

MS (EI): 218 (10), 203 (5), 189 (5), 149 (43), 135 (17), 134 (31), 124 (14), 123 (15), 122 (12), 121 (16), 119 (19), 109 (30), 107 (22), 106 (12), 105 (24), 93 (28), 91 (37), 81 (40), 79 (28), 77 (20), 69 (100), 55 (19), 41 (61), 39 (23).

Odour description: fruity, earthy, agrestic, green.

d) (E)-1-(rel-(6S,7R)-7-Methylspiro[4.5]dec-8-en-6-yl)but-2-en-1-one

At −70° C., a solution of diisopropylamine (0.5 g, 4.93 mmol) in tetrahydrofuran (4 ml) was treated with n-butyl lithium (3.3 ml, 1.6M in hexane, 5.14 mmol). The resulting solution was stirred at −70° C. for 20 min. and treated with a solution of 1-(rel-(6S,7R)-7-methylspiro[4.5]dec-8-en-6-yl)ethanone (0.79 g, 4.11 mmol) in tetrahydrofuran (4 ml). The resulting solution was stirred 20 min. at −70° C. warmed to 0° C., cooled to −70° C., and treated with a solution of acetaldehyde (0.9 g, 20.5 mmol) in tetrahydrofuran (4 ml). After 20 min. stirring, the reaction mixture was warmed to −5° C., treated with a 1:1 mixture of a 2N aqueous HCl solution and saturated aqueous NaCl solution (25 ml) and extracted three times with MTBE (60 ml). The combined organic phases were washed with a saturated solution of $NaHCO_3$, with a saturated solution of $NH_4Cl$, and with water, dried ($MgSO_4$), and concentrated. Fluid chromatography (FC, $SiO_2$, hexane/MTBE 35:1) of the crude product (1.3 g) gave the desired intermediate β-hydroxyketone (0.47 g, 1.98 mmol, 48%) which was dissolved in cyclohexane (1 ml). The resulting solution was treated with para-toluene sulfonic acid monohydrate (13 mg, 6.7 mmol) and refluxed 1.5 h. The reaction mixture was cooled to 0° C., treated with a saturated aqueous solution of $NaHCO_3$ and the aqueous phase was extracted twice with MTBE. The combined organic phases were washed with water, dried ($MgSO_4$) and concentrated. FC ($SiO_2$, hexane/MTBE 50:1) of the crude product (0.42 g) gave (E)-1-(rel-(6S,7R)-7-Methylspiro[4.5]dec-8-en-6-yl)but-2-en-1-one (0.34 g, 79%).

e) (E)-1-(rel-(6R,7R)-7-methylspiro[4.5]dec-8-en-6-yl)but-2-en-1-one

FC (200 g $SiO_2$, hexane/MTBE 30:1) of a crude 30:70 mixture of (E)-1-(rel-(6S,7R)-7-methylspiro[4.5]dec-8-en-6-yl)but-2-en-1-one and (E)-1-(rel-(6R,7R)-7-methylspiro[4.5]dec-8-en-6-yl)but-2-en-1-one (1.51 g) gave (E)-1-(rel-(6S,7R)-7-methylspiro[4.5]dec-8-en-6-yl)but-2-en-1-one (0.24 g, 16%) and (E)-1-(rel-(6R,7R)-7-methylspiro[4.5]dec-8-en-6-yl)but-2-en-1-one (0.48 g, 32%).

Example 2 rel-(6S,7R)-Methyl 7-methylspiro[4.5]dec-8-ene-6-carboxylate and rel-(6R,7R)-methyl 7-methylspiro[4.5]dec-8-ene-6-carboxylate In an autoclave, a mixture of 3,3,15-trimethyl-2,4-dioxadispiro[5.0.4.4]pentadec-13-ene-1,5-dione (100 g, 78% pure, 280 mmol) and copper powder (1.37 g, 21 mmol) in methanol (44.9 g, 1.4 mol) and pyridine (360 ml) was heated at 135° C. for 48 h. The resulting mixture was concentrated and the residue poured into a mixture of 2N aqueous HCl and ice and extracted three times with methyl-tert-butyl ether (MTBE, 250 ml). The combined organic phases were washed with a saturated aqueous NaCl solution, dried ($MgSO_4$), and concentrated. Short-path distillation (bath temperature 110° C., head temperature: 60-80° C., 0.1 mbar) of the crude product (81 g) gave a diastereomeric mixture of the desired methyl ester (48.9 g, 84%, rel-(6S,7R)/rel-(6R,7R) 30:70). Boiling point: 80° C. (0.12 mbar).

Odour description: fruity, floral, agrestic, Damascone-like

Data of rel-(6S,7R)-methyl 7-methylspiro[4.5]dec-8-ene-6-carboxylate $^1$H-NMR (400 MHz, $CDCl_3$): selected signals: δ5.55 (dquint, J=2.4, 10.1, 1 H), 5.50 (dm, J=10.1, 1 H), 3.68 (s, MeO), 2.60-2.49 (m, H—C(7')), 2.25 (d, J=10.6, H—C(6')), 2.00-1.83 (m, 3 H), 1.68-1.30 (m, 7 H), 0.94 (d, J=6.8, MeC(7')).
$^{13}$C-NMR (100 MHz, $CDCl_3$): δ175.49 (s, CO), 132.15 (d), 124.69 (d), 56.00 (d, C(6')), 51.09 (q, OMe), 43.97 (s, C(5')), 39.62 (t), 38.54 (t), 32.43 (d, C(7')), 30.47 (t), 24.87 (t), 24.44 (t), 19.95 (q).
MS (EI): 208 (8), 193 (2), 177 (5), 176 (12), 149 (74), 148 (100), 141 (9), 133 (16), 119 (18), 107 (33), 106 (47), 105 (39), 93 (41), 91 (61), 81 (46), 79 (49), 77 (33), 68 (30), 67 (55), 59 (15), 57 (7), 55 (23), 41 (41).

Data of rel-(6R,7R)-methyl 7-methylspiro[4.5]dec-8-ene-6-carboxylate $^1$H-NMR (400 MHz, $CDCl_3$): δ5.69 (dquint, J=2.5, 10.1, 1 H), 5.42 (dm, J=10.1, 1 H), 3.62 (s, MeO), 2.57-2.47 (m, H—C(7')), 2.43 (d, J=6.3, H—C(6')), 2.25 (dm, J=17.7, 1 H), 1.81 (ddq, J=1.6, 5.1, 17.7, 1 H), 1.71-1.61 (m, 4 H), 1.60-1.52 (m, 1 H), 1.52-1.43 (m, 1 H), 1.39-1.28 (m, 2 H), 0.99 (d, J=7.3, MeC(7')).
$^{13}$C-NMR (100 MHz, $CDCl_3$): δ173.84 (s, CO), 129.13 (d), 125.97 (d), 54.05 (d, C(6')), 50.64 (q, OMe), 43.44 (s, C(5')), 38.87 (t), 38.38 (t), 33.78 (t), 30.50 (d, C(7')), 24.00 (t), 23.73 (t), 17.79 (q).
MS (EI): 208 (6), 193 (1), 177 (6), 176 (22), 149 (89), 148 (100), 141 (9), 133 (29), 119 (24), 107 (41), 106 (60), 105 (52), 93 (54), 91 (75), 81 (40), 79 (49), 77 (35), 68 (28), 67 (48), 59 (15), 57 (12), 55 (25), 41 (40).

Example 3 rel-(6S,7R)-Ethyl 7-methylspiro[4.5]dec-8-ene-6-carboxylate and rel-(6R,7R)-ethyl 7-methylspiro[4.5]dec-8-ene-6-carboxylate In an autoclave, a mixture of 3,3,15-trimethyl-2,4-dioxadispiro[5.0.4.4]pentadec-13-ene-1,5-dione (3 g, 10.8 mmol) and copper powder (53 mg, 0.83 mmol) in ethanol (3.6 ml, 61.7 mmol) and pyridine (22 ml) was heated at 120° C. for 37 h. The resulting mixture was poured into a mixture of 2N aqueous HCl and ice and extracted three times with MTBE. The combined organic phases were washed with a saturated aqueous NaCl solution, dried ($MgSO_4$), and concentrated. Ball-to-ball distillation (120° C., 0.1 mbar) of the crude product (2.3 g) gave a diastereomeric mixture of the desired ethyl ester (1.65 g, 69%, rel-(6S,7R)/rel-(6R,7R) 26:74). Boiling point: 87° C. (0.13 mbar).

Odour description: Damascone-like, fruity, plum, floral, slightly agrestic

Data of rel-(6S,7R)-ethyl 7-methylspiro[4.5]dec-8-ene-6-carboxylate $^1$H-NMR (400 MHz, $CDCl_3$): selected signals: 85.55 (dquint, J=2.4, 10.1, 1 H), 5.42 (dm, J=10.1, 1 H), 4.19-4.08 (m, $CH_2$O), 2.57-2.43 (m, H—C(7')), 2.22 (d, J=10.4, H—C(6')), 1.28 (t, J=7.1, $MeCH_2$O), 0.95 (d, J=6.8, MeC(T)).
$^{13}$C-NMR (100 MHz, $CDCl_3$): δ174.99 (s, CO), 132.21 (d), 124.65 (d), 59.83 (t, $OCH_2$), 55.99 (d, C(6')), 43.94 (s, C(5')), 39.74 (t), 38.40 (t), 32.42 (d, C(7')), 30.50 (t), 24.94 (t), 24.51 (t), 19.86 (q), 14.38 (q).
MS (EI): 222 (11), 207 (1), 193 (1), 177 (8), 176 (9), 149 (79), 148 (100), 141 (13), 139 (9), 134 (16), 133 (14), 119 (16), 107 (25), 106 (43), 105 (33), 93 (30), 91 (40), 81 (37), 79 (32), 77 (20), 73 (1), 67 (32), 55 (15), 45 (1), 41 (21).

Data of rel-(6R,7R)-ethyl 7-methylspiro[4.5]dec-8-ene-6-carboxylate $^1$H-NMR (400 MHz, $CDCl_3$): δ5.68 (dquint, J=2.5, 10.1, 1 H), 5.42 (dm, J=10.1, 1 H), 4.17-4.04 (m, $CH_2$O), 2.58-2.46 (m, H—C(7')), 2.40 (d, J=6.3, H—C(6')), 2.25 (dm, J=17.9, 1 H), 1.80 (ddq, J=1.7, 5.1, 17.7, 1 H), 1.70-1.62 (m, 4 H), 1.60-1.46 (m, 2 H), 1.40-1.28 (m, 2 H), 1.24 (t, J=7.1, $MeCH_2$O), 1.00 (d, J=7.6, MeC(7')).

$^{13}$C-NMR (100 MHz, CDCl$_3$): δ173.27 (s, CO), 129.19 (d), 125.87 (d), 59.39 (t, OCH$_2$), 54.07 (d, C(6')), 43.47 (s, C(5')), 38.76 (t), 38.40 (t), 33.82 (t), 30.52 (d, C(7')), 24.00 (t), 23.71 (t), 17.73 (q), 14.38 (q).

MS (EI): 222 (9), 207 (1), 193 (1), 177 (9), 176 (24), 149 (91), 148 (100), 134 (10), 133 (30), 119 (21), 107 (30), 106 (55), 105 (45), 93 (39), 91 (53), 81 (31), 79 (34), 77 (22), 73 (1), 67 (27), 55 (14), 45 (1), 41 (18).

Example 4 rel-(6S,7R)-Allyl 7-methylspiro[4.5]dec-8-ene-6-carboxylate and rel-(6R,7R)-allyl 7-methylspiro[4.5]dec-8-ene-6-carboxylate In an autoclave, a mixture of 3,3,15-trimethyl-2,4-dioxadispiro[5.0.4.4]-pentadec-13-ene-1,5-dione (3 g, 10.8 mmol) and copper powder (53 mg, 0.83 mmol) in allyl alcohol (4.2 ml, 61.4 mmol) and pyridine (22 ml) was heated at 135° C. for 44 h. The resulting mixture was poured into a mixture of 2N aqueous HCl and ice and extracted three times with MTBE. The combined organic phases were washed twice with a saturated aqueous NaCl solution, dried (MgSO$_4$), and concentrated. FC (SiO$_2$, hexane/MTBE 40:1) of the crude product (2.41 g) gave a diastereomeric mixture of the desired allyl ester (1.49 g, 60%, rel-(6S,7R)/rel-(6R,7R) 31:69). Boiling point: 76° C. (0.1 mbar).

Odour description: floral, woody, fruity, rosy, agrestic

Data of rel-(6S,7R)-methyl 7-methylspiro[4.5]decane-6-carboxylate $^1$H-NMR (400 MHz, CDCl$_3$): selected signals: δ5.93 (ddt, J=5.8, 10.6, 17.2, 1 H), 5.55 (dquint, J=2.4, 9.9, 1 H), 5.50 (dm, J=10.1, 1 H), 5.34 (dq, J=1.6, 17.3, 1 H), 5.24 (dq, J=1.3, 10.6, 1 H), 4.60 (dtd, J=1.3, 4.5, 5.8, CH$_2$O), 2.27 (d, J=10.4, H—C(6')), 0.95 (d, J=6.8, MeC(7')).

$^{13}$C-NMR (100 MHz, CDCl$_3$): δ174.67 (s, CO), 132.38 (d), 132.15 (d), 124.68 (d), 118.28 (t), 64.70 (t, OCH$_2$), 56.01 (d, C(6')), 43.99 (s, C(5')), 39.68 (t), 38.44 (t), 32.49 (d, C(7')), 30.54 (t), 24.91 (t), 24.48 (t), 19.91 (q).

MS (EI): 234 (2), 193 (18), 177 (1), 176 (2), 165 (10), 149 (20), 148 (27), 147 (100), 133 (9), 119 (8), 107 (12), 106 (14), 105 (32), 93 (17), 91 (26), 81 (23), 79 (21), 77 (13), 74 (1), 67 (18), 55 (10), 41 (25).

Data of rel-(6R,7R)-methyl 7-methylspiro[4.5]decane-6-carboxylate $^1$H-NMR (400 MHz, CDCl$_3$): selected signals: δ5.92 (ddt, J=5.8, 10.4, 17.2, 1 H), 5.68 (dquint, J=2.5, 10.1, 1 H), 5.43 (dm, J=10.2, 1 H), 5.32 (dq, J=1.5, 17.2, 1 H), 5.21 (dq, J=1.4, 10.4, 1 H), 4.55 (dtd, J=0.5, 1.3, 5.8, CH$_2$O), 2.61-2.48 (m, H—C(7')), 2.45 (d, J=6.6, H—C(6')), 1.01 (d, J=7.6, MeC(7')).

$^{13}$C-NMR (100 MHz, CDCl$_3$): δ172.95 (s, CO), 132.52 (d), 129.17 (d), 125.90 (d), 118.01 (t), 64.30 (t, OCH$_2$), 55.12 (d, C(6')), 43.52 (s, C(5')), 38.84 (t), 38.40 (t), 33.79 (t), 30.58 (d, C(7')), 23.99 (t), 23.69 (t), 17.80 (q).

MS (EI): 234 (6), 193 (7), 177 (5), 176 (22), 165 (7), 149 (37), 148 (63), 147 (100), 133 (21), 119 (16), 107 (20), 106 (36), 105 (52), 93 (27), 91 (46), 81 (29), 79 (29), 77 (19), 74 (1), 67 (23), 55 (15), 41 (34).

Example 5 rel-(6S,7R)-Methyl 7-methylspiro[4.5]decane-6-carboxylate and rel-(6R,7R)-methyl 7-methylspiro[4.5]decane-6-carboxylate A solution of a 25:75 mixture of rel-(6S,7R)-methyl 7-methylspiro[4.5]dec-8-ene-6-carboxylate and rel-(6R,7R)-methyl 7-methylspiro[4.5]dec-8-ene-6-carboxylate (1.1 g, 5.28 mmol) in ethanol (10 ml) was treated with 10% Pd/C (0.1 g) and hydrogenated (1 atm.) for 1.5 h. The resulting mixture was filtered and concentrated. FC (SiO$_2$, hexane/MTBE 80:1) of the crude product (1.1 g) gave a diastereomeric mixture of the desired ester (0.82 g, 74%, rel-(6S,7R)/rel-(6R,7R) 30:70). Boiling point: 76° C. (0.1 mbar).

Odour description: agrestic, fruity-floral, woody.

Data of rel-(6S,7R)-methyl 7-methylspiro[4.5]decane-6-carboxylate $^1$H-NMR (400 MHz, CDCl$_3$): selected signals: 83.65 (s, CH$_3$O), 2.00 (d, J=11.1, H—C(6')), 2.06-1.99 (m, 1 H), 0.82 (d, J=6.3, MeC(7')).

$^{13}$C-NMR (100 MHz, CDCl$_3$): δ175.34 (s, CO), 59.63 (d, C(6')), 50.84 (q, MeO), 45.12 (s, C(5')), 40.03 (t), 39.81 (t), 34.26 (t), 33.00 (d, C(7')), 29.96 (t), 25.84 (t), 24.70 (t), 22.46 (t), 20.78 (q).

MS (EI): 210 (6), 195 (1), 192 (1), 179 (14), 178 (80), 151 (15), 141 (4), 136 (40), 134 to (25), 129 (29), 121 (18), 115 (6), 109 (30), 108 (21), 107 (24), 101 (62), 96 (62), 95 (94), 94 (38), 93 (40), 82 (47), 81 (88), 79 (48), 77 (24), 74 (13), 69 (47), 67 (100), 59 (22), 55 (62), 41 (69), 29 (13).

Data of rel-(6R,7R)-methyl 7-methylspiro[4.5]decane-6-carboxylate $^1$H-NMR (400 MHz, CDCl$_3$): selected signals: 83.62 (s, CH$_3$O), 2.30 (d, J=5.1, H—C(6')), 1.86 (tdd, J=0.9, 4.0, 13.4, 1 H), 0.87 (d, J=6.8, MeC(7')).

$^{13}$C-NMR (100 MHz, CDCl$_3$): δ174.62 (s, CO), 55.84 (d, C(6')), 50.40 (q, MeO), 44.80 (s, C(5')), 39.61 (t), 36.55 (t), 31.66 (t), 31.36 (d, C(7')), 28.81 (t), 24.32 (t), 23.74 (t), 22.64 (t), 20.24 (q).

MS (EI): 210 (7), 195 (1), 179 (14), 178 (79), 151 (21), 141 (32), 136 (48), 134 (20), 129 (25), 121 (19), 115 (13), 109 (42), 108 (25), 107 (25), 101 (50), 96 (58), 95 (100), 94 (36), 93 (50), 82 (40), 81 (92), 79 (49), 77 (26), 74 (11), 69 (40), 67 (92), 59 (22), 55 (66), 41 (70), 29 (14).

Example 6 rel-(6S,7R)-Ethyl 7-methylspiro[4.5]decane-6-carboxylate and rel-(6R,7R)-ethyl 7-methylspiro[4.5]decane-6-carboxylate A solution of a 1:2 mixture of rel-(6S,7R)-ethyl 7-methylspiro[4.5]dec-8-ene-6-carboxylate and rel-(6R,7R)-ethyl 7-methylspiro[4.5]dec-8-ene-6-carboxylate (3.3 g, 16 mmol) in ethanol (30 ml) was treated with 10% Pd/C (0.4 g) and hydrogenated (20 bar) for 1.5 h. The resulting mixture was filtered and concentrated. FC (SiO$_2$, hexane/MTBE 30:1) of the crude product (3.1 g) gave a diastereomeric mixture of the desired ester (2.90 g, 87%, rel-(6S,7R)/rel-(6R,7R) 1:2). Boiling point: 90° C. (0.07 mbar).

Odour description: Damascone-like, fruity, floral, agrestic.

Data of rel-(6S,7R)-ethyl 7-methylspiro[4.5]decane-6-carboxylate $^1$H-NMR (400 MHz, CDCl$_3$): selected signals: δ4.12 (qd, J=1.26, 7.1, CH$_2$O), 2.06-1.99 (m, 1 H), 1.98 (d, J=11.2, H—C(6')), 1.26 (t, J=7.2, MeCH$_2$O), 0.83 (d, J=6.2, MeC(7')).

$^{13}$C-NMR (100 MHz, CDCl$_3$): δ174.84 (s, CO), 59.61 (d, C(6')), 59.22 (t, CH$_2$O), 45.12 (s, C(5')), 39.91 (t), 39.87 (t), 34.31 (t), 32.11 (d, C(7')), 29.98 (t), 25.91 (t), 24.75 (t), 22.48 (t), 20.70 (q), 14.34 (q).

MS (EI): 224 (7), 209 (1), 195 (1), 179 (23), 178 (100), 160 (8), 155 (3), 151 (30), 143 (25), 136 (45), 134 (26), 127 (4), 121 (18), 115 (42), 109 (35), 108 (21), 107 (22), 96 (61), 95 (98), 94 (39), 93 (36), 88 (16), 87 (47), 81 (92), 79 (40), 77 (20), 69 (34), 67 (84), 55 (54), 41 (58), 29 (32).

Data of rel-(6R,7R)-ethyl 7-methylspiro[4.5]decane-6-carboxylate $^1$H-NMR (400 MHz, CDCl$_3$): selected signals:δ4.11 (q, J=7.1, CH$_2$O), 2.27 (d, J=4.8, H—C(6')), 1.87 (tdd, J=0.8, 4.2, 13.1, 1 H), 1.26 (t, J=7.8, MeCH$_2$O), 0.87 (d, J=6.8, MeC(7')).

$^{13}$C-NMR (100 MHz, CDCl$_3$): δ174.13 (s, CO), 59.22 (t, CH$_2$O), 55.89 (d, C(6')), 44.84 (s, C(5')), 39.51 (t), 36.59 (t), 31.71 (t), 31.39 (d, C(7')), 28.88 (t), 24.30 (t), 23.74 (t), 22.66 (t), 20.18 (q), 14.44 (q).

MS (EI): 224 (7), 209 (1), 195 (2), 179 (21), 178 (95), 160 (7), 155 (28), 151 (37), 143 (20), 136 (56), 134 (20), 127 (22), 121 (19), 115 (34), 109 (36), 108 (22), 107 (21), 96 (54), 95 (100), 94 (33), 93 (38), 88 (12), 87 (34), 81 (87), 79 (39), 77 (20), 69 (29), 67 (71), 55 (52), 41 (52), 29 (30).

Example 7

1-(rel-(6S,7R)-7-Methylspiro[4.5]decan-6-yl)butan-1-one

A solution of (E)-1-(rel-(6S,7R)-7-methylspiro[4.5]dec-8-en-6-yl)but-2-en-1-one (2.0 g, 9.16 mmol) in ethanol (30 ml) was treated with 10% Pd/C (0.4 g) and hydrogenated (20 bar) for 1.5 h. The resulting mixture was filtered and concentrated. FC (SiO$_2$, hexane/MTBE 50:1) of the crude product (1.9 g) gave 1-(rel-(6S,7R)-7-methylspiro[4.5]decan-6-yl)butan-1-one (0.75 g, 37%). Boiling point: 95° C. (0.08 mbar).

Odour description: fruity, floral, woody, Damascone-like.

$^1$H-NMR (400 MHz, CDCl$_3$): δ2.51 (ddd, J=6.4, 8.3, 17.9, 1H), 2.33 (ddd, J=6.1, 8.3, 17.9, 1H), 2.24 (d, J=10.9, H—C(6')), 2.10-2.00 (m, 1 H), 1.80-1.28 (m, 14 H), 1.17-1.05 (m, 1 H), 0.99-0.83 (m, 1 H), 0.91 (t, J=7.4, MeC(3)), 0.75 (d, J=6.3, MeC(7')).

$^{13}$C-NMR (100 MHz, CDCl$_3$): δ215.66 (s, CO), 64.48 (d, C(6')), 50.53 (t), 46.11 (s, C(5')), 40.15 (t), 39.53 (t), 34.82 (t), 32.69 (d, C(7')), 29.07 (t), 25.08 (t), 24.29 (t), 22.35 (t), 20.75 (q), 16.45 (t), 13.75 (q).

MS (EI): 222 (2), 204 (20), 189 (1), 179 (10), 151 (37), 136 (26), 126 (6), 121 (8), 113 (24), 109 (25), 95 (100), 83 (17), 81 (35), 71 (28), 69 (20), 67 (25), 55 (27), 43 (34), 41 (31).

Example 8

1-(rel-(6S,7R)-7-Methylspiro[4.5]dec-8-en-6-yl)butan-1-one

After argon bubbling, a mixture of benzene (70 ml) and water (0.15 ml) was treated with triphenylphosphine-cooper (I)-hydride hexamer (3.3 g, 1.68 mmol). The resulting mixture was stirred for five min., treated with a solution of (E)-1-(rel-(6S,7R)-7-methylspiro[4.5]dec-8-en-6-yl)but-2-en-1-one (2 g, 9.16 mmol) in benzene (10 ml) and stirred for 2 h at 20° C. The reaction mixture was then stirred for 30 min under air, filtered, and concentrated. FC (SiO$_2$, hexane/MTBE 70:1) of the crude product (4.07 g) gave 1-(rel-(6S,7R)-7-methylspiro[4.5]dec-8-en-6-yl)butan-1-one (0.80 g, 40%). Boiling point: 100° C. (0.08 mbar).

Odour description: floral, fruity, slightly woody, Damascone-like.

$^1$H-NMR (400 MHz, CDCl$_3$): δ5.54 (dquint, J=2.0, 10.0, 1 H), 5.49 (dm, J=10.0, 1 H), 2.54 (ddd, J=6.4, 8.3, 17.7, 1H), 2.58-2.48 (m, H—C(7')), 2.48 (d, J=10.1, H—C(6')), 2.36 (ddd, J=6.1, 8.3, 17.7, 1H), 1.99-1.88 (m, 2 H), 1.84 (dsext, J=1.8, 17.7, 1 H), 1.67-1.33 (m, 9 H), 0.92 (t, J=7.4, MeC(3)), 0.88 (d, J=6.6, MeC(7')).

$^{13}$C-NMR (100 MHz, CDCl$_3$): δ215.30 (s, CO), 132.96 (d, C(3)), 124.42 (d, C(2)), 60.55 (d, C(6')), 49.99 (t), 45.00 (s, C(5')), 39.03 (t), 38.25 (t), 32.83 (d, C(7')), 29.76 (t), 24.20 (t), 23.34 (t), 20.00 (q), 16.49 (t), 13.77 (q).

MS (EI): 220 (5), 205 (1), 191 (1), 177 (3), 149 (100), 134 (14), 126 (4), 119 (10), 109 (9), 107 (17), 106 (10), 105 (14), 93 (22), 91 (22), 81 (45), 71 (51), 67 (16), 55 (11), 43 (36), 41 (23).

Example 9

(E)-1-(rel-(6R,7R)-7-Methylspiro[4.5]decan-6-yl)but-2-en-1-one

A solution of 3,3,15-trimethyl-2,4-dioxadispiro[5.0.4.4]pentadec-13-ene-1,5-dione (11.3 g, 28 mmol) in ethanol (50 ml) was treated with 10% Pd/C (1.1 g) and hydrogenated (20 bar) for 1.5 h. The resulting mixture was filtered and concentrated. The crude 3,3,15-trimethyl-2,4-dioxadispiro[5.0.4.4]pentadecane-1,5-dione (10 g) was dissolved in THF (100 ml) and treated at −20° C. within 15 min. with methyllithium (45 ml, 1.6M in diethyl ether, 71 mmol). The resulting solution was refluxed for 3 h, treated with methyllithium (10 ml, 1.6M in diethyl ether, 16 mmol), refluxed for 1 h, cooled, poured into a mixture of 2N aqueous NaOH and ice (300 ml), and extracted twice with methyl-tert-butyl ether (MTBE, 80 ml). The combined organic phases were washed with 2M aqueous NaOH (50 ml) and the aqueous phases were combined, acidified with conc. HCl to pH1 and extracted twice with MTBE (100 ml). The resulting organic phases were combined, washed with water, with a saturated aqueous solution of NaCl, dried (MgSO$_4$), and concentrated giving the crude intermediate ketoacid (7 g) which was refluxed in pyridine (70 ml) during 4 h. The resulting mixture was poured into 2N aqueous HCl and ice (300 ml), and extracted twice with cyclohexane (100 ml). The combined organic phases were washed with 2M aqueous HCl (50 ml), with water (50 ml), with a saturated aqueous solution of NaCl (100 ml), dried (16 g MgSO$_4$), and concentrated to give the crude 1-(rel-(6R,7R)-7-methylspiro[4.5]decan-6-yl)ethanone (4.44 g, 56%).

¹H-NMR (400 MHz, CDCl₃): selected signals: δ2.60 (br. d, J=4.0, H—C(6')), 2.15 (s, MeCO), 1.85 (br. td, J=3.6, 13.1, 1 H), 1.83-1.72 (m, 1 H), 1.17 (dm, J=12.7, 1 H), 0.81 (d, J=6.9, MeC(7I).

¹³C-NMR (100 MHz, CDCl₃): δ213.54 (s, CO), 60.95 (d, C(6')), 45.51 (s, C(5')), 39.21 (t), 36.62 (t), 36.39 (q, MeCO), 32.20 (d), 31.16 (t), 28.59 (t), 23.87 (t), 23.80 (t), 22.54 (t), 20.35 (q).

MS (EI): 194 (5), 180 (1), 179 (3), 161 (6), 147 (8), 136 (46), 125 (51), 121 (13), 109 (27), 95 (100), 85 (30), 81 (39), 67 (41), 55 (35), 43 (74), 41 (33).

At −60° C., a solution of diisopropylamine (4.1 ml, 28.8 mmol) in tetrahydrofuran (30 ml) was treated with n-butyl lithium (18 ml, 1.6M in hexane, 28.8 mmol). The resulting solution was stirred at −30° C. for 20 min., cooled to −70° C., and treated with a solution of crude 1-(rel-(6R,7R)-7-methylspiro[4.5]decan-6-yl)ethanone (4.3 g, 22 mmol) in tetrahydrofuran (10 ml). The resulting solution was stirred 45 min. at −70° C., and treated within 15 min. with a solution of acetaldehyde (5 ml, 88.5 mmol) in tetrahydrofuran (10 ml). After 2 h stirring, the reaction mixture was poured into 2N aqueous HCl and ice (150 ml) and extracted twice with MTBE (100 ml). The combined organic phases were washed with water (50 ml), with a saturated aqueous NaCl solution (100 ml), dried (MgSO₄), and concentrated. The crude product (5.5 g) was dissolved in toluene (60 ml). The resulting solution was treated with para-toluene sulfonic acid monohydrate (0.5 g, 2.8 mmol) and heated at 60° C. for 1.5 h. The reaction mixture was cooled, poured into a cold saturated aqueous solution of NaHCO₃ (100 ml) and the aqueous phase was extracted with MTBE (80 ml). The combined organic phases were washed with a saturated aqueous NaCl solution (80 ml), dried (MgSO₄) and concentrated. FC (SiO₂, hexane/MTBE 30:1) of the crude product (5.5 g) gave (E)-1-(rel-(6R,7R)-7-methylspiro[4.5]decan-6-yl)but-2-en-1-one (1.6 g, 33%). Boiling point: 100° C. (0.07 mbar).

Odour description: Damascone-like (fruity, floral, agrestic), earthy, slightly spicy.

¹H-NMR (400 MHz, CDCl₃): δ6.74 (dq, J=6.9, 15.5, H—C(3)), 6.14 (dq, J=1.6, 15.5, H—C(2)), 2.76 (br. d, J=4.8, H—C(6')), 1.91 (dddd, J=0.7, 3.9, 13.2, 13.4, 1 H), 1.87 (dd, J=1.7, 6.8, MeC(3)), 1.85-1.75 (m, 1 H), 1.70-1.50 (m, 7 H), 1.44-1.15 (m, 6 H), 0.83 (d, J=7.1, MeC(7')).

¹³C-NMR (100 MHz, CDCl₃): δ204.34 (s, CO), 140.70 (d, C(3)), 135.99 (d, C(2)), 57.77 (d, C(6')), 45.81 (s, C(5')), 39.32 (t), 36.97 (t), 32.56 (d, C(7')), 31.82 (t), 29.05 (t), 24.14 (t), 23.94 (t), 22.73 (t), 20.44 (q), 18.08 (q).

MS (EI): 220 (12), 205 (14), 202 (3), 191 (5), 187 (4), 178 (3), 177 (4), 151 (91), 138 (31), 136 (16), 125 (13), 123 (19), 121 (13), 111 (37), 109 (32), 95 (66), 84 (5), 81 (30), 79 (22), 69 (100), 67 (34), 55 (38), 41 (60).

Example 10

(E)-1-(Spiro[4.5]dec-6-en-6-yl)but-2-en-1-one

At 5° C., a solution of lithium acetylide ethylene diamine complex (200 g, 2.17 mol) in THF (1 l) was treated dropwise with a solution of spiro[4.5]decan-6-one (196 g, 1.29 mol, prepared from cyclohexanone and 1,4-dibromobutane in the presence of potassium tert.-butylate in toluene) in THF (0.8 l). The resulting mixture was stirred for 3 h at 20° C., poured into a saturated aqueous solution of NH₄Cl, acidified with conc. HCl and extracted three time with MTBE (500 ml). The aqueous phase was extracted twice with MTBE (150 ml) and the combined organic phases were washed twice with water (500 ml), once with a saturated aqueous solution of NaCl, dried (MgSO₄), and concentrated. Short-path Vigreux-distillation (0.08 mbar, bath temperature: 140° C., head temp.: 100-105° C.) of the crude product (257 g) gave 6-ethynylspiro[4.5]decan-6-ol (180.8 g, 79%).

¹³C-NMR (100 MHz, CDCl₃): δ87.60 (s, CCH), 73.85 (s, C(6)), 72.38 (d, CCH), 50.23 (s, C(5)), 37.26 (t), 35.49 (br. t), 34.89 (br. t), 32.83 (br. t), 26.22 (t), 25.84 (t), 22.16 (br. t), 21.75 (t).

At 20-27° C., a solution of 6-ethynylspiro[4.5]decan-6-ol (180 g, 1 mol) in pyridine (1 l) was treated dropwise with POCl₃ (207 g, 2 mol). The resulting mixture was heated for 5.5 h heating at 85-90° C., poured into ice and extracted twice with pentane (800 and 300 ml). The combined organic phases were washed twice with water (500 ml), with a saturated aqueous solution of NaCl (300 ml), dried (MgSO₄), and concentrated. Short-path Vigreux-distillation (8 mbar, head temperature: 85° C.) of the crude product (146 g) gave 6-ethynylspiro[4.5]dec-6-ene (122.9 g, 76%).

¹³C-NMR (100 MHz, CDCl₃): δ136.43 (d, C(7)), 128.92 (s, C(6)), 84.16 (s, CCH), 75.39 (d, CCH), 44.69 (s, C(5)), 38.62 (t, 2C), 35.39 (t), 25.93 (t), 25.21 (t, 2C), 19.58 (t).

MS (EI): 160 (42), 145 (21), 132 (21), 131 (56), 118 (42), 117 (100), 115 (41), 104 (25), 103 (36), 91 (78), 78 (28), 77 (29), 67 (15), 65 (18), 63 (14), 51 (16), 41 (15), 39 (18).

A mixture of 6-ethynylspiro[4.5]dec-6-ene (120 g, 0.748 mol) and sulfuric acid (11.6 g) in acetic acid (500 ml) was heated for 2 h at 75° C., poured into ice, treated with 2N aqueous NaOH (10 ml) and extracted twice with MTBE (150 ml). The combined organic phases were treated with 2N aqueous NaOH (pH>7), washed with water (400 ml), with a saturated aqueous solution of NaCl (400 ml), dried (MgSO₄), and concentrated. Short-path Vigreux-distillation (0.08 mbar, head temperature: 85-90° C.) of the crude product (125 g) gave 1-(spiro[4.5]dec-6-en-6-yl)ethanone (62 g, 46%).

¹³C-NMR (100 MHz, CDCl₃): δ200.07 (s, CO), 146.84 (s, C(6)), 141.38 (d, C(7)), 43.86 (s, C(5)), 38.70 (t, 2C), 38.26 (t), 27.62 (q), 26.50 (t), 26.17 (t, 2C), 19.17 (t).

MS (EI): 178 (11), 163 (9), 150 (4), 149 (8), 136 (15), 135 (100), 121 (9), 107 (14), 93 (26), 91 (22), 79 (22), 77 (17), 67 (20), 43 (31), 39 (7).

At −70° C., a solution of diisopropylamine (40.9 g, 0.4 mol) in tetrahydrofuran (200 ml) was treated within 10 min. with n-butyl lithium (271 ml, 1.6M in hexane, 0.437 mol). The resulting solution was stirred at −40° C. for 20 min., cooled to −78° C., and treated within 20 min. with a solution of 1-(spiro[4.5]dec-6-en-6-yl)ethanone (62 g, 0.35 mol). The resulting solution was stirred 20 min. at −70° C. and treated with a solution of acetaldehyde (76.6 g, 1.75 mol) in tetrahydrofuran (100 ml). After 90 min. stirring, the reaction mixture was poured into a cold saturated aqueous solution of NH₄Cl (400 ml) and extracted twice with MTBE (400 and 200 ml). The combined organic phases were washed with a water (200 ml), and twice with a saturated solution of NaCl, dried (MgSO₄), and concentrated to give the desired intermediate 3-hydroxy-1-(spiro[4.5]dec-6-en-6-yl)butan-1-one (97.8 g) which was dissolved in acetic anhydride (70 ml, 0.73 mol). The resulting solution was treated with sodium acetate (31.4 g, 0.383 mol), heated at 80° C. for 8 h, treated with sodium acetate (10 g, 0.122 mol), heated at 80° C. for 15 h, treated with sodium acetate (10 g, 0.122 mol), heated at 80° C. for 2 h. The reaction mixture was cooled to 0° C., poured into ice/water and extracted three times with MTBE (200 ml). The combined organic phases were washed with 2N aqueous NaOH (300 ml), with a saturated aqueous NaCl solution (250 ml), dried (30 g MgSO₄) and concentrated. Short-path Vigreux distillation (0.08 mbar, bath temperature 140-180° C., head temperature: 80-146° C.) of the crude product (89.6 g) followed by distillation (0.08 mbar, bath temperature 150-180° C., head temperature: 98° C.) using a microdistillation column (20×1.5 cm, filled with 3×3 mm rolled wire netting) gave (E)-1-(spiro[4.5]dec-6-en-6-yl)but-2-en-1-one (55.6 g, 58%).

Odour description: fruity, Damascone-like, agrestic, tobacco.

$^1$H-NMR (400 MHz, CDCl$_3$): δ6.76 (dq, J=6.8, 15.3, H—C(3)), 6.52 (t, J=3.9, H—C(7')), 6.46 (dq, J=1.5, 15.3, H—C(2)), 2.19 (dt, J=4.0, 6.2, 2 H), 2.05-1.95 (m, 2 H), 1.88 (dd, J=1.7, 7.0, MeC(3)), 1.85-1.74 (m, 2 H), 1.67-1.57 (m, 4 H), 1.51-1.46 (m, 2 H), 1.41-1.33 (m, 2 H).

$^{13}$C-NMR (100 MHz, CDCl$_3$): δ194.65 (s, CO), 146.57 (s), 142.40 (d), 137.81 (d), 130.57 (d), 44.23 (s, C(5')), 38.53 (t, 2C), 37.47 (t), 25.89 (t), 25.83 (t, 2C), 19.16 (t), 18.21 (q).

MS (EI): 204 (17), 189 (100), 186 (7), 175 (32), 171 (9), 162 (15), 161 (38), 147 (43), 135 (30), 134 (17), 133 (29), 129 (10), 119 (17), 107 (20), 105 (28), 95 (21), 93 (31), 91 (61), 81 (16), 79 (37), 77 (36), 69 (57), 67 (35), 55 (22), 41 (71), 39 (32).

Example 11

(E)-1-(rel-4R,5R)-5-Methylspiro[2.5]oct-6-en-4-yl)but-2-en-1-one a) 1-Ethoxycyclopropanol/1-methoxycyclopropanol A solution of (1-ethoxycyclopropyl)oxy-trimethylsilane (25 ml, 124.9 mmol) in methanol (60 ml) was treated with conc. HCl (3 drops), stirred at 20° C. for 16 h, concentrated at 20° C., and the residue distilled (55° C., 19-20 mbar) to give 1-ethoxycyclopropanol/1-methoxycyclopropanol (92:8, 10.36 g, 82%).

$^1$H-NMR (400 MHz, CDCl$_3$): data of 1-Ethoxycyclopropanol: δ3.76 (q, 2H, J=8.0, OCH$_2$), 3.44 (s, OH), 1.21 (t, 3H, J=8.0, Me), 0.96-0.89 (m, 4 H).

b) 1-Cyclopropylidenepropan-2-one

Under N$_2$, a mixture of 1-ethoxycyclopropanol/1-methoxycyclopropanol (92:8, 10.36 g, 102.4 mmol), 1-triphenylphosphoranylidenepropan-2-one (38.84 g, 121.9 mmol) and benzoic acid (24 g, 10.2 mmol) in anhydrous benzene (500 ml) was refluxed for 20 h and then concentrated. The residue was filtered, and distilled (68° C., 40 mbar) giving 1-cyclopropylidenepropan-2-one (4.35 g, 45%).

$^1$H-NMR (400 MHz, CDCl$_3$): δ6.47-6.43 (m, H—C(1)), 2.34 (s, Me), 1.54-1.48 (m, 2 H), 1.40-1.32 (m, 2 H).

$^{13}$C-NMR (100 MHz, CDCl$_3$): δ198.8 (s, CO), 143.8 (s, C(1)=C), 121.6 (d, C(1)), 27.1 (q, Me), 5.1 (t), 2.6 (t).

c) rel-(4R,5R)-1-(5-Methylspiro[2.5]oct-6-en-4-yl)ethanone

At 20° C. under N$_2$, a suspension of anhydrous ZnCl$_2$ (0.31 g, 2.29 mmol) in Et$_2$O (1.5 ml) was treated with 1,3-pentadiene (65% pure, 3.34 ml, 22.9 mmol) then with a solution of 1-cyclopropylidenepropan-2-one (0.44 g, 4.58 mmol) in Et$_2$O (1,5 ml). After 24 h stirring, the resulting mixture treated with 6N aq. NaOH (3.1 ml) and the aqueous phase extracted three time with Et$_2$O. The combined organic phases were washed twice with a saturated aqueous solution of NH$_4$Cl, once with a saturated aqueous solution of NaCl, dried (MgSO$_4$), and concentrated. FC (100 g SiO$_2$, pentane/Et$_2$O 10:0.5) of the crude product (1.12 g) gave rel-(4R,5R)-1-(5-methylspiro[2.5]oct-6-en-4-yl)ethanone (279 mg, 36%).

$^1$H-NMR (400 MHz, CDCl$_3$): δ5.72-5.66 (m, 1 H), 5.62-5.57 (dm, 1 H), 2.68-2.58 (m, C(4)H), 2.48-2.39 (dm, 1 H), 2.16 (s, MeCO), 1.97 (d, J=5.6, C(5)H), 1.32-1.24 (dm, 1 H), 1.05 (d, J=7.6, C(5)Me), 0.67-0.64 (m, 1 H), 0.51-0.48 (m, 1 H), 0.40-0.32 (m, 2 H).

$^{13}$C-NMR (100 MHz, CDCl$_3$): δ209.3 (s, CO), 131.1 (d), 125.3 (d), 58.6 (d, C(4)), 32.8 (t, C(8)), 31.9 (q, OCMe), 31.7 (d, C(5)), 17.9 (s, C(3)), 17.5 (q, C(5)Me), 14.8 (t), 11.2 (t).

MS (EI): 164 (10), 149 (14), 144 (3), 135 (5), 131 (9), 121 (72), 106 (27), 105 (29), 93 (87), 91 (100), 79 (59), 77 (48), 65 (15), 43 (98), 39 (22).

d) rel-(4R,5R)-1-(5-Methylspiro[2.5]oct-6-en-4-yl)but-2-en-1-one

At −78° C. under N$_2$, a solution of diisopropylamine (2.57 ml, 18.2 mmol) in anhydrous THF (13.50 ml) was treated dropwise with a solution of 1.6M n-BuLi in hexane (11.40 ml, 18.2 mmol). The resulting solution was stirred 10 min. at 0° C., cooled to −78° C. and treated dropwise with rel-(4R,5R)-1-(5-methylspiro[2.5]oct-6-en-4-yl)ethanone (2.3 g, 14.0 mmol, rel-(4R,5R)-/rel-(4S,5R)-98:2) in anhydrous THF (2.2 ml). The resulting solution was stirred 1 h at −78° C., warmed to −20° C., cooled to −78° C. and treated with a solution of acetaldehyde (4.40 ml, 70.1 mmol) in anhydrous THF (13.5 ml). The resulting solution was stirred for 15 min. at −78° C., warmed to −30° C., cooled to −78° C., and treated slowly with a mixture of 2N HCl (11.62 ml) and of a saturated aqueous solution of NaCl (7 ml). The mixture was then warmed to 0° C., the aqueous phase extracted three times with Et$_2$O and the combined organic phases washed with a saturated aqueous solution of NaHCO$_3$, a saturated aqueous solution of NH$_4$Cl, a saturated aqueous solution of NaCl, dried (Na$_2$SO$_4$) and concentrated to give 4.06 g of crude product. A solution of the crude product (2.92 g, 14.0 mmol) in toluene (85 ml) was treated with para-toluene sulfonic acid monohydrate (133.5 mg, 0.702 mmol) stirred at 80° C. for 2 h, cooled, poured into a saturated aqueous solution of NaHCO$_3$. The aqueous phase was extracted three times with Et$_2$O and the combined organic phases washed with a saturated aqueous solution of NH$_4$Cl, a saturated aqueous solution of NaCl, and concentrated. FC (500 g SiO$_2$, hexane/Et$_2$O 10:0.5) of the crude product (3.4 g) gave two fractions of rel-(4R,5R)-1-(5-methylspiro[2.5]oct-6-en-4-yl)but-2-en-1-one (Fraction 1: 0.613 g, 23%, 2 steps, rel-(4R,5R)-/rel-(4S,5R)-93:7; Fraction 2: 1.36 g, 51%, 2 steps, rel-(4R,5R)-/rel-(4S,5R)-99.3:0.7).

Odour description: agrestic, fruity, floral.

$^1$H-NMR (400 MHz, CDCl$_3$): δ6.83-6.76 (dq, J=7, J=15.4, CH=CHMe), 6.24-6.18 (dq, J=1,6 Hz, J=15.2, CH=CHMe), 5.75-5.70 (m, 1H), 5.62-5.58 (d, J=8, 1 H), 2.70-2.60 (m, C(4)H), 2.52-2.42 (dm, J=18, 1 H), 2.14 (d, J=5.6, C(5)H), 1.90-1.83 (dm, J=5.2, CH=CHMe), 1.33-1.23 (dm, J=18, 1 H), 1.02 (d, J=7.6, C(5)Me), 0.65-0.58 (m, 1 H), 0.47-0.32 (m, 3 H).

$^{13}$C-NMR (100 MHz, CDCl$_3$): δ200.4 (s, CO), 141.5 (d), 132.6 (d), 131.2 (d), 125.7 (d), 55.6 (d, C(4)), 32.9 (t, C(8)), 32.0 (d, C(5)), 18.0 (q), 17.7 (s, C(3)), 17.6 (q), 14.4 (t), 10.8 (t).

Example 12

(E)-1-(rel-(4S,5R)-5-Methylspiro[2.5]oct-6-en-4-yl)but-2-en-1-one a) rel-(4S,5R)-1-(5-Methylspiro[2.5]oct-6-en-4-yl)ethanone Na (22.7 mg, 0.987 mmol) was added to MeOH (24 ml). The resulting solution was treated at 25° C. with rel-(4R,5R)-

1-(5-methylspiro[2.5]oct-6-en-4-yl)ethanone (1.62 g, 9.97 mmol, prepared in example 11), and heated at 80° C. for 64 h. The resulting solution was cooled, diluted pentane and poured into a saturated aqueous NH$_4$Cl solution. The aqueous phase was extracted twice with pentane and the combined organic phases were washed with a saturated aqueous NaCl solution, dried (Na$_2$SO$_4$) and concentrated. FC (250 g SiO$_2$, pentane/Et$_2$O 10:0.5) of the crude product (1.5 g) gave rel-(4S,5R)-1-(5-methylspiro[2.5]oct-6-en-4-yl)ethanone (930 mg, 57%) and a rel-(4R,5R)-1-(5-methylspiro[2.5]oct-6-en-4-yl)ethanone/rel-(4S,5R)-1-(5-methylspiro[2.5]oct-6-en-4-yl)ethanone (60:40, 408 mg, 25%).

$^1$H-NMR (400 MHz, CDCl$_3$): δ5.63 (d, J=1.2, 2 H), 2.70-2.62 (m, H—C(4')), 2.22 (d, J=5.6, 1 H), 2.18 (s, MeCO), 1.86 (m, 2 H), 1.04 (d, J=7.2, MeC(5)), 0.62-0.58 (m, 1 H), 0.48-0.41 (m, 2 H), 0.37-0.30 (m, 1 H).

$^{13}$C-NMR (100 MHz, CDCl$_3$): δ209.95 (s, CO), 132.04 (d), 124.70 (d), 58.52 (d, C(4)), 35.04 (t, C(8)), 32.15 (d, C(5)), 31.23 (q, MeCO), 20.37 (q, C(5)Me), 15.99 (s, C(3)), 12.28 (t), 8.97 (t).

b) rel-(4S,5R)-1-(5-Methylspiro[2.5]oct-6-en-4-yl) but-2-en-1-one

At −78° C. under N$_2$, a solution of diisopropylamine (1.04 ml, 7.37 mmol) in anhydrous THF (2.2 ml) was treated dropwise with a solution of 1.6M n-BuLi in hexane (4.6 ml, 7.37 mmol). The resulting solution was stirred 10 min. at 0° C., cooled to −78° C. and treated dropwise with a solution of rel-(4S,5R)-1-(5-methylspiro[2.5]oct-6-en-4-yl)ethanone (930 mg, 5.67 mmol) in anhydrous THF (2.2 ml). The resulting solution was stirred 10 min. at −78° C., warmed to −20° C., cooled to −78° C. and treated with a solution of acetaldehyde (1.6 ml, 28.35 mmol) in anhydrous THF (2.2 ml). The resulting solution was stirred for 1 h at −78° C., warmed to −40° C., cooled to −78° C., and treated slowly with a mixture of 2N HCl (11.62 ml) and of a saturated aqueous solution of NaCl (7 ml). The mixture was then warmed to 0° C., the aqueous phase extracted three times with Et$_2$O and the combined organic phases washed with a saturated aqueous solution of NaHCO$_3$, a saturated aqueous solution of NH$_4$Cl, a saturated aqueous solution of NaCl, dried (Na$_2$SO$_4$) and concentrated to give 1.44 g of crude product.

A solution of the crude product (1.41 g, 5.67 mmol) in toluene (28.4 ml) was treated with para-toluene sulfonic acid monohydrate (0.054 g, 0.284 mmol), stirred at 80° C. for 1 h, cooled, poured into a saturated aqueous solution of NaHCO$_3$. The aqueous phase was extracted three times with Et$_2$O and the combined organic phases washed with a saturated aqueous solution of NH$_4$Cl, a saturated aqueous solution of NaCl, and concentrated. FC (140 g SiO$_2$, hexane/Et$_2$O 10:0.5) of the crude product (1.19 g) gave rel-(4S,5R)-1-(5-methylspiro [2.5]oct-6-en-4-yl)but-2-en-1-one (0.69 g, 64%, 2 steps).

Boiling point: 55° C. (0.08 mbar).

Odour description: Damascone-like, fruity, floral, agrestic.

$^1$H-NMR (400 MHz, CDCl$_3$): δ6.84 (dq, J=6.8, 15.7, CH═CHMe), 6.19 (dq, J=1.7, 15.7, CH═CHMe), 5.65 (dddd, J=2.0, 2.8, 4.0, 10.0, 1 H), 5.59 (ddd, J=2.0, 4.0, 10.1, 1 H), 2.74-2.62 (m, H—C(4')), 2.63 (d, J=7.3, H—C(5')), 2.19 (dm, J=17.9, 1 H), 1.90 (dd, J=1.8, 6.8, CH═CHMe), 1.64 (dm, J=17.9, 1 H), 0.97 (d, J=6.8, C(5')Me), 0.54 (dddd, J=0.8, 4.3, 5.6, 10.1, 1 H), 0.41-0.30 (m, 2 H), 0.21 (br. ddd, 4.6, 5.6, 9.6, 1 H).

$^{13}$C-NMR (100 MHz, CDCl$_3$): δ200.78 (s, CO), 142.27 (d), 132.82 (d), 132.53 (d), 124.99 (d, C(4')), 54.86 (d, C(4')), 36.26 (t, C(8')), 32.58 (d, C(5')), 20.24 (q), 18.07 (q), 16.75 (s, C(3')), 10.80 (t), 8.51 (t).

MS (EI): 190 (1), 175 (6), 161 (5), 157(2), 147 (5), 121 (33), 106 (30), 105 (18), 93 (32), 91 (42), 79 (22), 77 (20), 69 (100), 41 (36), 39 (21).

IR: v$_{max}$ 2963, 2873, 1691, 1662, 1627, 1442, 1376, 1316, 1289, 1202, 1183, 1140, 1018, 1001, 970, 910, 875, 806, 695 cm$^{-1}$.

Example 13

(E)-1-(5-Methylspiro[2.5]oct-5-en-4-yl)but-2-en-1-one

At −78° C., a of solution of bis(cyclopentadienyl)zirconium dichloride (18.68 g, 63.9 mmol) in THF (200 ml) was treated dropwise with a solution of 3M ethylmagnesium bromide in Et$_2$O (42.5 ml). The resulting mixture was stirred for 1 h at −78° C., warmed to 0° C., stirred at 0° C. until the color of the solution turned red, and treated with a solution of 3-methylcyclohex-2-enone (7 g, 63.9 mmol) in THF (100 ml). After 3 h stirring at 20° C., the resulting mixture was concentrated. The residue was dissolved in dichloromethane (300 ml) and treated with TiCl$_4$ (7.0 ml, 63.9 mmol). The resulting mixture was stirred for 20 min. and treated with a saturated aqueous solution of NH$_4$Cl. The aqueous phase was extracted with dichloromethane. The combined organic phases were washed with a saturated aqueous solution of NaHCO$_3$, with a saturated aqueous solution of NaCl, and concentrated. FC (SiO$_2$, pentane) of the crude product (9.53 g) gave 5-methylspiro[2.5]oct-4-ene (3.42 g, 44%).

$^1$H-NMR (400 MHz, CDCl$_3$): δ4.74 (sext, J=1.5, H—C (4)), 1.96 (tm, J=6.3, 2 H), 1.77-1.70 (m, 2 H), 1.66 (dt, J=1.0, 1.3, Me), 1.45-1.40 (m, 2 H), 0.50-0.40 (m, 4 H).

$^{13}$C-NMR (100 MHz, CDCl$_3$): δ133.25 (s), 128.65 (d), 33.12 (t), 29.90 (t), 23.51 (q), 22.56 (t), 18.24 (s), 14.32 (t, 2C).

A mixture of 5-methylspiro[2.5]oct-4-ene (1.41 g, 11.5 mmol), acetic anhydride (2.83 ml, 29.9 mmol), and zinc chloride (203 mg, 1.5 mmol) was heated at 50° C. for 14.5 h, cooled to 20° C., poured into a mixture of a saturated aqueous solution of NaHCO$_3$ and ice, and extracted with pentane. The aqueous phase was extracted twice with pentane and the combined organic phases were washed with a saturated aqueous solution of NH$_4$Cl, with a saturated aqueous solution of NaCl, dried (Na$_2$SO$_4$), and concentrated. FC (300 g SiO$_2$, pentane/Et$_2$O10:0.5) of the crude product (1.91 g) gave unreacted 5-methylspiro[2.5]oct-4-ene (765 mg) and 1-(5-methylspiro[2.5]oct-5-en-4-yl)ethanone (479 mg, 25%).

$^1$H-NMR (400 MHz, CDCl$_3$): δ5.76-5.71 (m, H—C(6')), 2.20 (s, MeCO), 2.18-2.11 (m, 3 H), 2.10-1.99 (m, 1 H), 1.62 (dt, J=0.7, 1.5, MeC(5')), 0.73 (dm, J=13.0, 1 H), 0.61 (ddd, J=0.5, 4.8, 9.6, 1 H), 0.45 (ddd, J=4.7, 5.8, 8.9, 1 H), 0.36 (ddd, J=4.3, 5.8, 9.1, 1 H), 0.35-0.29 (m, 1 H), $^{13}$C-NMR (100 MHz, CDCl$_3$): δ210.07 (s, CO), 131.26 (s), 125.40 (d), 62.42 (d, C(4')), 29.46 (q), 28.00 (t), 24.38 (t), 22.95 (q), 18.07 (s, C(3')), 14.06 (t), 10.45 (t).

MS (EI): 164 (1), 149 (2), 135 (1), 121 (100), 106 (8), 105 (23), 93 (85), 91 (58), 79 (58), 77 (37), 65 (11), 55 (13), 51 (9), 43 (42), 41 (13), 39 (16).

At −78° C. under N$_2$, a solution of diisopropylamine (0.53 ml, 3.72 mmol) in anhydrous THF (2.75 ml) was treated dropwise with a solution of 1.6M n-BuLi in hexane (2.33 ml, 2.75 mmol). The resulting solution was warmed to −10° C., cooled to −78° C., and treated dropwise with a solution of 1-(5-methylspiro[2.5]oct-5-en-4-yl)ethanone (470 mg, 2.87 mmol) in anhydrous THF (2.75 ml). The resulting solution was warmed to −20° C., cooled to −78° C. and treated with a solution of acetaldehyde (0.81 ml, 14.3 mmol) in anhydrous THF (2.75 ml). The resulting solution was warmed to −10° C., cooled to −78° C., and treated slowly with a mixture of 2N HCl (6 ml) and of a saturated aqueous solution of NaCl (3.6 ml). The mixture was then warmed to 0° C., the aqueous phase extracted three times with $Et_2O$ and the combined organic phases washed with a saturated aqueous solution of $NaHCO_3$, a saturated aqueous solution of $NH_4Cl$, a saturated aqueous solution of NaCl, dried ($Na_2SO_4$), and concentrated. The residue (596 mg) was dissolved in toluene (20 ml) and treated with para-toluene sulfonic acid monohydrate (27 mg, 0.143 mmol). The resulting solution was stirred at 80° C. for 3 h, cooled, and poured into a saturated aqueous solution of $NaHCO_3$. The aqueous phase was extracted three times with $Et_2O$ and the combined organic phases washed with a saturated aqueous solution of $NH_4Cl$, a saturated aqueous solution of NaCl, and concentrated. FC (200 g $SiO_2$, hexane/$Et_2O$ 10:0.5) of the crude product (730 mg) gave (E)-1-(5-Methyl-spiro[2.5]oct-5-en-4-yl)but-2-en-1-one (0.354 g, 64%, 2 steps). Boiling point: 50° C. (0.07 mbar).

Odour description: Damascone-like, fruity, floral, agrestic.

$^1$H-NMR (400 MHz, $CDCl_3$): δ6.88 (dq, J=7.0, 15.4, CH=CHMe), 6.35 (dq, J=1.7, 15.4, CH=CHMe), 5.78-5.73 (m, H—C(6')), 2.35 (br. s, C(4')H), 2.19-2.11 (m, 2 H), 2.11-2.02 (m, 1 H), 1.91 (dd, J=1.6, 7.0 CH=CHMe), 1.61-1.59 (m, C(5')Me), 0.71 (br. dtd, J=0.8, 3.8, 12.9, 1 H), 0.60 (m, 1 H), 0.39-0.28 (m, 3 H).

$^{13}$C-NMR (100 MHz, $CDCl_3$): δ200.54 (s, CO), 142.80 (d), 131.48 (s), 130.76 (d), 125.58 (d), 59.14 (d, C(4')), 28.05 (t), 24.45 (t), 23.00 (q), 18.54 (s, C(3)), 18.25 (q), 13.68 (t), 10.15 (t).

Example 14

Ethyl 7-methylspiro[4.5]dec-7-ene-6-carboxylate a) At 35° C., a solution of vinylmagnesium bromide (0.8 mol, prepared from Mg and vinylbromide) in THF (268 ml) was treated within 1.5 h with a solution of cyclopentanone (47.5 ml, 0.534 mol) in THF (80 ml). The resulting mixture was refluxed for 30 min., cooled to 35° C., treated with a saturated aqueous solution of $NH_4Cl$, and extracted with MTBE (300 ml). The organic phase was washed with a saturated aqueous solution of $NaHCO_3$ (200 ml), with a saturated aqueous solution of NaCl (250 ml), dried ($MgSO_4$) and concentrated. Vigreux-Distillation (0.1 mbar, bath temperature 60° C., head temp. 27° C.) of the crude product (46.1 g) gave 1-vinylcy-clopentanol (28.78 g, 48%).

In an autoclave under $N_2$, a mixture of 1-vinylcyclopen-tanol (65 g, 0.58 mol), 2-methoxypropene (108 ml, 1.15 mol), 85% phosphoric acid (0.29 ml), triethylamine (0.63 ml) was heated at 130° C. for 15 h. The reaction mixture was cooled to 20° C., diluted with MTBE (500 ml), washed three times with water (25 ml), once with a saturated aqueous solution of NaCl (25 ml), dried ($MgSO_4$) and concentrated. Widmer-Distilla-tion (0.13 mbar, head temp. 58° C.) of the crude product gave 5-cyclopentylidenepentan-2-one (63.67 g, 72%).

A suspension of NaH (8.2 g, 55% in oil, 184 mmol, washed with hexane) in THF (300 ml) was treated dropwise within 1.5 h with a solution of triethylphosphonoacetate (35 ml, 176 mmol) in THF (40 ml). The resulting mixture was stirred for 1 h, treated dropwise with a solution of 5-cyclopentylidene-pentan-2-one (25.48 g, 167 mmol) in THF (80 ml), heated at reflux for 20 h, cooled to 15° C., and treated with a saturated aqueous solution of $NH_4Cl$ (150 ml). The aqueous phase was extracted with MTBE (80 ml) and the combined organic phases were washed twice with a saturated aqueous solution of NaCl (50 ml), dried ($MgSO_4$) and concentrated. Widmer-Distillation (0.08 mbar, head temp. 80-90° C.) of the crude product (35.65 g, 67:24 E/Z) gave 84:16 (E/Z)-ethyl 6-cyclo-pentylidene-3-methylhex-2-enoate (24.7 g, 69%). Boiling point: 92° C. (0.08 mbar).

IR: $v_{max}$ 2953, 2868, 1717, 1649, 1449, 1368, 1273, 1222, 1148, 1050, 862 $cm^{-1}$.

(E)-ethyl 6-cyclopentylidene-3-methylhex-2-enoate $^{13}$C-NMR (100 MHz, $CDCl_3$): δ166.79 (s, CO), 159.77 (s), 144.15 (s), 118.38 (d), 115.49 (d), 59.34 (t, $CH_2O$), 40.72 (t), 33.48 (t), 28.54 (t), 27.51 (t), 26.32 (t), 26.24 (t), 18.69 (q), 14.25 (q).

(Z)-ethyl 6-cyclopentylidene-3-methylhex-2-enoate $^{13}$C-NMR (100 MHz, $CDCl_3$): δ166.22 (s, CO), 160.08 (s), 143.74 (s), 119.06 (d), 116.11 (d), 59.29 (t, $CH_2O$), 40.72 (t), 33.20 (t), 28.42 (t), 28.26 (t), 26.34 (t), 26.28 (t), 25.23 (q), 14.25 (q).

b) At −20° C., conc. sulphuric acid (83 ml) was treated drop-wise within 1 h with a solution of 84:16 (E/Z)-ethyl 6-cyclo-pentylidene-3-methylhex-2-enoate (20 g, 90 mmol) in diiso-propyl ether (28 ml). The resulting mixture was poured into ice (140 g)/water (100 ml), diluted with MTBE (140 ml), washed three times with a saturated aqueous solution of $NaHCO_3$ (70 ml), three times with a saturated aqueous solution of NaCl (70 ml), dried ($MgSO_4$) and concentrated. Vigreux-Distillation (0.1 mbar, head temp. 80° C.) of the crude product (18.3 g) gave ethyl 7-methylspiro[4.5]dec-7-ene-6-carboxylate (4.76 g, 24%). Boiling point: 90° C. (0.1 mbar).

Odour description: fruity, floral, agrestic.

$^1$H-NMR (400 MHz, $CDCl_3$): δ5.60-5.56 (m, H—C(8')), 4.18 (dq, J=7.2, 10.9, CHO), 4.13 (dq, J=7.1, 10.9, CHO), 2.62 (br. s, H—C(6')), 2.15-2.03 (m, 2 H), 2.03-1.95 (m, 1 H), 1.65 (dt, J=1.7, MeC(7')), 1.73-1.58 (m, 4 H), 1.58-1.41 (m, 2 H), 1.35-1.29 (m, 1 H), 1.27 (t, J=7.1, $MeCH_2O$), 1.30-1.21 (m, 2 H).

$^{13}$C-NMR (100 MHz, $CDCl_3$): δ173.96 (s, CO), 130.11 (s, C(7')), 124.47 (d, C(8')), 60.13 (t, $CH_2O$), 55.81 (d, C(6')), 43.78 (s, C(5')), 37.69 (t), 36.63 (t), 28.23 (t), 24.00 (t), 23.90 (t), 23.12 (t), 23.03 (q), 14.34 (q).

MS (EI): 222 (31), 207 (2), 193 (1), 179 (3), 177 (2), 176 (9), 149 (98), 148 (100), 141 (18), 134 (12), 133 (11), 128 (14), 119 (9), 113 (13), 107 (21), 106 (30), 105 (28), 93 (23), 91 (29), 81 (31), 79 (20), 77 (13), 67 (15), 55 (6), 41 (9).

Example 15

(E)-1-(7-Methylspiro[4.5]dec-7-en-6-yl)but-2-en-1-one and (E)-1-(7-methylspiro[4.5]dec-6-en-6-yl)but-2-en-1-one Method 1.

At 20° C., a solution of lithium diisopropylamine (9.3 ml, 2M in THF/heptane) was treated dropwise within 10 min. with a solution of allylmagnesium chloride (15 ml, 2 M in THF). The resulting mixture was heated at 33° C., treated dropwise with a solution of ethyl 7-methylspiro[4.5]dec-7-ene-6-carboxylate (6 g, 27 mmol) in THF (7 ml), stirred at 20° C. for 1 h and at 40° C. for 24 h, treated with a mixture of allylmagnesium chloride (15 ml, 2 M in THF) and lithium diisopropylamine (9.3 ml, 2M in THF/heptane), stirred at 30° C. for 2 h, poured into a mixture of a saturated aqueous solution of $NH_4Cl$ (100 ml) and ice (115 g), and diluted with MTBE (200 ml). The organic phase was washed with 10% aqueous HCl (80 ml), with a saturated aqueous solution of NaHCO₃ (80 ml), with a saturated aqueous solution of NaCl (50 ml), dried (MgSO₄) and concentrated. FC (SiO₂, hexane/MTBE 100:1 to 90:10) of the crude product (8.3 g) gave (E)-1-(7-methylspiro[4.5]dec-7-en-6-yl)but-2-en-1-one and (E)-1-(7-methylspiro[4.5]dec-6-en-6-yl)but-2-en-1-one (1 g, 17%).

(E)-1-(7-Methylspiro[4.5]dec-7-en-6-yl)but-2-en-1-one

Boiling point: 115° C. (0.09 mbar)
$^1$H-NMR (400 MHz, CDCl₃): δ6.87 (dq, J=6.9, 15.4, H—C(3)), 6.33 (dq, J=1.7, 15.4, H—C(2)), 5.63-5.59 (br. s, H—C(8')), 2.91 (br. s, H—C(6')), 2.19-2.01 (m, 2 H), 1.88 (dd, J=1.7, 6.9, MeC(3)), 1.83 (ddd, J=7.1, 10.5, 13.2, 1 H), 1.68-1.56 (m, 4 H), 1.58-1.55 (br. m, MeC(7')), 1.52-1.41 (m, 2 H), 1.35-1.29 (m, 1 H), 1.28-1.21 (br. dd, J=6.0, 14.0, 1 H), 1.20-1.11 (m, 1 H).
$^{13}$C-NMR (100 MHz, CDCl₃): δ202.17 (s, CO), 142.39 (d), 131.95 (d), 131.12 (s), 124.28 (d), 60.45 (d), 44.41 (s), 37.45 (t), 37.25 (t), 28.29 (t), 23.90 (t), 23.61 (q), 23.57 (t), 23.13 (t), 18.32 (q).
MS (EI): 218 (14), 203 (4), 189 (2), 175 (2), 161 (2), 149 (56), 135 (5), 121 (6), 119 (3), 107 (19), 106 (6), 105 (13), 93 (21), 91 (24), 81 (43), 79 (20), 77 (14), 69 (100), 55 (10), 41 (34), 39 (15).
Odour description: green, floral, rosy.

(E)-1-(7-Methylspiro[4.5]dec-6-en-6-yl)but-2-en-1-one

Boiling point: 117° C. (0.1 mbar)
$^1$H-NMR (400 MHz, CDCl₃): δ6.73 (dq, J=6.9, 15.7, H—C(3)), 6.13 (dq, J=1.6, 15.7, H—C(2)), 1.97 (br. t, J=6.3, 2 H), 1.91 (dd, J=1.6, 7.0, MeC(3)), 1.77-1.35 (m, 12 H), 1.51 (s, MeC(7)).
$^{13}$C-NMR (100 MHz, CDCl₃): δ202.8 (s, CO), 145.7 (d, C(3)), 139.0 (s, C(7')), 134.9 (d, C(2)), 131.1 (s, C(6')), 45.1 (s, C(5')), 37.6 (t, C(1'), C(4')), 34.7 (t, C(10')), 31.0 (t, C(8')), 23.9 (t, C(2'), C(3')), 21.5 (q, C(4)), 19.5 (t, C(9')), 18.4 (q, MeC(7')).
MS (EI): 218 (46), 203 (74), 189 (37), 175 (46), 161 (51), 149 (100), 133 (29), 121 (18), 119 (22), 109 (25), 107 (40), 106 (8), 105 (45), 93 (39), 91 (68), 81 (32), 79 (43), 77 (41), 69 (65), 55 (31), 41 (83), 39 (35).
Odour description: green, floral, rosy, woody.
Method 2.
(E)-1-(7-methylspiro[4.5]dec-7-en-6-yl)but-2-en-1-one was prepared as described in the synthesis of (E)-1-(rel-(6S, 7S)-7-methylspiro[4.5]dec-9-en-6-yl)but-2-en-1-one (Example 21) from ethyl 7-methylspiro[4.5]dec-7-ene-6-carboxylate (2.5 g, 11 mmol) by allylmagnesium chloride addition followed by treatment of the crude product with KOt-Bu in DMF leading to a mixture of (E)-1-(7-methylspiro[4.5]dec-7-en-6-yl)but-3-en-1-one and (E)-1-(7-methylspiro[4.5]dec-7-en-6-yl)but-2-en-1-one that was treated with PTSA.H₂O in toluene (2.5 h, 60° C.) to give (E)-1-(7-methylspiro[4.5]dec-7-en-6-yl)but-2-en-1-one (0.6 g, 24% overall yield) after FC.
Method 3.
(E)-1-(7-methylspiro[4.5]dec-6-en-6-yl)but-2-en-1-one. Spiro[4.5]decan-6-one was transformed in three steps into 7-methylspiro[4.5]decan-6-one by methoxycarbonylation (MeOCO₂Me, NaH, THF, reflux, 93%) followed by methylation of the resulting ketoester (MeI, K₂CO₃, acetone, reflux, 2.5 d) and subsequent demethoxycarbonylation of the crude product (AcOH/H₂O/H₂SO₄ 10:4:3, reflux, 2 h, 79%). The required intermediate 1-(7-methylspiro[4.5]dec-6-en-6-yl)ethanone was then prepared from 7-methylspiro[4.5]decan-6-one according to the Example 10 via 6-ethynyl-7-methylspiro[4.5]decan-6-ol (lithium acetylide ethylenediamine complex, THF, 2 h, 0-20° C., 75%, 78:22 diastereomeric mixture) and 6-ethynyl-7-methylspiro[4.5]dec-6-ene (POCl₃, pyridine, 100° C., 19 h, 45%) that was treated with AcOH/H₂SO₄ (20° C., 50 min., 34%) to give 1-(7-methylspiro[4.5]dec-6-en-6-yl)ethanone. Subsequent aldol condensation with acetaldehyde (LDA, THF; according to the Example 10) followed by treatment of the crude with acetic anhydride/sodium acetate (80° C., 5 h, 59%; according to the Example 10) gave (E)-1-(7-methylspiro[4.5]dec-6-en-6-yl)but-2-en-1-one.

7-methylspiro[4.5]decan-6-one

Boiling point: 57° C. (0.09 mbar)
$^{13}$C-NMR (100 MHz, CDCl₃): δ215.63 (s), 56.79 (s, C(5)), 41.98 (d), 40.48 (t), 36.50 (t), 36.39 (t), 34.16 (t), 25.37 (t), 24.81 (t), 22.78 (t), 15.01 (q).

6-ethynyl-7-methylspiro[4.5]decan-6-ol

MS (EI): 192 (1), 191 (1), 177 (9), 166 (5), 164 (5), 163 (10), 159 (22), 151 (40), 149 (23), 145 (15), 135 (77), 131 (21), 125 (12), 121 (26), 117 (21), 110 (73), 108 (63), 97 (50), 95 (100), 93 (66), 91 (49), 82 (86), 81 (72), 79 (61), 77 (41), 67 (98), 55 (71), 53 (74), 41 (75), 39 (43).

6-ethynyl-7-methylspiro[4.5]dec-6-ene $^1$H-NMR (400 MHz, CDCl₃): δ3.03-3.02 (br. m, H—CC (6)), 2.01 (tm, J=6.2, 0.9, 2 H), 1.97-1.86 (m, 1 H), 1.90 (m, Me), 1.76-1.53 (m, 7 H), 1.47-1.36 (m, 4 H).
$^{13}$C-NMR (100 MHz, CDCl₃): δ143.25 (s, C(7)), 122.62 (s, C(6)), 82.87 (s, CCH), 80.16 (d, CCH), 45.02 (s, C(5)), 38.70 (t, 2C), 35.41 (t), 31.72 (t), 25.17 (t, 2C), 22.72 (q), 19.75 (t).
MS (EI): 174 (44), 159 (22), 146 (12), 145 (36), 132 (100), 131 (42), 117 (81), 115 (42), 105 (20), 103 (23), 91 (67), 79 (13), 77 (24), 67 (9), 65 (13), 53 (11), 51 (12), 41 (16), 39 (16).

1-(7-Methylspiro[4.5]dec-6-en-6-yl)ethanone $^1$H-NMR (400 MHz, CDCl₃): δ2.29 (s, MeCO), 1.95 (br. t, J=0.6, 6.4, C(8)H₂), 1.77-1.56 (m, 8 H), 1.60 (t, J=0.9, MeC (7)), 1.52-1.40 (m, 4 H).
$^{13}$C-NMR (100 MHz, CDCl₃): δ210.41 (s, CO), 142.38 (s), 129.15 (s), 44.62 (s, C(5)), 37.52 (t, 2C), 34.87 (t), 33.61 (q), 30.89 (t), 24.10 (t, 2C), 20.95 (q), 19.37 (t).
MS (EI): 192 (3), 177 (9), 163 (7), 159 (2), 150 (18), 149 (100), 135 (16), 121 (7), 107 (17), 93 (18), 91 (18), 81 (13), 79 (15), 77 (12), 67 (9), 55 (8), 43 (32).

Example 16

Ethyl 7-methylenespiro[4.5]dec-8-ene-6-carboxylate, ethyl 7-methylspiro[4.5]deca-6,8-diene-6-carboxylate, and ethyl 7-methylspiro[4.5]deca-7,9-diene-6-carboxylate a) Ethyl 7-methyl-9-oxospiro[4.5]dec-7-ene-6-carboxylate A mixture of 1-cyclopentylidenepropan-2-one/1-cyclopentenylpropan-2-one (25:75, 100 g, 0.805 mol), ethyl acetoacetate (105 g, 0.805 mol), and zinc chloride (16.5 g, 0.12 mol) in heptane (100 ml) and benzene (100 ml) was refluxed for 6 days using a Dean-Stark apparatus. The resulting mixture was cooled, washed with water (250 ml), with a 5% aqueous solution of $NaHCO_3$ (250 ml), with water, dried ($MgSO_4$) and concentrated. Vigreux-Distillation (0.1 mbar, bath temperature 150° C., head temp. 106-130° C.) of the crude product (174 g) followed by FC ($SiO_2$, hexane/MTBE 10:1 to 5:1) gave ethyl 7-methyl-9-oxospiro[4.5]dec-7-ene-6-carboxylate (23 g, 12%).

$^1$H-NMR (400 MHz, $CDCl_3$): δ5.95 (s, H—C(8')), 4.21 (q, J=7.2, CHO), 4.20 (q, J=7.2, CHO), 3.02 (s, H—C(6')), 2.90 (dd, J=0.5, 16.5, H—C(10')), 2.18 (br. d, J=16.4, H—C(10')), 1.96 (dd, J=0.4, 1.4, MeC(7')), 1.77-1.61 (m, 5 H), 1.58-1.39 (m, 3 H), 1.29 (t, J=7.1, $MeCH_2O$).

$^{13}$C-NMR (100 MHz, $CDCl_3$): δ199.14 (s, C(910), 170.60 (s, $CO_2$), 155.65 (s, C(7')), 127.97 (d, C(8')), 61.11 (t, $OCH_2$), 57.38 (d, C(6')), 46.64 (s, C(5')), 44.74 (t), 38.51 (t), 37.25 (t), 23.77 (t), 23.66 (t), 23.57 (q), 14.20 (q).

MS (EI): 236 (19), 207 (1), 194 (18), 191 (21), 163 (33), 154 (88), 135 (18), 126 (83), 122 (29), 121 (37), 109 (22), 98 (100), 93 (26), 91 (43), 82 (7), 79 (26), 77 (32), 67 (21), 53 (23), 41 (21), 29 (31).

b) cis- and trans-Ethyl 9-hydroxy-7-methylspiro[4.5]dec-7-ene-6-carboxylate

A solution of ethyl 7-methyl-9-oxospiro[4.5]dec-7-ene-6-carboxylate (6.4 g, 27.3 mmol) in methanol (120 ml) was treated with anhydrous cerium trichloride (6.72 g, 27.3 mmol). The resulting mixture was stirred for 45 min., cooled to 0° C., and added within 40 min. to a mixture of sodium borohydride (0.75 g, 96%, 19.1 mmol) in methanol (60 ml) at 0° C. The resulting mixture was stirred for 2 h at 20° C., cooled to 0° C., treated with sodium borohydride (0.75 g, 96%, 19.1 mmol), stirred for 3 h at 20° C., cooled to 0° C., poured into 2N aqueous HCl and ice, and extracted three times with MTBE (200 ml). The combined organic phases were washed three times with a saturated aqueous solution of NaCl, dried ($MgSO_4$) and concentrated. FC ($SiO_2$, hexane/MTBE 3:1) of the crude product (7.6 g, cis/trans 19:81) gave cis-ethyl 9-hydroxy-7-methylspiro[4.5]dec-7-ene-6-carboxylate (0.82 g 13%), 29:71 cis-/trans-ethyl 9-hydroxy-7-methylspiro[4.5]dec-7-ene-6-carboxylate (0.71 g, 11%), and trans-ethyl 9-hydroxy-7-methylspiro[4.5]dec-7-ene-6-carboxylate (3.52 g, 54%).

cis-Ethyl 9-hydroxy-7-methylspiro[4.5]dec-7-ene-6-carboxylate $^1$H-NMR (400 MHz, $CDCl_3$): δ5.72-5.70 (m, H—C(8')), 4.34-4.29 (m, H—C(9')), 4.20-4.08 (m, $CH_2O$), 2.78 (br. s, H—C(6')), 2.29 (dd, J=5.8, 14.3, H—C(10')), 1.72 (td, J=0.5, 1.5, MeC(7')), 1.77-1.50 (m, 8 H), 1.52 (dm, J=14.5, H—C(10')), 1.36-1.28 (m, 1 H), 1.26 (t, J=7.1, $MeCH_2O$).

$^{13}$C-NMR (100 MHz, $CDCl_3$): δ172.65 (s, $CO_2$), 134.01 (s, C(7')), 126.41 (d, C(8')), 65.34 (d, C(9')), 60.40 (t, $OCH_2$), 55.15 (d, C(6')), 43.25 (s, C(5')), 38.97 (t), 38.41 (t), 37.14 (t), 24.07 (t), 23.55 (t), 22.95 (q), 14.28 (q).

MS (EI): 238 (6), 220 (5), 209 (28), 196 (5), 192 (8), 181 (10), 165 (55), 164 (64), 155 (15), 147 (86), 135 (32), 122 (93), 105 (100), 91 (50), 82 (22), 81 (30), 79 (39), 77 (34), 69 (23), 67 (31), 55 (32), 41 (33), 29 (35).

trans-Ethyl 9-hydroxy-7-methylspiro[4.5]dec-7-ene-6-carboxylate $^1$H-NMR (400 MHz, $CDCl_3$): δ5.66-5.63 (m, H—C(8')), 4.23-4.10 (m, H—C(9'), $CH_2O$), 2.63 (br. s, H—C(6')), 2.24 (br. s, OH), 1.93 (dd, J=9.9, 12.5, H—C(10')), 1.75 (ddt, J=1.0, 6.5, 12.5, H—C(10')), 1.74-1.58 (m, 4 H), 1.68 (tm, J=0.5, 1.5, MeC(7')), 1.56-1.40 (m, 2 H), 1.40-1.30 (m, 2 H), 1.28 (t, J=7.1, $MeCH_2O$).

$^{13}$C-NMR (100 MHz, $CDCl_3$): δ173.33 (s, $CO_2$), 135.51 (s, C(7')), 128.82 (d, C(8')), 61.31 (d, C(9')), 60.48 (t, $OCH_2$), 55.39 (d, C(6')), 45.66 (s, C(5')), 38.59 (t), 37.93 (t), 37.12 (t), 23.61 (t), 23.31 (t), 22.59 (q), 14.28 (q).

MS (EI): 238 (5), 220 (3), 209 (22), 196 (4), 192 (6), 181 (8), 165 (40), 164 (49), 155 (13), 147 (58), 135 (27), 122 (65), 105 (100), 91 (56), 82 (21), 81 (25), 79 (35), 77 (32), 69 (20), 67 (26), 55 (26), 41 (28), 29 (28).

c) Ethyl 7-methylenespiro[4.5]dec-8-ene-6-carboxylate, ethyl 7-methylspiro[4.5]deca-6,8-diene-6-carboxylate, and ethyl 7-methylspiro[4.5]deca-7,9-diene-6-carboxylate A solution of 35:65 cis-/trans-ethyl 9-hydroxy-7-methylspiro[4.5]dec-7-ene-6-carboxylate (0.1 g, 0.42 mmol) in THF (1 ml) was treated with five drops of water and five drops of 20% sulphuric acid, heated at 100° C. for 2 h, cooled to 20° C., poured into ice, and extracted with MTBE (20 ml). The organic phase was washed with a saturated aqueous solution of NaCl, dried ($MgSO_4$) and concentrated. FC ($SiO_2$, hexane/MTBE 10:1) of the crude product (70 mg) gave a 77:11:11 mixture of ethyl 7-methylenespiro[4.5]dec-8-ene-6-carboxylate, ethyl 7-methylspiro[4.5]deca-6,8-diene-6-carboxylate, and ethyl 7-methylspiro[4.5]deca-7,9-diene-6-carboxylate (40 mg, 43%). Boiling point: 100° C. (0.09 mbar).

Odour description: fruity, floral.

Ethyl 7-methylenespiro[4.5]dec-8-ene-6-carboxylate $^1$H-NMR (400 MHz, $CDCl_3$): δ6.17 (ddquint, J=0.6, 2.2, 10.0, 1 H), 5.86-5.79 (m, 1 H), 5.00 (br. s, 1 H), 4.95 (br. s, 1 H), 4.11 (qd, 0.6, 7.2, $CH_2O$), 3.04 (br. s, H—C(6')), 2.51 (dm, J=18.1, 1 H), 1.92 (br. dd, J=5.7, 18.1, 1 H), 1.75-1.54 (m, 5 H), 1.48-1.29 (m, 3 H), 1.24 (t, J=7.1, $MeCH_2O$).

$^{13}$C-NMR (100 MHz, $CDCl_3$): δ172.69 (s, CO), 140.45 (s), 129.80 (d), 127.41 (d), 114.77 (t), 60.12 (t, $OCH_2$), 55.73 (d, C(6')), 43.66 (s, C(5')), 38.41 (t), 37.53 (t), 35.15 (t), 24.44 (t), 24.13 (t), 14.19 (q).

MS (EI): 220 (5), 205 (1), 191 (1), 175 (2), 149 (3), 148 (10), 147 (81), 146 (20), 132 (3), 131 (15), 119 (9), 105 (100), 91 (24), 77 (15), 65 (7), 55 (5), 41 (9), 29 (11).

Ethyl 7-methylspiro[4.5]deca-6,8-diene-6-carboxylate, $^1$H-NMR (400 MHz, $CDCl_3$): δ5.86-5.80 (m, 2 H), 4.24 (q, 7.2, $CH_2O$), 2.16-2.13 (m, 2 H), 1.82 (s, MeC(7')), 1.73-1.55 (m, 8H), 1.32 (t, J=7.1, $MeCH_2O$).

$^{13}$C-NMR (100 MHz, $CDCl_3$): δ170.06 (s, CO), 133.08 (s), 132.10 (s), 128.74 (d), 128.33 (d), 59.99 (t, $OCH_2$), 44.44 (s, C(5')), 36.64 (t), 35.77 (t, 2C), 24.21 (t, 2C), 19.60 (q), 14.32 (q).

MS (EI): 220 (14), 205 (1), 191 (3), 175 (48), 149 (42), 148 (7), 147 (51), 145 (83), 132 (16), 131 (14), 119 (16), 105 (100), 91 (38), 77 (23), 65 (10), 55 (9), 41 (10), 29 (16).

Ethyl 7-methylspiro[4.5]deca-7,9-diene-6-carboxylate $^1$H-NMR (400 MHz, $CDCl_3$): δ5.80-5.74 (m, 2 H), 5.55 (br. d, J=8.5, 1 H), 4.13 (dq, J=7.1, 10.8, CHO), 4.10 (dq, J=7.1, 10.8, CHO), 2.73 (s, H—C(6')), 1.80 (br. s, MeC(7')), 1.75-1.56 (m, 8 H), 1.24 (t, J=7.1, MeCH$_2$O).

$^1$H-NMR (400 MHz, C$_6$D$_6$): δ5.78 (dd, J=5.3, 9.5, 1 H), 5.71-5.67 (m, 1 H), 5.56 (dm, J=0.8, 9.5, 1 H), 3.97 (dq, J=7.1, 10.8, CHO), 3.92 (dq, J=7.1, 10.8, CHO), 2.80 (s, H—C(6')), 1.80-1.77 (m, MeC(7')), 1.77-1.47 (m, 8 H), 0.95 (t, J=7.1, MeCH$_2$O).

$^{13}$C-NMR (100 MHz, CDCl$_3$): δ171.87 (s, CO), 134.09 (d), 131.43 (s), 121.40 (d), 121.16 (d), 60.10 (t, OCH$_2$), 55.16 (d, C(6')), 45.94 (s, C(5')), 39.93 (t), 35.87 (t), 23.92 (t), 23.06 (t), 22.79 (q), 14.23 (q).

$^{13}$C-NMR (100 MHz, C$_6$D$_6$): δ170.75 (s, CO), 134.40 (d), 131.48 (s), 121.58 (d), 121.35 (d), 59.67 (t, OCH$_2$), 55.54 (d, C(6')), 45.98 (s, C(5')), 39.95 (t), 35.94 (t), 24.08 (t), 23.18 (t), 22.66 (q), 14.03 (q).

MS (EI): 220 (9), 205 (1), 191 (1), 175 (1), 149 (3), 148 (6), 147 (52), 145 (6), 132 (2), 131 (6), 119 (6), 105 (100), 91 (13), 77 (9), 65 (4), 55 (3), 41 (3), 29 (10).

d) Ethyl 7-methylenespiro[4.5]dec-8-ene-6-carboxylate, ethyl 7-methylspiro[4.5]deca-6,8-diene-6-carboxylate, and ethyl 7-methylspiro[4.5]deca-7,9-diene-6-carboxylate A solution of 35:65 cis-/trans-ethyl 9-hydroxy-7-methylspiro[4.5]dec-7-ene-6-carboxylate (0.1 g, 0.42 mmol) in toluene (1 ml) was treated with para-toluenesulfonic acid monohydrate (27.5 mg, 0.345 mmol) and molecular sieves, heated at reflux for 2 h, cooled to 0° C., poured into ice, and extracted with MTBE (20 ml). The organic phase was washed with a saturated aqueous solution of NaCl, dried (MgSO$_4$) and concentrated. FC (SiO$_2$, hexane/MTBE 10:1) of the crude product (75 mg) gave a 1:1:1 mixture of ethyl 7-methylenespiro[4.5]dec-8-ene-6-carboxylate, ethyl 7-methylspiro[4.5]deca-6,8-diene-6-carboxylate, and ethyl 7-methylspiro[4.5]deca-7,9-diene-6-carboxylate (40 mg, 43%).

Example 17

(2-methylcyclopropyl)(rel-(6S,7R)-7-methylspiro[4.5]dec-8-en-6-yl)methanone A solution of trimethylsulfoxonium iodide (3.1 g, 13.7 mmol) in DMSO (30 ml) was added dropwise to a mixture of sodium hydride (0.6 g, 13.7 mmol) in DMSO (10 ml). The resulting mixture was stirred for 45 min., treated with a solution of (E)-1-Vet-(6S,7R)-7-Methylspiro[4.5]dec-8-en-6-yl)but-2-en-1-one (2.5 g, 11.5 mmol) in DMSO (10 ml). After stirring for 2.5 h, the reaction mixture was poured into a cold saturated aqueous solution of NH$_4$Cl (100 ml) and extracted twice with hexane (80 ml). The combined organic phases were washed with water (80 ml), dried (MgSO$_4$) and concentrated. FC (180 g SiO$_2$, hexane/MTBE 30:1) of the crude product (2.26 g) gave (2-methylcyclopropyl)(rel-(6S,7R)-7-methylspiro[4.5]dec-8-en-6-yl)methanone (1.04 g, 60:40 diastereomeric mixture, 39%). Boiling point: 105° C. (0.08 mbar).

Odour description: woody, Damascone-like.

Data of the main diastereomer:

$^1$H-NMR (400 MHz, CDCl$_3$): selected signals: δ5.58-5.48 (m, H—C(8'), H—C(9')), 2.655 (d, J=10.2, H—C(6')), 2.61-2.49 (m, H—C(7')), 1.12 (d, J=5.9, MeC(3)), 0.89 (d, J=6.8, MeC(7)).

$^{13}$C-NMR (100 MHz, CDCl$_3$): δ214.28 (s, CO), 132.93 (d, C(8')), 124.37 (d, C(9')), 62.59 (d, C(6')), 44.94 (s, C(5')), 39.69 (t), 38.11 (t), 33.38 (d, C(7')), 32.27 (d), 30.28 (t), 24.54 (t), 23.84 (t), 20.53 (t), 20.46 (d), 20.02 (q), 18.11 (q).

MS (EI): 232 (4), 217 (1), 203 (1), 175 (1), 149 (13), 134 (18), 119 (9), 107 (6), 106 (5), 105 (8), 93 (6), 91 (11), 83 (100), 79 (9), 77 (6), 67 (6), 55 (23), 41 (8), 29 (4).

Data of the minor diastereomer:

$^1$H-NMR (400 MHz, CDCl$_3$): selected signals: δ5.58-5.48 (m, H—C(8'), H—C(9')), 2.660 (d, J=10.1, H—C(6')), 2.61-2.49 (m, H—C(7')), 1.12 (d, J=5.9, MeC(3)), 0.91 (d, J=6.8, MeC(7)).

$^{13}$C-NMR (100 MHz, CDCl$_3$): δ214.16 (s, CO), 132.91 (d, C(8')), 124.40 (d, C(9')), 62.66 (d, C(6')), 44.71 (s, C(5')), 39.55 (t), 38.32 (t), 33.40 (d, C(7')), 32.43 (d), 30.18 (t), 24.47 (t), 23.70 (t), 21.90 (d), 19.97 (q), 19.17 (t), 18.34 (q).

MS (EI): 232 (4), 217 (1), 203 (1), 175 (1), 149 (13), 134 (18), 119 (9), 107 (6), 106 (5), 105 (8), 93 (6), 91 (11), 83 (100), 79 (9), 77 (6), 67 (6), 55 (22), 41 (8), 29 (4).

Example 18

Ethyl 7-methylspiro[4.5]dec-7-ene-6-carboxylate

At −20° C., a solution of ethyl 9-hydroxy-7-methylspiro[4.5]dec-7-ene-6-carboxylate (1.5 g, 6.3 mmol, cis/trans 34:66, prepared as described in example 16) in dichloromethane was treated with successively with triethylsilane (3.66 g, 31.5 mmol) and with BF$_3$.OEt$_2$ (1.34 g, 9.4 mmol). The resulting solution was stirred for 45 min., poured into an ice-cold 2M aqueous NaOH solution (50 ml), and extracted twice with MTBE (40 ml). The organic phases were washed with water (40 ml), with a saturated aqueous solution of NaCl (40 ml), dried (MgSO$_4$) and concentrated. FC (100 g SiO$_2$, hexane/MTBE 25:1) of the crude product (1.28 g) gave ethyl 7-methylspiro[4.5]dec-7-ene-6-carboxylate (0.98 g, 70%).

Example 19 rel-(6S,7S)-Ethyl 7-methylspiro[4.5]dec-9-ene-6-carboxylate a) cis-Ethyl 7-methyl-9-oxospiro[4.5]decane-6-carboxylate

A solution of ethyl 7-methyl-9-oxospiro[4.5]dec-7-ene-6-carboxylate (2.5 g, 10.6 mmol, prepared as described in Example 16) in hexane (40 ml) was treated with 10% Pd/C (0.5 g) and hydrogenated (10 bar) for 1.5 h. The resulting mixture was filtered and concentrated to give cis-ethyl 7-methyl-9-oxospiro[4.5]decane-6-carboxylate (2.29, 91%).

$^1$H-NMR (400 MHz, CDCl$_3$): δ4.20 (q, J=7.1, CH$_2$O), 2.93 (br. d, J=13.9, H—C(10')), 2.72 (t, J=13.1, H—C(8')), 2.43 (br. d, J=4.2, H—C(6')), 2.29-2.14 (m, 2 H), 2.08 (td, J=1.5, 13.8, H—C(10')), 1.77-1.56 (m, 5 H), 1.56-1.47 (m, 1 H), 1.45-1.36 (m, 1 H), 1.35-1.25 (m, 1 H), 1.30 (t, J=7.1, MeCH$_2$O), 1.02 (d, J=6.6, MeC(7)).

$^{13}$C-NMR (100 MHz, CDCl$_3$): δ211.48 (s, C(9')O), 173.35 (s, CO$_2$), 60.03 (t, OCH$_2$), 54.95 (d, C(6')), 48.26 (s, C(5')), 47.68 (t), 45.06 (t), 38.48 (t), 37.62 (t), 32.35 (d, C(7')), 23.86 (t), 23.59 (t), 19.48 (q), 14.40 (q).

MS (EI): 239 (10), 238 (63), 223 (4), 209 (77), 196 (19), 193 (16), 192 (11), 165 (100), 164 (80), 156 (17), 155 (31), 154 (37), 149 (31), 147 (33), 135 (40), 128 (71), 126 (33), 124 (37), 123 (63), 122 (40), 109 (86), 95 (55), 93 (35), 91 (25), 82 (21), 81 (69), 73 (2), 69 (92), 67 (71), 55 (76), 53 (37), 41 (74), 39 (32), 29 (48).

IR: ν$_{max}$ 2957, 2873, 1711, 1455, 1417, 1378, 1346, 1301, 1279, 1231, 1162, 1146, 1095, 1027, 954, 914, 882 cm$^{-1}$.

b) rel-(6S,7S,9S)- and rel-(6S,7S,9R)-Ethyl 9-hydroxy-7-methylspiro[4.5]decane-6-carboxylate At 5° C., NaBH$_4$ (0.26 g, 6.5 mmol) in methanol (25 ml) was treated with a solution of crude cis-ethyl 7-methyl-9-oxospiro[4.5]decane-6-carboxylate (2.2 g, 9.2 mmol) in methanol (10 ml). The resulting mixture was stirred at 20° C. for 4 h, poured into 2N aqueous HCl (30 ml) and ice/water (50 ml), and extracted twice with MTBE (50 ml). The combined organic phases were washed with water (50 ml), with a saturated aqueous solution of NaCl (50 ml), dried (MgSO$_4$) and concentrated. FC (180 g SiO$_2$, hexane/MTBE 2:1) of the crude product (2.07 g, cis,cis/cis,trans 39:61) gave rel-(6S,7S,9S)-ethyl 9-hydroxy-7-methylspiro[4.5]decane-6-carboxylate (cis,trans; 0.82 g, 37%) and rel-(6S,7S,9R)-ethyl 9-hydroxy-7-methylspiro[4.5]decane-6-carboxylate (cis,cis; 0.49 g, 22%).

rel-(6S,7S,9S)-Ethyl 9-hydroxy-7-methylspiro[4.5]decane-6-carboxylate $^1$H-NMR (400 MHz, CDCl$_3$): δ4.19 (quint, J=3.2, H—C (9')), 4.11 (q, J=7.1, CH$_2$O), 2.37 (br. d, J=4.6, H—C(6')), 2.33-2.21 (m, 1 H), 2.13 (t, J=3.4, 14.4, H—C(10')), 1.93 (ddd, J=3.3, 12.6, 14.0, H—C(8')), 1.85-1.35 (m, 10 H), 1.32-1.24 (m, 1 H), 1.26 (t, J=7.1, MeCH$_2$O), 0.92 (d, J=7.0, MeC(7')).
$^{13}$C-NMR (100 MHz, CDCl$_3$): δ173.97 (s, CO), 67.72 (d, C(9')), 59.38 (t, OCH$_2$), 53.98 (d, C(6')), 43.82 (s, C(5')), 39.71 (t), 39.20 (t), 39.03 (t), 36.17 (t), 25.13 (d, C(7')), 24.15 (t), 22.71 (t), 19.76 (q), 14.42 (q).
MS (EI): 240 (1), 238 (1), 222 (7), 209 (1), 195 (4), 193 (3), 183 (3), 176 (21), 167 (4), 165 (6), 155 (16), 149 (88), 148 (100), 134 (36), 127 (8), 121 (11), 119 (13), 115 (21), 109 (33), 108 (61), 93 (54), 81 (35), 79 (34), 69 (23), 67 (39), 55 (32), 45 (4), 41 (34), 29 (22).

rel-(6S,7S,9R)-Ethyl 9-hydroxy-7-methylspiro[4.5]decane-6-carboxylate $^1$H-NMR (400 MHz, CDCl$_3$): δ4.12 (q, J=7.1, CH$_2$O), 3.69 (tt, J=4.7, 11.4, H—C(9')), 2.22 (br. d, J=4.8, H—C(6')), 1.88 (t, J=12.0, H—C(10')), 1.94-1.82 (m, 1 H), 1.79-1.30 (m, 12 H), 1.26 (t, J=7.1, MeCH$_2$O), 0.95 (d, J=7.0, MeC(7')).
$^{13}$C-NMR (100 MHz, CDCl$_3$): δ173.66 (s, CO), 68.34 (d, C(9')), 59.53 (t, OCH$_2$), 54.37 (d, C(6')), 45.90 (s, C(5')), 41.45 (t), 39.26 (t), 38.57 (t), 37.30 (t), 30.25 (d, C(7')), 24.31 (t), 23.43 (t), 19.55 (q), 14.42 (q).
MS (EI): 240 (1), 238 (1), 222 (4), 209 (1), 195 (3), 193 (1), 183 (1), 176 (26), 167 (1), 165 (3), 155 (10), 149 (93), 148 (100), 134 (14), 127 (6), 121 (16), 119 (14), 115 (16), 109 (39), 108 (31), 93 (54), 81 (39), 79 (38), 69 (22), 67 (48), 55 (34), 45 (7), 41 (38), 29 (22).

c) rel-(6S,7S)-Ethyl 7-methylspiro[4.5]dec-9-ene-6-carboxylate

A 64:36 mixture of rel-(6S,7S,9S)- and (6S,7S,9R)-ethyl 9-hydroxy-7-methylspiro[4.5]decane-6-carboxylate (2.4 g, 9.99 mmol) in pyridine (25 ml) was cooled to −10° C. and treated with POCl$_3$ (1 ml, 11 mmol). The resulting mixture was stirred for 16 h while allowing the reaction temperature to slowly reach 25° C., poured into cold 2N aqueous HCl (100 ml), and extracted twice with hexane (70 ml). The combined organic phases were washed with water (50 ml), with a saturated aqueous solution of NaCl (50 ml), dried (MgSO$_4$), and concentrated. FC (200 g SiO$_2$, hexane/MTBE 80:1) of the crude product (1.6 g) gave rel-(6S,7S)-ethyl 7-methylspiro[4.5]dec-9-ene-6-carboxylate (0.51 g, 23%). Boiling point: 90° C. (0.08 mbar).
Odour description: agrestic, Damascone-tike, fruity, slightly aromatic.
$^{13}$C-NMR (100 MHz, CDCl$_3$): δ173.17 (s, CO), 133.39 (d), 124.48 (d), 59.42 (t), 54.09 (d), 46.45 (s), 41.68 (t), 37.40 (t), 30.40 (f), 28.45 (d), 24.05 (t), 23.60 (t), 19.99 (q), 14.42 (q).
MS (EI): 222 (10), 207 (1), 193 (1), 179 (2), 177 (8), 176 (19), 149 (100), 148 (97), 141 (3), 134 (7), 133 (28), 128 (4), 119 (23), 115 (7), 113 (2), 107 (31), 106 (48), 105 (48), 93 (53), 91 (65), 81 (29), 79 (36), 77 (26), 67 (23), 55 (17), 45 (2), 41 (26).

d) rel-(6S,7S)- and rel-(6R,7S)-Ethyl 7-methylspiro[4.5]dec-9-ene-6-carboxylate

A mixture of rel-(6S,7S)-ethyl 7-methylspiro[4.5]dec-9-ene-6-carboxylate and rel-(6S,7S)-ethyl 7-methylspiro[4.5]dec-8-ene-6-carboxylate (0.1 g, 0.45 mmol) in 1-methyl-2-pyrrolidone (1 ml) was treated with KOt-Bu (56 mg, 0.5 mmol). The resulting mixture was stirred at 60° C. for 2 h, treated with KOt-Bu (56 mg, 0.5 mmol), stirred for 1 h, poured into cold 2N aqueous HCl (10 ml), and extracted twice with hexane (20 ml). The combined organic phases were washed with 2N aqueous HCl (10 ml), with water (10 ml), with a saturated aqueous solution of NaCl (10 ml), dried (MgSO$_4$), concentrated, and gave a 38:39:9:14 mixture of rel-(6S,7S)-/rel-(6R,7S)-ethyl 7-methylspiro[4.5]dec-9-ene-6-carboxylate/rel-(6R,7S)-/rel-(6S,7S)-ethyl 7-methylspiro[4.5]dec-8-ene-6-carbon/late (64 mg, 64%).

rel-(6R,7S)-Ethyl 7-methylspiro[4.5]dec-9-ene-6-carboxylate

MS (EI): 222 (10), 207 (1), 193 (1), 179 (2), 177 (9), 176 (9), 149 (100), 148 (97), 141 (5), 134 (8), 133 (19), 128 (6), 119 (17), 115 (11), 113 (2), 107 (31), 106 (32), 105 (38), 93 (55), 91 (53), 81 (30), 79 (35), 77 (23), 67 (20), 55 (15), 45 (2), 41 (25).

Example 20 rel-(6S,7S)-Methyl 7-methylspiro[4.5]dec-9-ene-6-carboxylate a) 7-Methylspiro[4.5]dec-9-ene-6-carboxylic acid A solution of KOH (19.1 g, 289 mmol) in ethanol (60 ml) was treated with rel-(6S,7S)-ethyl 7-methylspiro[4.5]dec-9-ene-6-carboxylate (4.28 g, 19.2 mmol, prepared as described in Example 19) and after refluxing for 3 d, the resulting mixture was poured into cold 2N aqueous NaOH (100 ml), and extracted twice with cyclohexane (50 ml). The combined aqueous phases were acidified with conc. HCl, extracted twice with MTBE (50 ml), and the combined org. phases were washed with water (50 ml), with a saturated aqueous solution of NaCl (50 ml), dried (MgSO$_4$), and concentrated. FC (300 g SiO$_2$, hexane/MTBE 8:1) of the crude product (2.65 g) gave 7-methylspiro[4.5]dec-9-ene-6-carboxylic acid (1.4 g, 37%).
$^{13}$C-NMR (100 MHz, CDCl$_3$): δ179.29 (s, CO), 133.36 (d), 124.53 (d), 54.20 (d), 46.45 (s), 41.76 (t), 37.49 (t), 30.21 (t), 28.30 (d), 24.12 (t), 23.62 (t), 19.99 (q).

b) Methyl 7-methylspiro[4.5]dec-9-ene-6-carboxylate

At 5° C., a solution of 7-methylspiro[4.5]dec-9-ene-6-carboxylic acid (1.4 g, 7.2 mmol) in DMF was treated with $K_2CO_3$ (1.1 g, 7.9 mmol). The resulting mixture was stirred for 30 min., treated with methyl iodide (0.67 ml, 10.8 mmol), stirred at 20° C. for 2 h, poured into cold 2N aqueous HCl (20 ml), and extracted twice with hexane (70 ml). The combined organic phases were washed with water (50 ml), with a saturated aqueous solution of NaCl (50 ml), dried ($MgSO_4$), and concentrated. FC (170 g $SiO_2$, pentane/diethyl ether 80:1) of the crude product (1.4 g) gave rel-(6R,7S)-methyl 7-methylspiro[4.5]dec-9-ene-6-carboxylate (0.15 g, 10%) and rel-(6S,7S)-methyl 7-methylspiro[4.5]dec-9-ene-6-carboxylate (0.53 g, 35%).

rel-(6S,7S)-Methyl 7-methylspiro[4.5]dec-9-ene-6-carboxylate Boiling point: 85° C. (0.09 mbar).

$^{13}$C-NMR (100 MHz, $CDCl_3$): δ173.68 (s, CO), 133.34 (d), 124.50 (d), 54.11 (d), 50.60 (q), 46.41 (s), 41.68 (t), 37.48 (t), 30.34 (t), 28.42 (d), 24.07 (t), 23.62 (t), 20.06 (q).

MS (EI): 208 (9), 193 (1), 177 (5), 176 (18), 149 (100), 148 (95), 141 (6), 134 (8), 133 (29), 127 (5), 119 (25), 114 (6), 107 (38), 106 (46), 105 (49), 93 (54), 91 (67), 82 (3), 81 (26), 79 (37), 77 (27), 67 (24), 55 (17), 41 (27).

Odour description: agrestic, green, Damascone-like, minty.

rel-(6R,7S)-Methyl 7-methylspiro[4.5]dec-9-ene-6-carboxylate $^{13}$C-NMR (100 MHz, $CDCl_3$): δ174.97 (s, CO), 137.18 (d), 121.46 (d), 56.34 (d), 50.98 (q), 46.11 (s), 38.72 (t), 35.06 (t), 33.67 (t), 29.08 (d), 25.72 (t), 24.86 (t), 19.94 (q).

MS (EI): 208 (9), 177 (5), 176 (10), 149 (100), 148 (91), 134 (9), 133 (20), 127 (9), 119 (19), 114 (9), 108 (18), 107 (40), 106 (32), 105 (39), 93 (59), 91 (58), 81 (27), 79 (37), 77 (25), 67 (22), 59 (13), 55 (16), 41 (28).

Example 21

(E)-1-(rel-(6S,7S)-7-Methylspiro[4.5]dec-9-en-6-yl)but-2-en-1-one

At 5° C., a solution of allylmagnesium chloride (12.1 ml, 2 M in THF) was treated dropwise with a solution of rel-(6S,7S)-ethyl 7-methylspiro[4.5]dec-9-ene-6-carboxylate (1.5 g, 6.7 mmol, prepared as described in Example 19) in THF (20 ml), stirred at 20° C. for 1 h, poured into cold 2N aqueous HCl (30 ml), and extracted twice with MTBE (70 ml). The combined organic phases were washed with water (100 ml), with a saturated aqueous solution of NaCl (100 ml), dried ($MgSO_4$), and concentrated. The crude product (1.9 g) was dissolved in DMF (10 ml) and added to a solution of KOt-Bu (1.2 g, 10.7 mmol) in DMF (10 ml). The resulting mixture was stirred for 1 h, poured into cold 2N aqueous HCl (30 ml), and extracted twice with hexane (80 ml). The combined organic phases were washed with water (100 ml), with a saturated aqueous solution of NaCl (100 ml), dried ($MgSO_4$), and concentrated. The crude product (1.9 g) was then dissolved in toluene (15 ml) and treated with PTSA.$H_2O$ (15 mg, 0.077 mmol). The resulting solution was stirred at 60° C. for 2.75 h, poured into cold water (30 ml), and extracted with cyclohexane (20 ml). The combined organic phases were washed with a saturated aqueous solution of NaCl (20 ml), dried ($MgSO_4$), and concentrated. FC (120 g $SiO_2$, hexane/MTBE 25:1) of the crude product (1.38 g) gave (E)-1-(rel-(6S,7S)-7-methylspiro[4.5]dec-9-en-6-yl)but-2-en-1-one (0.63 g, 43%). Boiling point: 115° C. (0.09 mbar).

Odour description: Damascone-like, aromatic.

$^{13}$C-NMR (100 MHz, $CDCl_3$): δ202.47 (s, CO), 141.23 (d), 134.57 (d), 133.91 (d), 124.48 (d), 58.19 (d), 46.62 (s), 42.42 (t), 36.94 (t), 30.65 (t), 29.29 (d), 24.30 (t), 23.58 (t), 20.18 (q), 18.15 (q).

MS (EI): 218 (6), 203 (3), 189 (3), 175 (4), 163 (6), 149 (37), 134 (7), 123 (11), 111 (19), 109 (19), 93 (24), 91 (28), 81 (28), 79 (21), 77 (15), 69 (100), 55 (13), 41 (45).

Example 22

Ethyl 7-methylspiro[4.5]deca-6,8-diene-6-carboxylate a) cis- and trans-Ethyl 9-acetoxy-7-methylspiro[4.5]dec-7-ene-6-carboxylate A mixture of 35:65 cis-/trans-ethyl 9-hydroxy-7-methylspiro[4.5]dec-7-ene-6-carboxylate (0.1 g, 0.42 mmol, prepared as described in Example 16), acetic anhydride (90 mg, 0.88 mmol), and sodium acetate (34.4 mg, 0.42 mmol) was heated at 80° C. for 2 h, cooled to 20° C., poured into ice, and extracted with MTBE (20 ml). The organic phase was washed with a saturated aqueous solution of NaCl, dried ($MgSO_4$) and concentrated. FC ($SiO_2$, hexane/MTBE 10:1) of the crude product (170 mg) gave a 35:65 mixture of cis-/trans-ethyl 9-acetoxy-7-methylspiro[4.5]dec-7-ene-6-carboxylate (50 mg, 43%).

cis-Ethyl 9-acetoxy-7-methylspiro[4.5]dec-7-ene-6-carboxylate $^1$H-NMR (400 MHz, $CDCl_3$): δ5.66 (dquint, J=1.3, 3.0, H—C(8')), 5.33-5.30 (m, H—C(9')), 4.24-4.10 (m, $CH_2O$), 2.79 (br. s, H—C(6')), 2.34 (dd, J=5.8, 14.9, H—C(10')), 2.09 (s, MeCO), 1.74 (td, J=0.4, 1.4, MeC(7')), 1.79-1.31 (m, 9 H), 1.26 (t, J=7.2, $MeCH_2O$).

$^{13}$C-NMR (100 MHz, $CDCl_3$): δ172.35 (s, CO), 170.70 (s, CO), 136.50 (s, C(7')), 122.22 (d, C(8')), 68.12 (d, C(9')), 60.46 (t, $OCH_2$), 55.30 (d, C(6')), 42.92 (s, C(5')), 37.98 (t), 37.19 (t), 34.75 (t), 23.74 (t), 23.30 (t), 23.02 (q), 21.30 (q), 14.21 (q).

MS (EI): 280 (1), 238 (1), 220 (5), 209 (4), 206 (12), 193 (1), 175 (3), 165 (12), 164 (58), 147 (65), 131 (10), 122 (18), 105 (100), 91 (26), 79 (14), 77 (15), 67 (8), 60 (4), 55 (7), 43 (20), 29 (14).

trans-Ethyl 9-acetoxy-7-methylspiro[4.5]dec-7-ene-6-carboxylate $^1$H-NMR (400 MHz, $CDCl_3$): δ5.59-5.57 (m, H—C(8)), 5.37-5.32 (m, H—C(9')), 4.24-4.10 (m, $CH_2O$), 2.67 (br. s, H—C(6')), 2.14 (dd, J=10.1, 12.5, H—C(10')), 2.06 (s, MeCO), 1.70 (tm, J=0.4, 1.6, MeC(7')), 1.79-1.31 (m, 9 H), 1.28 (t, J=7.2, $MeCH_2O$).

$^{13}$C-NMR (100 MHz, $CDCl_3$): δ172.74 (s, CO), 171.07 (s, CO), 134.87 (s, C(7')), 124.14 (d, C(8')), 69.50 (d, C(9')), 60.51 (t, $OCH_2$), 55.28 (d, C(6')), 45.26 (s, C(5')), 37.86 (t), 37.09 (t), 34.03 (t), 23.68 (t), 23.35 (t), 22.62 (q), 21.28 (q), 14.24 (q).

MS (EI): 280 (1), 238 (2), 220 (5), 209 (5), 206 (18), 193 (6), 165 (16), 164 (82), 147 (63), 131 (10), 122 (21), 105 (100), 91 (26), 79 (15), 77 (14), 67 (8), 60 (3), 55 (8), 43 (26), 29 (14).

b) Ethyl 7-methylspiro[4.5]deca-6,8-diene-6-carboxylate

A solution of a 30:70 mixture of cis-/trans-ethyl 9-acetoxy-7-methylspiro[4.5]dec-7-ene-6-carboxylate (2.7 g, 9.6 mmol) in DBU (15 ml, 97 mmol) was stirred for 4 d at 20° C. The reaction mixture was poured into cold 2N aqueous HCl (50 ml), and extracted twice with MTBE (50 ml). The combined organic phases were washed with 2N aqueous HCl (30 ml), with water (40 ml), with a saturated aqueous solution of NaCl (40 ml), dried (MgSO$_4$), and concentrated. FC (250 g SiO$_2$, pentane/Et$_2$O 100:1) of the crude product (1.8 g) gave methyl 7-methylspiro[4.5]deca-6,8-diene-6-carboxylate (0.54 g, 25%).

Boiling point: 96° C. (0.08 mbar).

Odour description: ethyl safranate-like, fruity, floral, agrestic, herbaceous.

Example 23

Methyl 7-methylspiro[4.5]deca-6,8-diene-6-carboxylate

A 33:67 cis-/trans-ethyl 9-hydroxy-7-methylspiro[4.5] dec-7-ene-6-carboxylate (38 g, 0.16 mol, prepared as described in Example 16) was added to a solution of KOH (52.6 g, 0.8 mol) in ethanol (300 ml). The resulting mixture was stirred for 2 h at reflux, poured into cold 2N aqueous NaOH (100 ml), and extracted twice with MTBE (100 ml). The combined organic phases were washed with 2N aqueous NaOH (50 ml), the combined aqueous phases were acidified with conc. HCl, extracted twice with MTBE (150 ml), and the combined organic phases were washed with water (100 ml), with a saturated aqueous solution of NaCl (100 ml), dried (MgSO$_4$), and concentrated, giving crude trans-9-hydroxy-7-methylspiro[4.5]dec-7-ene-6-carboxylic acid (22.7 g).

$^{13}$C-NMR (100 MHz, CDCl$_3$): δ177.37 (s, CO), 132.55 (s), 128.65 (d), 66.40 (d), 55.20 (d), 45.52 (s, C(5')), 38.04 (t), 38.02 (t), 37.09 (t), 23.62 (t), 23.32 (t), 22.68 (q).

MS (EI): 210 (1), 192 (2), 181 (8), 165 (2), 148 (28), 147 (7), 133 (9), 119 (16), 106 (76), 105 (100), 91 (72), 79 (19), 77 (21), 65 (11), 44 (20).

At 5° C., a solution of the crude trans-9-hydroxy-7-methylspiro[4.5]dec-7-ene-6-carboxylic acid obtained (22.7 g) in DMF (150 ml) was treated with potassium carbonate (16.3 g, 118 mmol) and stirred for 30 min. The resulting mixture was then treated within 6 min. with methyl iodide (13.4 ml, 215 mmol), stirred for 2 h at 20° C., poured into cold 2N aqueous HCl (200 ml), and extracted twice with hexane (150 ml). The combined organic phases were washed with water (100 ml), with a saturated aqueous solution of NaCl (150 ml), dried (MgSO$_4$), and concentrated, giving crude trans-methyl 9-hydroxy-7-methylspiro[4.5]dec-7-ene-6-carboxylate (12.85 g, 36%).

$^{13}$C-NMR (100 MHz, CDCl$_3$): δ173.82 (s, CO), 132.43 (s), 128.88 (d), 66.32 (d), 55.34 (d), 51.61 (q, OMe), 45.63 (s, C(5')), 38.58 (t), 38.00 (t), 37.08 (t), 23.63 (t), 23.32 (t), 22.63 (q).

A part of the crude trans-methyl 9-hydroxy-7-methylspiro[4.5]dec-7-ene-6-carboxylate obtained (4.0 g) was treated with acetic anhydride (3.5 ml, 37.4 mmol) and sodium acetate (1.46 g, 17.8 mmol). The resulting mixture was stirred at 80° C. for 4 h, poured into cold 2N aqueous NaOH (20 ml), and extracted twice with MTBE (30 ml). The combined organic phases were washed with water (30 ml), with a saturated aqueous solution of NaCl (30 ml), dried (MgSO$_4$), concentrated giving crude trans-methyl 9-acetoxy-7-methylspiro[4.5]dec-7-ene-6-carboxylate (4.4 g, 92%).

$^{13}$C-NMR (100 MHz, CDCl$_3$): δ173.20 (s), 170.97 (s), 134.76 (s), 124.27 (d), 69.43 (d), 55.27 (d), 51.66 (q, OMe), 45.22 (s, C(5')), 37.95 (t), 37.08 (t), 34.05 (t), 23.71 (t), 23.37 (t), 22.70 (q), 21.32 (q).

A part of the crude trans-methyl 9-acetoxy-7-methylspiro [4.5]dec-7-ene-6-carboxylate obtained (2.4 g) was dissolved in DBU (13 g, 85.6 mmol) and stirred for 21 h at 20° C. and for 7 h at 40° C. The reaction mixture was poured into cold 2N aqueous HCl (60 ml), and extracted twice with cyclohexane (50 ml). The combined organic phases were washed with water (50 ml), with a saturated aqueous solution of NaCl (50 ml), dried (MgSO$_4$), and concentrated. FC (500 g SiO$_2$, pentane/Et$_2$O 100:1) of the crude product (1.47 g) gave methyl 7-methylspiro[4.5]deca-6,8-diene-6-carboxylate (0.77 g, 13% estimated overall yield). Boiling point: 100° C. (0.08 mbar).

Odour description: floral, fruity, green, mossy, balsamic.

$^{13}$C-NMR (100 MHz, CDCl$_3$): δ170.52 (s, CO), 132.90 (s), 132.54 (s), 128.68 (d), 128.50 (d), 50.93 (t, OMe), 44.39 (s, C(5')), 36.61 (t), 35.81 (t, 2 C), 24.17 (t, 2 C), 19.73 (q).

MS (EI): 206 (15), 175 (34), 163 (19), 147 (40), 146 (27), 145 (75), 133 (10), 132 (20), 131 (14), 119 (18), 105 (100), 91 (37), 77 (23), 65 (12), 59 (10), 41 (12), 39 (11).

Example 24

Methyl 7-methylenespiro[4.5]dec-8-ene-6-carboxylate

A solution of crude trans-methyl 9-hydroxy-7-methylspiro [4.5]dec-7-ene-6-carboxylate (4.0 g, 17.8 mmol, prepared as described in the Example 23) in THF (40 ml) was treated with water (0.32 ml, 17.8 mmol) and conc. sulphuric acid (0.29 ml, 5.3 ml). The resulting mixture was stirred for 8 h at 60° C., poured into cold 2N aqueous NaOH (30 ml), and extracted twice with cyclohexane (60 ml). The combined organic phases were washed with water (60 ml), with a saturated aqueous solution of NaCl (60 ml), dried (MgSO$_4$), and concentrated. FC (500 g SiO$_2$, pentane/Et$_2$O 80:1) of the crude product (2.9 g) gave a 84:16 mixture of methyl 7-methylenespiro[4.5]dec-8-ene-6-carboxylate/methyl 7-methylspiro [4.5]deca-6,8-diene-6-carboxylate (1.15 g, 31%, 27% estimated four-step overall yield). Boiling point: 95° C. (0.07 mbar).

Odour description: agrestic, spicy, fruity, floral, woody.

Data of methyl 7-methylenespiro[4.5]dec-8-ene-6-carboxylate $^{13}$C-NMR (100 MHz, CDCl$_3$): δ173.15 (s, CO), 140.33 (s), 129.89 (d), 127.35 (d), 114.94 (t), 55.59 (d, C(6')), 51.43 (q, OMe), 43.68 (s, C(5')), 38.35 (t), 37.61 (t), 35.11 (t), 24.44 (t), 24.14 (t), 19.73 (q).

MS (EI): 206 (5), 175 (2), 163 (3), 147 (73), 131 (15), 119 (8), 118 (10), 117 (10), 105 (100), 91 (27), 79 (17), 77 (17), 65 (9), 59 (8), 41 (11), 39 (9).

Example 25

Methyl 7-methylspiro[4.5]dec-7-ene-6-carboxylate

At −30° C., a solution of crude trans-methyl 9-hydroxy-7-methylspiro[4.5]dec-7-ene-6-carboxylate (1.1 g, 4.9 mmol, prepared as described in the Example 23) in dichloromethane (10 ml) was treated with triethylsilane (4.0 ml, 24.5 mmol) and with BF$_3$.OEt$_2$ (0.92 ml, 7.4 mmol). The resulting mixture was stirred for 45 min. while allowing the temperature to reach 0° C., poured into cold 2N aqueous NaOH (50 ml), and extracted twice with MTBE (25 ml). The combined organic phases were washed with water (25 ml), with a saturated aqueous solution of NaCl (25 ml), dried (MgSO$_4$), and concentrated. FC (55 g SiO$_2$, hexane/MTBE 40:1) of the crude product (1 g) gave methyl 7-methylspiro[4.5]dec-7-ene-6-carboxylate (0.92 g, 90%). Boiling point: 98° C. (0.07 mbar).

Odour description: fruity, woody, agrestic.

$^{13}$C-NMR (100 MHz, CDCl$_3$): δ174.48 (s, CO), 130.01 (s), 124.59 (d), 55.76 (d, C(6')), 51.38 (q, OMe), 43.76 (s, C(5')), 37.76 (t), 36.61 (t), 28.23 (t), 24.01 (t), 23.92 (t), 23.12 (t), 23.09 (q).

MS (EI): 208 (22), 193 (2), 176 (10), 149 (86), 148 (100), 134 (16), 127 (34), 125 (23), 119 (14), 114 (21), 107 (31), 106 (40), 105 (37), 95 (36), 93 (33), 91 (50), 81 (43), 79 (36), 77 (25), 67 (36), 59 (9), 55 (15), 53 (14), 41 (25), 39 (14).

Example 26

Methyl 7-methylspiro[4.5]dec-6-ene-6-carboxylate a) Methyl 1-methyl-7-oxaspiro[bicyclo[4.1.0]heptane-3,1'-cyclopentane]-2-carboxylate At 5° C., a solution of methyl 7-methylspiro[4.5]dec-7-ene-6-carboxylate (13.5 g, 60 mmol, prepared as described in Example 25) in dichloromethane (150 ml) was treated with MCPBA (17.8 g, 72 mmol). The resulting mixture was stirred for 4 h at 20° C., filtered, and the organic phase was washed with water (100 ml), dried (MgSO$_4$), concentrated, and gave crude methyl 1-methyl-7-oxaspiro[bicyclo[4.1.0]heptane-3,1'-cyclopentane]-2-carboxylate (13 g). Boiling point: 130° C. (0.08 mbar).

$^{13}$C-NMR (100 MHz, CDCl$_3$): δ171.48 (s, CO), 59.56 (d), 57.59 (s), 53.45 (d), 51.23 (q), 41.94 (s), 37.17 (t), 36.18 (t), 25.92 (t), 24.62 (q), 24.49 (t), 23.97 (t), 22.07 (t).

MS (EI): 224 (1), 209 (1), 206 (1), 168 (15), 165 (13), 147 (19), 125 (46), 114 (37), 105 (23), 93 (45), 79 (58), 67 (66), 59 (89), 58 (100), 43 (91), 41 (54).

b) The crude methyl 1-methyl-7-oxaspiro[bicyclo[4.1.0]heptane-3,1'-cyclopentane]-2-carboxylate obtained (13 g) was added to a solution of sodium (1.5 g, 64 mmol) in methanol (100 ml) and the resulting mixture was refluxed for 10 h, poured into cold 2N aqueous HCl (100 ml), and extracted twice with MTBE (100 ml). The combined organic phases were washed with water (100 ml), twice with a saturated aqueous solution of NaCl (100 ml), dried (MgSO$_4$), concentrated, and gave crude gave methyl 8-hydroxy-7-methylspiro[4.5]dec-6-ene-6-carboxylate (5.65 g) which was dissolved in dichloromethane (80 ml) and treated at −30° C. with triethylsilane (14.4 ml, 0.1 mol) and with BF$_3$.OEt$_2$ (4.7 ml, 37.8 mmol). The resulting mixture was stirred for 3 h while allowing the temperature to reach 20° C., poured into cold 2N aqueous NaOH (80 ml), and extracted twice with MTBE (100 ml). The combined organic phases were washed with water (100 ml), with a saturated aqueous solution of NaCl (100 ml), dried (MgSO$_4$), and concentrated. FC (90 g SiO$_2$, hexane/MTBE 95:5) of the crude product (2.05 g) gave methyl 7-methylspiro[4.5]dec-6-ene-6-carboxylate (1.16 g, 42% three-step overall yield). Boiling point: 105° C. (0.08 mbar).

Odour description: fruity, damascone-like, leather, woody.

$^{13}$C-NMR (100 MHz, CDCl$_3$): δ171.41 (s), 134.65 (s), 134.34 (s), 51.06 (q, OMe), 44.33 (s, C(5')), 38.10 (t, 2 C), 35.57 (t), 31.04 (t), 24.83 (t, 2 C), 21.54 (q), 31.04 (t).

MS (EI): 208 (6), 193 (1), 179 (9), 177 (10), 166 (29), 149 (100), 134 (24), 119 (12), 107 (23), 105 (19), 93 (19), 91 (30), 81 (8), 79 (17), 77 (15), 67 (8), 59 (7), 55 (9), 41 (12).

Example 27

Ethyl 7-methylspiro[4.5]dec-6-ene-6-carboxylate

Prepared from ethyl 7-methylspiro[4.5]dec-7-ene-6-carboxylate (prepared as described in Example 14), as described for the preparation of methyl 7-methylspiro[4.5]dec-6-ene-6-carboxylate from methyl 7-methylspiro[4.5]dec-7-ene-6-carboxylate (Example 26), via crude ethyl 1-methyl-7-oxaspiro[bicyclo[4.1.0]heptane-3,1'-cyclopentane]-2-carboxylate (MCPBA, CH$_2$Cl$_2$), transformed into crude ethyl 8-hydroxy-7-methylspiro[4.5]dec-6-ene-6-carboxylate (NaOEt, reflux, 4 h) that was reduced using triethylsilane and BF$_3$.OEt$_2$ in dichloromethane (64% overall yield after FC (400 g SiO$_2$, hexane/MTBE 40:1)).

Ethyl 1-methyl-7-oxaspiro[bicyclo[4.1.0]heptane-3, 1'-cyclopentane]-2-carboxylate Boiling point: 135° C. (0.07 mbar).

$^{13}$C-NMR (100 MHz, CDCl$_3$): δ170.94 (s, CO), 60.00 (t, OCH$_2$), 59.55 (d, C(8')), 57.65 (s, C(7')), 53.44 (d, C(6')), 41.91 (s, C(5')), 37.17 (t), 37.01 (t), 25.94 (t), 24.66 (q), 24.51 (t), 23.99 (t), 22.10 (t), 14.33 (q).

MS (EI): 238 (1), 223 (2), 222 (2), 220 (2), 210 (3), 209 (5), 193 (17), 182 (24), 165 (20), 155 (13), 147 (39), 143 (31), 135 (18), 128 (26), 125 (40), 122 (24), 111 (47), 105 (38), 97 (44), 93 (56), 91 (45), 85 (41), 83 (44), 81 (53), 79 (75), 77 (37), 73 (52), 72 (84), 67 (69), 55 (46), 45 (12), 43 (100), 41 (59), 29 (45).

Ethyl 8-hydroxy-7-methylspiro[4.5]dec-6-ene-6-carboxylate $^{13}$C-NMR (100 MHz, CDCl$_3$): δ170.61 (s, CO), 137.62 (s, C(7')), 134.08 (s, C(6')), 68.49 (d, C(8')), 60.38 (t, OCH$_2$), 44.72 (s, C(5')), 37.90 (t), 36.62 (t), 31.68 (t), 29.10 (t), 24.78 (t), 24.65 (t), 17.78 (q), 14.18 (q).

MS (EI): 238 (13), 223 (18), 220 (3), 209 (6), 193 (47), 192 (49), 181 (7), 177 (18), 165 (100), 163 (62), 156 (45), 149 (34), 147 (51), 135 (37), 122 (38), 121 (42), 110 (50), 107 (34), 105 (59), 93 (35), 91 (59), 82 (14), 81 (25), 79 (51), 77 (43), 67 (30), 55 (33), 43 (49), 29 (31).

Ethyl 7-methylspiro[4.5]dec-6-ene-6-carboxylate (Boiling point: 100° C. (0.08 mbar)).

$^{13}$C-NMR (100 MHz, CDCl$_3$): δ170.94 (s), 134.48 (s), 134.21 (s), 60.02 (t, OCH$_2$), 44.37 (s, C(5')), 38.05 (t, 2C), 35.65 (t), 31.05 (t), 24.88 (t, 2C), 21.39 (q), 19.50 (t), 14.30 (q).

MS (EI): 208 (1), 193 (3), 180 (14), 179 (2), 177 (14), 166 (1), 149 (100), 134 (9), 119 (7), 107 (16), 105 (12), 93 (20), 91 (21), 81 (8), 79 (14), 77 (11), 67 (8), 59 (1), 55 (7), 41 (9).

Odour description: fruity, floral, agrestic, ethyl safranate-like

Example 28

Ethyl 7-methylenespiro[4.5]decane-6-carboxylate a) 7-methylenespiro[4.5]decane-6-carboxylic acid A solution of KOH (47.5 g, 0.72 mol) in EtOH (200 ml) was treated with methyl 7-methylspiro[4.5]dec-6-ene-6-carboxylate (15 g, 0.072 mol, prepared as described in Example 26) and the resulting mixture was stirred at reflux for 6 h, poured into cold 2N aqueous NaOH (300 ml), and extracted twice with cyclohexane (100 ml). The combined organic phases were washed with 2N aqueous NaOH (100 ml), and the combined aqueous phases were acidified with conc. HCl, and extracted twice with MTBE (150 ml). The combined organic phases were washed with water (100 ml), with a saturated aqueous solution of NaCl (150 ml), dried (MgSO$_4$), and concentrated. FC (90 g SiO$_2$, hexane/MTBE 88:12) of the crude product (12.8 g) gave 7-methylenespiro[4.5]decane-6-carboxylic acid (0.7 g, 5%) and 7-methylspiro[4.5]dec-7-ene-6-carboxylic acid (0.57 g, 4%).

7-methylenespiro[4.5]decane-6-carboxylic acid $^{13}$C-NMR (100 MHz, CDCl$_3$): δ178.99 (s), 144.81 (s), 112.37 (t), 58.60 (d), 46.29 (s, C(5')), 38.16 (t), 36.65 (t), 32.83 (t), 31.31 (t), 24.32 (t), 24.13 (t), 23.76 (t).

MS (EI): 194 (25), 179 (3), 176 (5), 149 (100), 148 (40), 134 (19), 119 (10), 113 (36), 111 (27), 107 (32), 106 (20), 105 (31), 95 (60), 93 (40), 91 (52), 82 (28), 81 (46), 79 (44), 77 (31), 67 (78), 55 (24), 53 (22), 45 (6), 41 (40), 39 (23).

7-Methylspiro[4.5]dec-7-ene-6-carboxylic acid $^{13}$C-NMR (100 MHz, CDCl$_3$): δ179.75 (s), 129.73 (s), 125.02 (d), 55.50 (d), 43.64 (s, C(5')), 37.84 (t), 36.63 (t), 27.95 (t), 24.00 (t), 23.89 (t), 23.14 (d), 23.10 (t).

MS (EI): 194 (9), 179 (3), 176 (4), 149 (45), 148 (22), 134 (31), 125 (9), 119 (7), 113 (13), 111 (12), 107 (17), 105 (13), 95 (100), 94 (28), 93 (26), 91 (33), 82 (15), 81 (21), 79 (41), 77 (23), 67 (49), 55 (20), 53 (19), 45 (4), 41 (34), 39 (20).

b) Ethyl 7-methylenespiro[4.5]decane-6-carboxylate

At 5° C., a solution of the previously obtained 7-methylenespiro[4.5]decane-6-carboxylic acid (1.2 g, 6.2 mmol) in DMF (30 ml) was treated with K$_2$CO$_3$ (0.94 g, 6.8 mmol). The resulting mixture was stirred for 30 min., treated with ethyl iodide (0.75 ml, 9.3 mmol), stirred at 20° C. for 2 h, poured into cold 2N aqueous HCl (20 ml), and extracted twice with hexane (50 ml). The combined organic phases were washed with water (50 ml), with a saturated aqueous solution of NaCl (50 ml), dried (MgSO$_4$), and concentrated. FC (90 g SiO$_2$, hexane/MTBE 98:2) of the crude product (1.23 g) gave ethyl 7-methylenespiro[4.5]decane-6-carboxylate (0.69 g, 50%). Boiling point: 90° C. (0.08 mbar).

Odour description: fruity, orris, damascone, floral, green, agrestic.

$^{13}$C-NMR (100 MHz, CDCl$_3$): δ172.74 (s), 145.42 (s), 111.44 (t), 59.94 (t), 58.76 (d), 46.51 (s, C(5')), 37.85 (t), 36.69 (t), 33.21 (t), 31.57 (t), 24.37 (t), 24.22 (t), 23.90 (t), 14.24 (q).

MS (EI): 222 (13), 207 (2), 193 (3), 180 (4), 176 (9), 149 (87), 148 (100), 141 (15), 134 (32), 128 (40), 119 (13), 113 (15), 107 (27), 106 (28), 105 (25), 95 (45), 94 (22), 93 (33), 91 (48), 81 (41), 79 (53), 77 (26), 67 (47), 55 (22), 53 (19), 41 (32), 29 (20).

Example 29

Methyl 7-methylenespiro[4.5]decane-6-carboxylate

At 5° C., a solution of the previously obtained 7-methylenespiro[4.5]decane-6-carboxylic acid (1.1 g, 5.66 mmol, prepared as described in Example 28) in DMF (20 ml) was treated with K$_2$CO$_3$ (0.86 g, 6.8 mmol). The resulting mixture was stirred for 30 min., treated with methyl iodide (0.53 ml, 8.5 mmol), stirred at 20° C. for 2 h, poured into cold 2N aqueous HCl (30 ml), and extracted twice with hexane (30 ml). The combined organic phases were washed with water (50 ml), with a saturated aqueous solution of NaCl (50 ml), dried (MgSO$_4$), and concentrated. FC (30 g SiO$_2$, hexane/MTBE 50:1) of the crude product (1 g) gave methyl 7-methylenespiro[4.5]decane-6-carboxylate (0.84 g, 71%). Boiling point: 90° C. (1.1 mbar).

Odour description: fruity, agrestic, spicy.

$^{13}$C-NMR (100 MHz, CDCl$_3$): δ173.17 (s), 145.33 (s), 111.55 (t), 58.64 (d), 51.21 (g), 46.51 (s, C(5')), 37.95 (t), 36.65 (t), 33.16 (t), 31.53 (t), 24.38 (t), 24.23 (t), 23.90 (t).

MS (EI): 208 (13), 176 (13), 149 (80), 148 (100), 134 (41), 127 (27), 125 (19), 119 (15), 114 (67), 107 (30), 106 (27), 105 (27), 95 (70), 94 (29), 93 (34), 91 (53), 81 (36), 79 (60), 77 (32), 67 (54), 59 (16), 55 (25), 53 (24), 41 (38), 39 (21).

Example 30

(E)-1-(7-Methylenespiro[4.5]decan-6-yl)but-2-en-1-one

Ethyl 7-methylenespiro[4.5]decane-6-carboxylate (2.65 g, 11.9 mmol, prepared as described in Example 28) was transformed into the intermediate 1-(7-methylenespiro[4.5]decan-6-yl)but-3-en-1-one as described in the synthesis of (E)-1-(rel-(6S,7S)-7-methylspiro[4.5]dec-9-en-6-yl)but-2-en-1-one (Example 21) by allylmagnesium chloride addition followed by treatment of the crude product with KOt-Bu in DMF leading to 1-(7-methylenespiro[4.5]decan-6-yl)but-3-en-1-one (1.2 g, 46%) and (E)-1-(7-methylenespiro[4.5]decan-6-yl)but-2-en-1-one (0.26 g, 10%) after FC. A solution of 1-(7-methylenespiro[4.5]decan-6-yl)but-3-en-1-one (0.95 g, 4.35 mmol) and PTSA.H$_2$O (41 mg, 0.22 mmol) in MTBE (20 ml) was heated at 40° C. for 24 h, treated with PTSA.H$_2$O (41 mg, 0.22 mmol), and further heated at 40° C. for 24 h. The addition of PTSA.H$_2$O was repeated six times every 24 h. The resulting mixture was then poured into cold water (20 ml) and aqueous 2M NaOH (3 drops) and the aqueous phase was extracted with MTBE (20 ml). The combined organic phases were washed with a saturated aqueous solution of NaCl (20 ml), dried (MgSO$_4$), and concentrated. FC (90 g SiO$_2$, pentane/Et$_2$O 100:1) of the crude product (0.91 g) gave 1-(7-methylenespiro[4.5]decan-6-yl)but-3-en-1-one (0.24 g, 25%) and (E)-1-(7-methylenespiro[4.5]decan-6-yl)but-2-en-1-one (0.39 g, 41%).

(E)-1-(7-Methylenespiro[4.5]decan-6-yl)but-2-en-1-one

Boiling point: 110° C. (0.09 mbar)

$^{13}$C-NMR (100 MHz, CDCl$_3$): δ199.43 (s), 146.07 (s), 141.56 (d), 131.93 (d), 111.94 (t), 64.17 (d), 46.78 (s, C(5')), 38.28 (t), 37.23 (t), 33.28 (t), 31.56 (t), 24.71 (t), 24.30 (t), 24.17 (t), 18.04 (q).

MS (EI): 218 (10), 149 (27), 134 (32), 121 (9), 109 (11), 107 (15), 93 (12), 91 (18), 81 (21), 79 (17), 77 (11), 69 (100), 55 (9), 41 (31).

Odour description: fruity, spicy, agrestic, orris, ethyl safranate-like.

Example 31

(E)-1-(7-Methylspiro[4.5]deca-6,8-dien-6-yl)but-2-en-1-one a) 10-Acetyl-9-methylspiro[4.5]dec-8-en-7-one In a Dean-Stark apparatus, a mixture of 1-cyclopentylidenepropan-2-one/1-cyclopentenylpropan-2-one (25:75, 600 g, 4.83 mol), acetylacetone (493 g, 4.83 mol), and zinc chloride (164.6 g, 1.21 mol) in benzene (500 ml) and heptane (500 ml) was heated at reflux for 2.5 d (44 ml water collected). The reaction mixture was poured into ice/water (1.5 l) and extracted with cyclohexane (0.6 l). The organic phase was washed with water (1 l), with a saturated aqueous solution of NaHCO$_3$ (0.5 l), twice with a saturated aqueous solution of NaCl (1 l and 0.5 l), dried (100 g MgSO$_4$), and concentrated (till 60° C./30 mbar). Vigreux-Distillation (0.08 mbar, bath temperature 180° C., head temp. 120-130° C.) of the crude product (615 g) followed by FC (2 kg SiO$_2$, hexane/MTBE 2:1) gave 10-acetyl-9-methylspiro[4.5]dec-8-en-7-one (20.7 g, 2.1%). Boiling point: 150° C. (0.09 mbar).

$^{13}$C-NMR (100 MHz, CDCl$_3$): δ206.40 (s, COMe), 199.02 (s, C(7)O), 156.23 (s, C(9)), 127.96 (d, C(8)), 64.36 (d, C(10)), 47.30 (s, C(5)), 43.95 (t), 39.04 (t), 37.13 (t), 33.01 (q), 24.10 (q), 23.58 (t), 23.07 (t).

MS (EI): 206 (1), 191 (1), 164 (38), 149 (4), 135 (8), 122 (100), 121 (16), 107 (13), 91 (12), 77 (10), 67 (5), 43 (27).

b) 1-(9-Hydroxy-7-methylspiro[4.5]dec-7-en-6-yl)ethanone

A solution of 10-acetyl-9-methylspiro[4.5]dec-8-en-7-one (8.8 g, 42.7 mmol) in methanol (90 ml) was treated with anhydrous cerium trichloride (10.5 g, 27.3 mmol). The resulting mixture was stirred for 30 min., cooled to −65° C., and treated within 20 min. with sodium borohydride (0.84 g, 21.3 mmol) in methanol (60 ml). The resulting mixture was stirred for 45 min. at −65° C., poured into 2N aqueous HCl and ice, and extracted twice with MTBE (100 ml). The combined organic phases were washed with water (100 ml), aqueous solution of NaCl (80 ml), dried (MgSO$_4$) and concentrated. FC(SiO$_2$, hexane/MTBE 3:1) of the crude product (8.0 g) gave a 8:92 mixture of cis/trans-1-(9-hydroxy-7-methylspiro[4.5]dec-7-en-6-yl)ethanone (5.31 g, 60%).

trans-1-(9-Hydroxy-7-methylspiro[4.5]dec-7-en-6-yl)ethanone $^{13}$C-NMR (100 MHz, CDCl$_3$): δ210.53 (s), 133.32 (s), 128.57 (d), 66.23 (d), 62.95 (d), 45.90 (s), 38.44 (t), 37.95 (t), 37.48 (t), 31.85 (q), 23.32 (t), 23.19 (t), 23.02 (q).

MS (EI): 208 (1), 193 (3), 175 (1), 165 (5), 148 (25), 147 (24), 133 (10), 125 (38), 119 (17), 106 (90), 105 (100), 91 (40), 81 (11), 79 (19), 77 (17), 67 (12), 55 (15), 43 (54).

c) 10-Acetyl-9-methylspiro[4.5]dec-8-en-7-ylacetate

A mixture of 8:92 cis/trans-1-(9-hydroxy-7-methylspiro[4.5]dec-7-en-6-yl)ethanone (4.2 g, 20.2 mmol) was treated with acetic anhydride (4 ml, 42.3 mmol) and sodium acetate (1.65 g, 20.2 mmol). The resulting mixture was stirred at 80° C. for 1 h, poured into cold 2N aqueous NaOH (50 ml), and extracted twice with MTBE (40 ml). The combined organic phases were washed with water (40 ml), with a saturated aqueous solution of NaCl (40 ml), dried (MgSO$_4$), and concentrated. FC (300 g SiO$_2$, hexane/MTBE 8:1) of the crude product (4.82 g) gave 8:92 cis/trans-10-acetyl-9-methylspiro[4.5]dec-8-en-7-yl acetate (4.1 g, 82%).

trans-10-Acetyl-9-methylspiro[4.5]dec-8-en-7-yl $^{13}$C-NMR (100 MHz, CDCl$_3$): δ209.65 (s), 170.98 (s), 135.55 (s), 124.10 (d), 69.40 (d), 62.84 (d), 45.52 (s), 37.96 (t), 37.42 (t), 34.04 (t), 31.69 (q), 23.36 (t), 23.29 (t), 23.12 (q), 21.35 (q).

d) 1-(7-Methylspiro[4.5]deca-6,8-dien-6-yl)ethanone

A solution of 8:92 cis/trans-10-acetyl-9-methylspiro[4.5]dec-8-en-7-yl acetate (4.1 g, 16.4 mmol) in DBU (30 ml) was stirred for 19 h at 40° C. The reaction mixture was poured into cold 2N aqueous HCl (100 ml), and extracted twice with cyclohexane (50 ml). The combined organic phases were washed with water (50 ml), with a saturated aqueous solution of NaCl (40 ml), dried (MgSO$_4$), concentrated. FC (500 g SiO$_2$, hexane/MTBE 50:1) of the crude product (2.92 g) gave methyl 1-(7-methylspiro[4.5]deca-6,8-dien-6-yl)ethanone (2.25 g, 72%).

$^{13}$C-NMR (100 MHz, CDCl$_3$): δ208.57 (s), 141.47 (s), 128.80 (d), 127.30 (d), 127.11 (s), 44.82 (s, C(5')), 35.88 (t), 35.25 (t, 2C), 33.13 (q, MeCO), 23.48 (t, 2C), 19.03 (q).

MS (EI): 190 (5), 175 (70), 157 (15), 147 (73), 133 (18), 131 (18), 119 (20), 115 (12), 105 (100), 91 (31), 77 (19), 65 (10), 43 (53).

e) 3-Hydroxy-1-(7-methylspiro[4.5]deca-6,8-dien-6-yl)butan-1-one

Prepared in 68% yield after FC (300 g SiO$_2$, hexane/MTBE 4:1 to 3:1) from methyl 1-(7-methylspiro[4.5]deca-6,8-dien-6-yl)ethanone (2.25 g, 11.8 mmol), LDA, acetaldehyde as described in Example 10.

$^{13}$C-NMR (100 MHz, CDCl$_3$): δ212.12 (s), 140.40 (s), 128.68 (d), 128.00 (s), 127.76 (d), 63.70 (d), 53.28 (t), 45.00 (s, C(5')), 35.69 (t), 35.32 (t), 35.17 (t), 23.35 (t, 2C), 22.25 (q), 19.03 (q).

MS (EI): 234 (1), 216 (2), 201 (5), 190 (2), 187 (4), 175 (66), 159 (14), 147 (79), 133 (12), 131 (22), 119 (18), 117 (13), 115 (14), 105 (100), 91 (33), 77 (19), 69 (11), 45 (13), 43 (32).

f) (E)-1-(7-Methylspiro[4.5]deca-6,8-dien-6-yl)but-2-en-1-one

Prepared in 69% yield from 3-hydroxy-1-(7-methylspiro[4.5]deca-6,8-dien-6-yl)butan-1-one (1.88 g, 8.0 mmol), acetic anhydride (1.6 ml) and sodium acetate (0.72 g) as described in Example 10. Boiling point: 120° C. (0.09 mbar).

Odour description: Damascone-like, agrestic, fruity.

$^{13}$C-NMR (100 MHz, CDCl$_3$): δ201.45 (s), 146.12 (d), 138.60 (s), 134.65 (d), 128.79 (d), 128.41 (s), 127.12 (d), 45.13 (s, C(5')), 35.50 (t), 35.40 (t, 2C), 23.33 (t, 2C), 19.37 (q), 18.37 (q).

MS (EI): 216 (9), 201 (18), 187 (20), 173 (58), 159 (67), 147 (89), 146 (37), 145 (45), 131 (23), 117 (16), 115 (21), 105 (100), 91 (36), 77 (23), 69 (64), 41 (44), 39 (19).

Example 32

(E)-1-(7-Methylenespiro[4.5]dec-8-en-6-yl)but-2-en-1-one a) 1-(7-Methylenespiro[4.5]dec-8-en-6-yl)ethanone At 20° C., a solution of 8:92 cis-/trans-1-(9-hydroxy-7-methylspiro[4.5]dec-7-en-6-yl)ethanone (2 g, 9.7 mmol, prepared as described in Example 31) in toluene (20 ml) was treated with para-toluenesulfonic acid monohydrate (100 mg, 0.53 mmol) and molecular sieves, stirred for 16 h, treated with PTSA.H$_2$O (50 mg, 0.26 mmol), stirred for 4 h, treated with PTSA.H$_2$O (20 mg, 0.11 mmol), stirred for 3 h, treated with PTSA.H$_2$O (10 mg, 0.05 mmol), stirred for 19 h, treated with PTSA.H$_2$O (14 mg, 0.05 mmol), stirred for 2 h, treated with PTSA.H$_2$O (20 mg, 0.07 mmol), stirred for 6 h, poured into ice/saturated aqueous NaHCO$_3$ solution, and extracted three times with MTBE (30 ml). The organic phase was washed twice with a saturated aqueous solution of NaCl, dried (MgSO$_4$) and concentrated. FC (200 g SiO$_2$, hexane/MTBE 25:1) of the crude product (2 g) gave a 3:90:7 mixture of 1-(7-methylspiro[4.5]deca-7,9-dien-6-yl)ethanone, 1-(7-methylenespiro[4.5]dec-8-en-6-yl)ethanone, and 1-(7-is methylspiro[4.5]deca-6,8-dien-6-yl)ethanone (0.87 g, 47%) and recovered starting material (0.12 g, 6%).

1-(7-Methylenespiro[4.5]dec-8-en-6-yl)ethanone $^{13}$C-NMR (100 MHz, CDCl$_3$): δ208.47 (s), 140.79 (s), 130.40 (d), 127.25 (d), 115.29 (t), 63.80 (d, C(6')), 43.70 (s, C(5')), 39.01 (t), 37.73 (t), 35.16 (t), 30.02 (q), 24.49 (t), 23.65 (t).

MS (EI): 190 (1), 175 (3), 147 (85), 105 (100), 91 (36), 79 (23), 77 (19), 67 (9), 65 (9), 43 (41).

b) 3-Hydroxy-1-(7-methylenespiro[4.5]dec-8-en-6-yl)butan-1-one

At −70° C. under N$_2$, a solution of diisopropylamine (0.91 ml, 6.5 mmol) in anhydrous THF (10 ml) was treated dropwise with a solution of 1.6M n-BuLi in hexane (4 ml, 6.5 mmol). The resulting solution was stirred for 20 min., and treated dropwise with a solution of a 3:90:7 mixture of 1-(7-methylspiro[4.5]deca-7,9-dien-6-yl)ethanone, 1-(7-methylenespiro[4.5]dec-8-en-6-yl)ethanone, and 1-(7-methylspiro[4.5]deca-6,8-dien-6-yl)ethanone (0.94 g, 4.98 mmol) in anhydrous THF (4 ml). The resulting solution was stirred for 45 min. at −50° C., treated with a solution of acetaldehyde (1.2 ml, 20 mmol) in anhydrous THF (4 ml). The resulting solution was stirred at −40° C. for 1 h, poured into a mixture of ice and 2N HCl, and extracted three times with MTBE (25 ml). The combined organic phases washed with a saturated aqueous solution of NaCl, dried (MgSO$_4$), and concentrated. FC (40 g SiO$_2$, hexane/MTBE 10:1) of the crude product (1.3 g) gave 3-hydroxy-1-(7-methylenespiro[4.5]dec-8-en-6-yl)butan-1-one (0.788 g, 68%, 3:1 diast. mixture)

Major Diastereoisomer $^{13}$C-NMR (100 MHz, CDCl$_3$): δ211.96 (s), 140.16 (s), 130.49 (d), 127.20 (d), 115.57 (t), 63.75 (d), 63.56 (d), 50.41 (t), 43.81 (s, C(5'), 39.01 (t), 37.76 (t), 35.13 (t), 24.44 (t), 23.57 (t), 22.10 (q).

Minor Diastereoisomer $^{13}$C-NMR (100 MHz, CDCl$_3$): δ211.83 (s), 140.23 (s), 130.65 (d), 126.93 (d), 115.37 (t), 63.99 (d), 63.41 (d), 50.65 (t), 43.87 (s, C(5')), 38.98 (t), 37.81 (t), 35.25 (t), 24.49 (t), 23.57 (t), 22.10 (q).

c) A mixture of 3-hydroxy-1-(7-methylenespiro[4.5]dec-8-en-6-yl)butan-1-one (0.65 mg, 2.77 mmol, 3:1 diastereomeric mixture), acetic anhydride (0.55 ml, 5.8 mmol) and sodium acetate (0.25 g, 3.0 mmol) was stirred at 80° C. for 7 h, treated with sodium acetate (0.1 g, 1.2 mmol), stirred at 80° C. for 7 h, cooled to 0° C., poured into cold saturated aqueous NaHCO$_3$ (20 ml), and extracted three times with MTBE (10 ml). The combined organic phases were washed with a saturated aqueous solution of NaCl, dried (MgSO$_4$), and concentrated. FC (30 g SiO$_2$, hexane/MTBE 40:1) of the crude product (0.49 g) gave (E)-1-(7-methylenespiro[4.5]dec-8-en-6-yl)but-2-en-1-one (0.34 g, 57%). Boiling point: 100° C. (0.07 mbar).

Odour description: Damascone-like, earthy, spicy.

$^{13}$C-NMR (100 MHz, CDCl$_3$): δ199.04 (s), 142.40 (d), 140.71 (s), 130.86 (d), 130.51 (d), 127.69 (d), 115.33 (t), 61.06 (d, C(6')), 43.96 (s, C(5')), 39.15 (t), 37.49 (t), 35.37 (t), 24.47 (t), 23.78 (t), 18.18 (q).

MS (EI): 216 (3), 201 (3), 188 (4), 147 (62), 133 (8), 132 (6), 131 (10), 117 (10), 105 (46), 91 (26), 84 (4), 79 (17), 77 (16), 69 (100), 41 (31).

Example 33

(E)-1-(7-Methylspiro[4.5]deca-7,9-dien-6-yl)but-2-en-1-one a) 1-(7-Methylspiro[4.5]deca-7,9-dien-6-yl)ethanone A solution of 8:92 cis-/trans-1-(9-hydroxy-7-methylspiro[4.5]dec-7-en-6-yl)ethanone (2.69 g, 13 mmol, prepared as described in Example 31) in toluene (25 ml) was treated with para-toluenesulfonic acid monohydrate (250 mg, 1.3 mmol), heated at reflux for 45 min., cooled to 0° C., poured into ice/saturated aqueous NaHCO$_3$ solution, and the aqueous phase was extracted with MTBE (30 ml). The combined organic phases were washed three times with a saturated aqueous solution of NaCl, dried (MgSO$_4$) and concentrated. FC (240 g SiO$_2$, hexane/MTBE 25:1) of the crude product (3 g) gave a 58:13:29 mixture of 1-(7-methylspiro[4.5]deca-7,9-dien-6-yl)ethanone, 1-(7-methylspiro[4.5]deca-6,8-dien-6-yl)ethanone, and 1-(7-methylenespiro[4.5]dec-8-en-6-yl)ethanone (1.89 g, 76%) and recovered starting material (0.12 g, 6%).

1-(7-Methylspiro[4.5]deca-7,9-dien-6-yl)ethanone $^{13}$C-NMR (100 MHz, CDCl$_3$): δ208.99 (s), 134.25 (d), 132.22 (s), 122.18 (d), 121.11 (d), 64.87 (d, C(6')), 45.47 (s, C(5')), 40.78 (t), 35.67 (t), 26.70 (q), 23.92 (t), 22.70 (t), 22.52 (q).

MS (EI): 190 (4), 175 (1), 147 (28), 132 (1), 117 (6), 105 (100), 91 (8), 79 (5), 77 (7), 65 (3), 43 (18).

b) 3-Hydroxy-1-(7-methylspiro[4.5]deca-7,9-dien-6-yl)butan-1-one

At −70° C. under N$_2$, a solution of diisopropylamine (1.82 ml, 12.9 mmol) in anhydrous THF (20 ml) was treated dropwise with a solution of 1.6M n-BuLi in hexane (8.1 ml, 12.9 mmol). The resulting solution was stirred for 20 min., and treated dropwise with a solution of a 58:13:29 mixture of 1-(7-methylspiro[4.5]deca-7,9-dien-6-yl)ethanone, 1-(7-methylspiro[4.5]deca-6,8-dien-6-yl)ethanone, and 1-(7-methylenespiro[4.5]dec-8-en-6-yl)ethanone (1.89 g, 9.93 mmol) in anhydrous THF (10 ml). The resulting solution was stirred for 45 min. at −60° C., treated with a solution of acetaldehyde (2.4 ml, 40 mmol) in anhydrous THF (10 ml). The resulting solution was stirred at −40° C. for 1 h, poured into a mixture of ice and 2N HCl, and extracted three times with MTBE (100 ml). The combined organic phases washed three times with a saturated aqueous solution of NaCl, dried (MgSO$_4$), and concentrated. FC (250 g SiO$_2$, hexane/MTBE 10:1) of the crude product (2.4 g, α/β/γ 65:12:23) gave a 86:14 mixture of 3-hydroxy-1-(7-methylspiro[4.5]deca-7,9-dien-6-yl)butan-1-one and 3-hydroxy-1-(7-methylspiro[4.5]deca-6,8-dien-6-yl)butan-1-one (0.95 g, 40%) and a 63:9:28 mixture of 3-hydroxy-1-(7-methylspiro[4.5]deca-7,9-dien-6-yl)butan-1-one, 3-hydroxy-1-(7-methylspiro[4.5]deca-6,8-dien-6-yl)butan-1-one, and 3-hydroxy-1-(7-methylenespiro[4.5]dec-8-en-6-yl)butan-1-one (0.358 g, 15%) which after additional FC (30 g SiO$_2$, hexane/MTBE 10:1) gave a 81:14:3 mixture of 3-hydroxy-1-(7-methylspiro[4.5]deca-7,9-dien-6-yl)butan-1- one, 3-hydroxy-1-(7-methylspiro[4.5]deca-6,8-dien-6-yl)butan-1-one, and 3-hydroxy-1-(7-methylenespiro[4.5]dec-8-en-6-yl)butan-1-one (0.2 g).

3-Hydroxy-1-(7-methylspiro[4.5]deca-7,9-dien-6-yl)butan-1-one (major diastereoisomer)

$^{13}$C-NMR (100 MHz, CDCl$_3$): δ212.46 (s), 134.51 (d), 131.96 (s), 122.25 (d), 121.54 (d), 64.57 (d), 64.16 (d), 46.79 (t), 45.66 (s, C(5')), 41.02 (t), 35.46 (t), 23.11 (t), 22.85 (q), 22.50 (t), 22.22 (q).

MS (EI): 234 (1), 216 (1), 201 (1), 190 (1), 175 (2), 147 (37), 131 (3), 105 (100), 91 (8), 87 (4), 79 (5), 77 (7), 45 (8), 43 (13).

c) (E)-1-(7-Methylspiro[4.5]deca-7,9-dien-6-yl)but-2-en-1-one

A 81:14:3 mixture of 3-hydroxy-1-(7-methylspiro[4.5]deca-7,9-dien-6-yl)butan-1-one, 3-hydroxy-1-(7-methylspiro[4.5]deca-6,8-dien-6-yl)butan-1-one, and 3-hydroxy-1-(7-methylenespiro[4.5]dec-8-en-6-yl)butan-1-one (0.2 g, 0.85 mmol), acetic anhydride (0.17 ml, 1.8 mmol) and sodium acetate (77 mg, 3.0 mmol) was stirred at 80° C. for 16 h, treated with sodium acetate (30 mg, 0.37 mmol), stirred at 80° C. for 2 h, cooled to 0° C., poured into cold saturated aqueous NaHCO$_3$ (20 ml), and extracted three times with MTBE (10 ml). The combined organic phases were washed twice with a saturated aqueous solution of NaCl, dried (MgSO$_4$), and concentrated. FC (30 g SiO$_2$, hexane/MTBE 60:1) of the crude product (0.2 g) gave (E)-1-(7-methylspiro[4.5]deca-7,9-dien-6-yl)but-2-en-1-one (0.139 g, 77%). Boiling point: 100° C. (0.07 mbar).

Odour description: floral, Damascenone-like, slightly green.

$^{13}$C-NMR (100 MHz, CDCl$_3$): δ198.42 (s), 142.70 (d), 134.52 (s), 131.87 (d), 128.95 (d), 122.04 (d), 121.39 (d), 62.90 (d, C(6')), 45.53 (s, C(5')), 41.15 (t), 35.87 (t), 23.81 (t), 22.68 (q), 22.37 (t), 18.22 (q).

MS (EI): 216 (5), 201 (1), 188 (1), 147 (36), 131 (4), 117 (4), 105 (100), 91 (9), 79 (5), 77 (7), 69 (24), 41 (11).

Example 34

(E)-1-(Spiro[4.5]deca-2,6-dien-6-yl)but-2-en-1-one a) Spiro[4.5]dec-2-en-6-one

A solution of cyclohexanone (98.1 g, 1 mol), allyl alcohol (127.8 g, 2.2 mol), dimethoxypropane (114.6 g, 1.1 mol), and PTSA.H$_2$O (0.1 g, 0.5 mmol) in toluene (0.5 l) was heated at reflux in a flask equipped with a microdistillation column (30×2.5 cm, filled with Raschig rings). After collecting the fractions distilling at 25-60° C. and 60-110° C., the residue (120 g) was distilled using a 10 cm-Vigreux-column (0.07-0.06 mbar, head temperature: 57° C.) giving 2-allylcyclohexanone (99.1 g, 72%).

$^{13}$C-NMR (100 MHz, CDCl$_3$): δ212.14 (s), 136.38 (d), 116.05 (t), 50.14 (d), 41.93 (t), 33.69 (t), 39.29 (t), 27.85 (t), 24.87 (t).

MS (EI): 138 (36), 123 (21), 110 (18), 109 (52), 97 (19), 96 (12), 95 (59), 94 (74), 81 (48), 79 (74), 67 (100), 55 (61), 54 (61), 53 (35), 41 (86), 39 (57).

A solution of 2-allylcyclohexanone (50 g, 0.36 mol), allyl alcohol (46.2 g, 0.8 mol), dimethoxypropane (41.4 g, 0.4 mol), and PTSA.H$_2$O (35 mg, 0.18 mmol) in toluene (0.25 l) was heated at reflux in a flask equipped with a microdistilla-tion column (30×2.5 cm, filled with Raschig rings). After collecting the fractions distilling at 25-60° C. and 60-110° C., the residue (58 g) was distilled using a 10 cm-Vigreux-column giving a 28:72 mixture of 2-allylcyclohexanone/diallyl-cyclohexanones (36.85 g, 0.06 mbar, head temperature: 60° C.) and 6,6-diallylcyclohexanone (6.74 g, 10%, contaminated with 20% 2,6-diallylcyclohexanone, 0.06 mbar, head temperature: 60° C.). The first fraction was redistilled using a microdistillation column (20×1.0 cm, filled with 3×3 mm rolled wire netting) giving additional 6,6-diallylcyclohexanone (22.56 g, 35%, contaminated with 20% 2,6-diallycyclohexanone, 0.07 mbar, head temperature: 61-70° C.).

6,6-Diallylcyclohexanone $^{13}$C-NMR (100 MHz, CDCl$_3$): δ214.01 (s), 133.62 (d, 2 C), 118.00 (t, 2 C), 51.44 (s), 39.28 (t), 39.24 (t, 2 C), 35.93 (t), 27.02 (t), 20.77 (t).

MS (EI): 178 (8), 163 (3), 150 (4), 149 (8), 137 (49), 135 (43), 123 (13), 119 (16), 109 (16), 98 (11), 95 (24), 93 (46), 91 (39), 81 (31), 79 (60), 77 (28), 67 (100), 55 (55), 53 (29), 41 (69), 39 (41).

2,6-Diallylcyclohexanone $^{13}$C-NMR (100 MHz, CDCl$_3$): δ214.64 (s), 135.89 (d, 2 C), 116.44 (t, 2 C), 48.43 (d, 2 C), 34.54 (t, 2 C), 32.08 (t, 2 C), 20.31 (t).

A solution of a 80:20 mixture of 6,6- and 2,6-diallylcyclo-hexanone (22.0 g, 0.123 mol) in 1,2-dichloroethane (300 ml) was treated with PhCH=Ru(PCy$_3$)$_2$Cl$_2$ (10.2 g, 12.3 mmol). The resulting mixture was stirred at 60° C. for 24 h and concentrated. Ball-to-ball distillation (25-140° C., 0.1 mbar) of the residue (30.68 g) followed by FC (800 g SiO$_2$, hexane/MTBE 30:1) of the volatile fraction (14.9 g) gave spiro[4.5]dec-2-en-6-one (14.1 g, 95%).

$^{13}$C-NMR (100 MHz, CDCl$_3$): δ213.06 (s), 127.81 (d, 2 C), 55.73 (s, C(5)), 41.72 (t, 2 C), 40.12 (t), 39.48 (t), 27.19 (t), 22.26 (t).

MS (EI): 150 (96), 135 (41), 121 (33), 108 (34), 107 (48), 106 (49), 93 (81), 91 (43), 80 (63), 79 (100), 77 (58), 67 (25), 66 (37), 65 (29), 55 (38), 41 (29), 39 (45).

b) 1-(Spiro[4.5]deca-2,6-dien-6-yl)ethanone

Prepared as described in Example 10, from spiro[4.5]dec-2-en-6-one via 6-ethynylspiro[4.5]dec-2-en-6-ol (lithium acetylide ethylene diamine complex, THF, 53%) that was transformed into crude 6-ethynylspiro[4.5]deca-2,6-diene (POCl$_3$, pyridine, 90° C., 3.5 h) leading after conc. H$_2$SO$_4$/AcOH treatment (85° C., 1 h) to 1-(spiro[4.5]deca-2,6-dien-6-yl)ethanone (61%, 2 steps).

6-Ethynylspiro[4.5]dec-2-en-6-ol $^{13}$C-NMR (100 MHz, CDCl$_3$): δ129.24 (d), 128.73 (d), 86.99 (s), 73.76 (s), 73.06 (d), 49.60 (s, C(5)), 42.89 (br. t), 39.48 (br. t), 36.68 (t), 35.14 (br. t), 22.26 (br. t), 21.46 (t).

MS (EI): 176 (1), 175 (3), 161 (10), 158 (45), 148 (19), 147 (18), 143 (62), 133 (27), 130 (54), 129 (77), 128 (30), 120 (23), 119 (25), 117 (41), 116 (35), 115 (49), 105 (40), 91 (100), 79 (97), 77 (72), 67 (56), 66 (47), 65 (38), 55 (42), 53 (70), 51 (27), 41 (37), 39 (46).

6-Ethynylspiro[4.5]deca-2,6-diene $^{13}$C-NMR (100 MHz, CDCl$_3$): δ136.56 (d), 128.89 (d, 2 C), 128.37 (s), 83.81 (s), 76.76 (d), 45.98 (t, 2 C), 44.03 (s, C(5)), 36.56 (t), 26.00 (t), 19.25 (t).

MS (EI): 158 (28), 157 (12), 143 (42), 130 (51), 129 (100), 128 (67), 116 (21), 115 (69), 103 (17), 91 (37), 77 (31), 65 (18), 63 (19), 51 (22), 39 (21).

1-(Spiro[4.5]deca-2,6-dien-6-yl)ethanone $^{13}$C-NMR (100 MHz, CDCl$_3$): δ199.67 (s, CO), 146.22 (s, C(6)), 141.68 (d, C(7)), 128.75 (d, 2 C), 46.68 (t, 2 C), 42.10 (s, C(5)), 38.93 (t), 27.14 (q), 26.63 (t), 18.65 (t).

MS (EI): 178 (1), 161 (18), 148 (19), 147 (18), 135 (39), 133 (80), 117 (15), 115 (13), 105 (56), 91 (100), 79 (28), 77 (36), 65 (18), 51 (16), 43 (75), 39 (20).

c) (E)-1-(Spiro[4.5]deca-2,6-dien-6-yl)but-2-en-1-one

Prepared as described in Example 10, from 1-(spiro[4.5]deca-2,6-dien-6-yl)ethanone via 3-hydroxy-1-(spiro[4.5]deca-2,6-dien-6-yl)butan-1-one (LDA, acetaldehyde, THF, 72% after FC (SiO$_2$, hexane/MTBE 1:1); 17% starting material recovered) and subsequent Ac$_2$O/AcONa treatment (35% after FC (SiO$_2$, hexane/MTBE 30:1)). Boiling point: 110° C. (0.08 mbar).

Odour description: rosy, green, fruity.

$^{13}$C-NMR (100 MHz, CDCl$_3$): δ193.02 (s, CO), 146.20 (s), 142.18 (d), 139.17 (d), 129.15 (d), 128.81 (d, 2 C), 46.61 (t, 2 C), 42.40 (s, C(5)), 38.56 (t), 26.20 (t), 18.74 (t), 18.25 (q).

MS (EI): 202 (37), 187 (75), 174 (19), 173 (45), 161 (46), 159 (49), 145 (41), 133 (29), 131 (47), 117 (37), 115 (28), 105 (38), 95 (43), 91 (100), 79 (34), 77 (54), 69 (57), 67 (20), 65 (27), 55 (24), 51 (20), 41 (68), 39 (43).

Example 35

Perfume Composition

| Ingredients | parts by weight 1/1000 |
| --- | --- |
| Citronellyl Acetate | 50 |
| Agrumex (2-tert-butylcyclohexyl acetate) | 150 |
| Phenyl Ethyl Alcohol | 100 |
| Iso C11 Aldehyde (undec-9-enal) | 2 |
| Citronellol | 225 |
| Cyclal C (main component: 2,4-dimethyl-3-cyclohexen-1-carbaldehyde) | 4 |
| Eugenol | 10 |
| Beta Ionone | 50 |
| Isoraldeine ® 70 (mixture of CAS 1335-46-2, 127-51-5, 127-42-4) | 100 |
| Linalool (3,7-dimethylocta-1,6-dien-3-ol) | 150 |
| Pandanol ((2-methoxyethyl)benzene) | 2 |
| Peonile ® (2-cyclohexylidene-2-phenylacetonitrile) | 150 |
| Rose Oxide (4-methyl-2-(2-methylprop-1-enyl)tetrahydro-2H-pyran) | 5 |
| (E)-1-(rel-(6S,7R)-7-Methylspiro[4.5]dec-8-en-6-yl)but-2-en-1-one | 2 |

The addition of (E)-1-(rel-(6S,7R)-7-methylspiro[4.5]dec-8-en-6-yl)but-2-en-1-one of Example 1 imparts a very positive aspect to this floral fruity fragrance up to the dry-out stage. With its very specific plum 'Mirabelle' tone, the rose ketone related character of (E)-1-(rel-(6S,7R)-7-methylspiro[4.5]dec-8-en-6-yl)but-2-en-1-one enhances the natural scent of the rose petals accord and enriches the honey accord.

The invention claimed is:

1. A fragrance compound according to formula (I)

(I)

wherein:
n is 1, 2, 3, or 4;
m is 1;
R$^1$ is selected from: methoxy, ethoxy, propoxy, C$_2$-C$_4$ alkenoxy, C$_2$-C$_5$ alkyl, C$_2$-C$_5$ alkenyl, cyclopropyl, 2-methylcyclopropyl, 1-methylcyclopropyl, and cyclopropylmethyloxy;
R$^2$ is selected from: hydrogen, methyl, ethyl, methylene, and ethylidene;
ring A is saturated, or unsaturated comprising 1 double bond or 2 double bonds;
ring B is saturated.

2. A fragrance compound according to claim 1 wherein the compound of formula (I) is selected from the group consisting of:
(E)-1-(7-methylspiro[4.5]dec-8-en-6-yl)but-2-en-1-one;
methyl 7-methylspiro[4.5]dec-8-ene-6-carboxylate;
ethyl 7-methylspiro[4.5]dec-8-ene-6-carboxylate;
allyl 7-methylspiro[4.5]dec-8-ene-6-carboxylate;
methyl 7-methylspiro[4.5]decane-6-carboxylate;
ethyl 7-methylspiro[4.5]decane-6-carboxylate;
1-(7-methylspiro[4.5]decan-6-yl)butan-1-one;
1-(7-methylspiro[4.5]dec-8-en-6-yl)butan-1-one;
(E)-1-(7-methylspiro[4.5]decan-6-yl)but-2-en-1-one;
(E)-1-(spiro[4.5]dec-6-en-6-yl)but-2-en-1-one;
(E)-1-(5-methylspiro[2.5]oct-6-en-4-yl)but-2-en-1-one;
(E)-1-(5-methylspiro[2.5]oct-5-en-4-yl)but-2-en-1-one;
ethyl 7-methylspiro[4.5]dec-7-ene-6-carboxylate;
(E)-1-(7-methylspiro[4.5]dec-7-en-6-yl)but-2-en-1-one;
(E)-1-(7-methylspiro[4.5]dec-6-en-6-yl)but-2-en-1-one;
ethyl 7-methylenespiro[4.5]dec-8-ene-6-carboxylate;
ethyl 7-methylspiro[4.5]deca-6,8-diene-6-carboxylate;
ethyl 7-methylspiro[4.5]deca-7,9-diene-6-carboxylate;
(2-methylcyclopropyl)(7-methylspiro[4.5]dec-8-en-6-yl)methanone;
methyl 7-methylspiro[4.5]dec-7-ene-6-carboxylate;
methyl 7-methylspiro[4.5]dec-6-ene-6-carboxylate;
ethyl 7-methylspiro[4.5]dec-6-ene-6-carboxylate;
(E)-1-(7-methylspiro[4.5]dec-6-en-6-yl)but-2-en-1-one;
methyl 7-methylspiro[4.5]dec-9-ene-6-carboxylate;
ethyl 7-methylspiro[4.5]dec-9-ene-6-carboxylate;
(E)-1-(7-methylspiro[4.5]dec-9-en-6-yl)but-2-en-1-one;
(E)-1-(7-methylspiro[4.5]deca-6,8-dien-6-yl)but-2-en-1-one;
(E)-1-(7-methylspiro[4.5]deca-7,9-dien-6-yl)but-2-en-1-one;
(E)-1-(7-methylenespiro[4.5]dec-8-en-6-yl)but-2-en-1-one;
methyl 2-methylspiro[4.4]non-1-ene-1-carboxylate;
ethyl 2-methylspiro[4.4]non-1-ene-1-carboxylate;
(E)-1-(2-methylspiro[4.4]non-1-en-1-yl)but-2-en-1-one;
methyl 2-methylspiro[4.4]non-2-ene-1-carboxylate;
ethyl 2-methylspiro[4.4]non-2-ene-1-carboxylate;
(E)-1-(2-methylspiro[4.4]non-2-en-1-yl)but-2-en-1-one;

cyclopropyl(7-methyl-spiro[4.5]dec-8-en-6-yl)methanone;
(2-methylcyclopropyl)(7-methyl-spiro[4.5]deca-6,8-dien-6-yl)methanone;
cyclopropyl(7-methylspiro[4.5]deca-6,8-dien-6-yl)methanone;
methyl 7-ethylidenespiro[4.5]decane-6-carboxylate;
ethyl 7-ethylidenespiro[4.5]decane-6-carboxylate;
(2E)-1-(7-ethylidenespiro[4.5]decan-6-yl)but-2-en-1-one;
methyl 7-methylspiro[4.5]dec-9-ene-6-carboxylate;
methyl 7-methylspiro[4.5]deca-6,8-diene-6-carboxylate;
methyl 7-methylenespiro[4.5]dec-8-ene-6-carboxylate;
ethyl 7-methylenespiro[4.5]decane-6-carboxylate;
methyl 7-methylenespiro[4.5]decane-6-carboxylate;
(E)-1-(7-methylenespiro[4.5]decan-6-yl)but-2-en-1-one;
(E)-1-(7-methylenespiro[4.5]dec-2-en-6-yl)but-2-en-1-one; and,
(E)-1-(7-methylspiro[4.5]deca-2,6,8-trien-6-yl)but-2-en-1-one.

3. A fragrance composition comprising a compound of formula (I) according to claim 1, and at least one other odorant molecule.

4. A method of manufacturing a fragrance application, comprising the step of: incorporating a compound of formula (I) according to claim 1 into a consumer product base.

5. A compound according to formula (I)

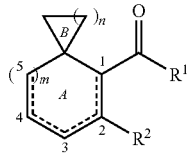

(I)

wherein
n is 1, 2, 3, or 4;
m is 1;
$R^1$ is selected from $C_1$-$C_4$ alkoxy, $C_3$-$C_4$ cycloalkyloxy, $C_2$-$C_4$ alkenoxy, $C_2$-$C_5$ alkyl, $C_2$-$C_5$ alkenyl, cyclopropyl, 2-methylcyclopropyl, 1-methylcyclopropyl, and cyclopropylmethyloxy;
$R^2$ is selected from hydrogen, methyl, ethyl, methylene, and ethylidene;
ring A is saturated, or unsaturated comprising 1 double bond or 2 double bonds;
ring A is saturated or unsaturated comprising 1 double bond or 2 double bonds,
ring B is saturated;
provided that:
tert-butyl spiro[4.5]decane-6-carboxylate; and,
methyl spiro[5.5]undec-4-ene-1-carboxylate, are excluded.

6. A method of producing a fragrance compound of formula (I)

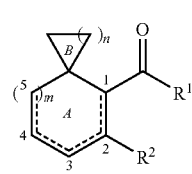

(I)

wherein:
n is 1, 2, 3, or 4;
m is 0 or 1;
$R^1$ is selected from $C_1$-$C_4$ alkoxy, $C_3$-$C_4$ cycloalkyloxy, $C_2$-$C_4$ alkenoxy, $C_2$-$C_5$ alkyl, $C_2$-$C_5$ alkenyl, cyclopropyl, 2-methylcyclopropyl, 1-methylcyclopropyl, and cyclopropylmethyloxy;
$R^2$ is selected from hydrogen, methyl, ethyl, methylene, and ethylidene;
ring A is saturated, or unsaturated comprising 1 double bond or 2 double bonds;
ring B is saturated, or unsaturated comprising 1 double bond or 2 double bonds;
the method comprising the step of:
elimination of HX from a compound of formula (II)

(II)

wherein:
n, m, $R^1$ and $R^2$ have the same meaning as given above for formula (I);
ring A is saturated or unsaturated comprising 1 double bond;
ring B is saturated, or unsaturated comprising 1 double bond or 2 double bonds; and,
X is selected from —OR" wherein R" is selected from hydrogen, $C_1$-$C_{12}$ alkyl, or $C_2$-$C_{12}$ alkenyl, —O—C(O)R''' wherein R''' is $C_1$ to $C_{12}$ alkyl, and —O—$CO_2R^{IV}$ wherein $R^{IV}$ is $C_1$ to $C_{12}$ alkyl, and
X is bound to C-2, C-3 or C-4;
under acidic or basic conditions.

7. A fragrance composition comprising a compound of formula (I) according to claim 2, and at least one other odorant molecule.

8. A method of manufacturing a fragrance application, comprising the step of: incorporating a compound of formula (I) according to claim 2 into a consumer product base.

9. A fragrance compound according to claim 1, wherein the fragrance compound of formula (I) exhibits damascene-like odor notes.

10. A fragrance compound according to claim 2, wherein the fragrance compound of formula (I) exhibits damascene-like odor notes.

11. A fragrance composition according to claim 3, wherein the fragrance compound of formula (I) exhibits damascene-like odor notes.

12. A method of manufacturing a fragrance application according to claim 4, wherein the fragrance compound of formula (I) exhibits damascene-like odor notes.

13. A compound of formula (I) according to claim 5, wherein the fragrance compound of formula (I) exhibits damascene-like odor notes.

14. A method according to claim 6, wherein the fragrance compound of formula (I) exhibits damascene-like odor notes.

15. A method of manufacturing a fragrance application according to claim 4, wherein the consumer product base is a composition used as a consumer product which provides a cleaning, softening or caring action.

16. A method according to claim 15, wherein the consumer product base is a fabric care produce or a personal care product.

17. A method of manufacturing a fragrance application according to claim 8, wherein the consumer product base is a composition used as a consumer product which provides a cleaning, softening or caring action.

18. A method according to claim 17, wherein the consumer product base is a fabric care produce or a personal care product.

* * * * *